(12) United States Patent
Jonkers et al.

(10) Patent No.: US 10,273,507 B2
(45) Date of Patent: Apr. 30, 2019

(54) CELLS WITH IMPROVED PENTOSE CONVERSION

(71) Applicant: DSM IP ASSETS B.V., Heerlen (NL)

(72) Inventors: Maria Bernedina Elizabeth Jonkers, Echt (NL); Paul Klaassen, Echt (NL); Aloysius Wilhelmus Rudolphus Hubertus Teunissen, Echt (NL); Rene Marcel De Jong, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/434,116

(22) PCT Filed: Oct. 15, 2013

(86) PCT No.: PCT/EP2013/071462
§ 371 (c)(1),
(2) Date: Apr. 8, 2015

(87) PCT Pub. No.: WO2014/060377
PCT Pub. Date: Apr. 24, 2014

(65) Prior Publication Data
US 2015/0275235 A1 Oct. 1, 2015

(30) Foreign Application Priority Data

Oct. 16, 2012 (EP) .................................... 12188715
May 8, 2013 (EP) .................................... 13166959

(51) Int. Cl.
*C12N 1/16* (2006.01)
*C12N 1/22* (2006.01)
(Continued)

(52) U.S. Cl.
CPC ................. *C12P 7/06* (2013.01); *C12N 1/16* (2013.01); *C12N 1/22* (2013.01); *C12N 9/1022* (2013.01); *C12N 9/1205* (2013.01); *C12N 9/88* (2013.01); *C12N 9/90* (2013.01); *C12N 9/92* (2013.01); *C12P 7/10* (2013.01); *C12Y 404/01005* (2013.01); *C12Y 202/01001* (2013.01); *C12Y 202/01002* (2013.01); (Continued)

(58) Field of Classification Search
None
See application file for complete search history.

(56) References Cited

FOREIGN PATENT DOCUMENTS

WO 03/062430 A1 7/2003
WO 03062340 A1 7/2003
(Continued)

OTHER PUBLICATIONS

U.S. Appl. No. 61/671,848, filed Jul. 16, 2012.*
(Continued)

*Primary Examiner* — Richard C Ekstrom
(74) *Attorney, Agent, or Firm* — McBee Moore Woodward & Vanik IP, LLC; Susan McBee; Chester Moore

(57) ABSTRACT

The invention relates to a cell capable of converting one or more pentose sugar and one or more hexose sugar into fermentation product constitutively expressing one or more heterologous or homologous polypeptide having the amino acid sequence set out in SEQ ID NO: 20, or a variant polypeptide thereof having at least 45% identity to SEQ ID NO 20. In an embodiment the heterologous polypeptide has glyoxalase activity.

19 Claims, 30 Drawing Sheets
Specification includes a Sequence Listing.

(51) Int. Cl.
*C12N 9/88* (2006.01)
*C12P 7/06* (2006.01)
*C12P 7/10* (2006.01)
*C12N 9/10* (2006.01)
*C12N 9/12* (2006.01)
*C12N 9/90* (2006.01)
*C12N 9/92* (2006.01)

(52) U.S. Cl.
CPC ............ *C12Y 207/01017* (2013.01); *C12Y 501/03001* (2013.01); *C12Y 503/01006* (2013.01); *Y02E 50/16* (2013.01); *Y02E 50/17* (2013.01)

(56) References Cited

FOREIGN PATENT DOCUMENTS

| WO | 06009434 A1 | 1/2006 | |
|---|---|---|---|
| WO | WO 2009109633 A1 * | 9/2009 | ............... C12N 9/92 |
| WO | 2012/015949 A2 | 2/2012 | |
| WO | WO 2014003555 A1 * | 1/2014 | ..... C12Y 404/01005 |

OTHER PUBLICATIONS

GenBank Accession No. CAA67622.1, published Apr. 18, 2005.*
Gen Bank Accession No. X99240.1, published Apr. 18, 2005.*
International Search Report from corresponding PCT/EP2013/071462, dated Jan. 20, 2014.
Liu et al., "Preparation of High-Activity Whole Cell Biocatalysts by Permeabilization of Recombinant Yeasts with Alcohol", vol. 89, No. 6, pp. 554-558, 2000, XP-002220828.
Lonn et al., "Xylose isomerase activity influences xylose fermentation with recombinant *Saccharomyces cerevisiae* strains expressing mutated xylA from Thermus thermophilus", Elsevier, Science Direct, Enzyme and Microbial Technology 32 (2003) pp. 567-573, XP-002312914.
Traeff-Bjerre et al., "Endogenous NADPH-dependent aldose reductase activity influences product formation during xylose consumption in recombinant *Saccharomyces cerevisiae*", Yeast 2004; 21: pp. 141-150, Jan. 30, XP-002991613.
Brat et al. "Functional Expression of a Bacterial Xylose Isomerase in *Saccharomyces cerevisiae*", Applied and Environmental Microbiology, Apr. 2009, pp. 2304-2311, XP9121860.
Ha et al, "Xylitol does not inhibit xylose fermentation by engineered *Saccharomyces cerevisiae* expressing xylA as severely as it inhibits xylose isomerase reaction in vitro", Apply Microbiol Biotechnol (2011), XP19950886.
Frickel et al., "Yeast Glyoxalase I Is a Monomeric Enzyme with Two Active Sites", The Journal of Biological Chemistry, vol. 276, No. 3, Issue of Jan. 19, pp. 1845-1849, 2001, XP55052534.
Inoue et al., "Identification of the Structural Gene for Glyoxalase I from *Saccharomyces cerevisiae*", The Journal of Biological Chemistry, vol. 271, No. 42, Issue of Oct. 18, pp. 25958-25965, 1996, XP55052555.
Aguilera et al., "The *Saccharomyces cerevisiae* aldose reductase is implied in the metabolism of methylglyoxal in response to stress conditions", Curr Genet (2001) pp. 273-283, Jan. 22, 2001, XP55052746.
Zhu, Marie M. et al., "Accumulation of Methyigloxal in Anaerobically Grown *Escherichia coli* and Its Detoxification by Expression of the Pseudomonas putida Glyoxalase I Gene", Metabolic Engineering, 2001, pp. 218-225, vol. 3.
Scheckhuber, Christian Q. et al., "Modulation of the glyoxalase system in the aging model Podospora anserina: effects on growth and lifespan", Dec. 2010, pp. 969-980, vol. 2, No. 12.

* cited by examiner

Integration site 1 (Chr XV, coordinates 458319 bp to 459320 bp)

The specified map is indicated by the region between the two vertical dashed lines

SEQUENCE LISTING

```
<160> NUMBER OF SEQ ID NOS: 38

<210> SEQ ID NO 1
<211> LENGTH: 32
<212> TYPE: DNA
<213> ORGANISM: Artificial Sequence
<220> FEATURE:
<223> OTHER INFORMATION: Forward primer PGK1 promoter
<220> FEATURE:
<221> NAME/KEY: source
<222> LOCATION: (1)..(32)
<223> OTHER INFORMATION: /organism="Artificial Sequence" /note="Forward
      primer PGK1 promoter" /mol_type="unassigned DNA"

<400> SEQUENCE: 1
actagtctcg agctcttcaa ctcaagacgc ac                                     32

<210> SEQ ID NO 2
<211> LENGTH: 36
<212> TYPE: DNA
<213> ORGANISM: Artificial Sequence
<220> FEATURE:
<223> OTHER INFORMATION: Reverse primer PGI1 terminator
<220> FEATURE:
<221> NAME/KEY: source
<222> LOCATION: (1)..(36)
<223> OTHER INFORMATION: /organism="Artificial Sequence" /note="Reverse
      primer PGI1 terminator" /mol_type="unassigned DNA"

<400> SEQUENCE: 2
ttaagcttcg tacgttttaa acagttgatg agaacc                                 36

<210> SEQ ID NO 3
<211> LENGTH: 26
<212> TYPE: DNA
<213> ORGANISM: Artificial Sequence
<220> FEATURE:
<223> OTHER INFORMATION: Forward primer ACT1 gene
<220> FEATURE:
<221> NAME/KEY: source
```

```
<222> LOCATION: (1)..(26)
<223> OTHER INFORMATION: /organism="Artificial Sequence" /note="Forward
      primer ACT1 gene" /mol_type="unassigned DNA"

<400> SEQUENCE: 3
ccattttgag aatcgatttg gccggt                                            26

<210> SEQ ID NO 4
<211> LENGTH: 28
<212> TYPE: DNA
<213> ORGANISM: Artificial Sequence
<220> FEATURE:
<223> OTHER INFORMATION: Reverse primer ACT1 gene
<220> FEATURE:
<221> NAME/KEY: source
<222> LOCATION: (1)..(28)
<223> OTHER INFORMATION: /organism="Artificial Sequence" /note="Reverse
      primer ACT1 gene" /mol_type="unassigned DNA"

<400> SEQUENCE: 4
ggtgatttcc ttttgcattc tttcggca                                          28

<210> SEQ ID NO 5
<211> LENGTH: 24
<212> TYPE: DNA
<213> ORGANISM: Artificial Sequence
<220> FEATURE:
<223> OTHER INFORMATION: Forward primer GLO1 gene, Q-PCR
<220> FEATURE:
<221> NAME/KEY: source
<222> LOCATION: (1)..(24)
<223> OTHER INFORMATION: /organism="Artificial Sequence" /note="Forward
      primer GLO1 gene, Q-PCR" /mol_type="unassigned DNA"

<400> SEQUENCE: 5
ggagagcctg atgtttttag cgca                                              24

<210> SEQ ID NO 6
<211> LENGTH: 23
<212> TYPE: DNA
<213> ORGANISM: Artificial Sequence
<220> FEATURE:
<223> OTHER INFORMATION: Reverse primer GLO1 gene, Q-PCR
<220> FEATURE:
<221> NAME/KEY: source
<222> LOCATION: (1)..(23)
<223> OTHER INFORMATION: /organism="Artificial Sequence" /note="Reverse
      primer GLO1 gene, Q-PCR" /mol_type="unassigned DNA"

<400> SEQUENCE: 6
tcaatccagt atccatcagg gcc                                               23

<210> SEQ ID NO 7
<211> LENGTH: 29
<212> TYPE: DNA
<213> ORGANISM: Artificial Sequence
<220> FEATURE:
<223> OTHER INFORMATION: Forward primer ALG9 gene, Q-PCR
<220> FEATURE:
<221> NAME/KEY: source
<222> LOCATION: (1)..(29)
<223> OTHER INFORMATION: /organism="Artificial Sequence" /note="Forward
      primer ALG9 gene, Q-PCR" /mol_type="unassigned DNA"

<400> SEQUENCE: 7
cacggatagt ggctttggtg aacaattac                                         29

<210> SEQ ID NO 8
<211> LENGTH: 32
```

<212> TYPE: DNA
<213> ORGANISM: Artificial Sequence
<220> FEATURE:
<223> OTHER INFORMATION: Reverse primer ALG9 gene, Q-PCR
<220> FEATURE:
<221> NAME/KEY: source
<222> LOCATION: (1)..(32)
<223> OTHER INFORMATION: /organism="Artificial Sequence" /note="Reverse primer ALG9 gene, Q-PCR" /mol_type="unassigned DNA"

<400> SEQUENCE: 8
tatgattatc tggcagcagg aaagaacttg gg                                32

<210> SEQ ID NO 9
<211> LENGTH: 29
<212> TYPE: DNA
<213> ORGANISM: Artificial Sequence
<220> FEATURE:
<223> OTHER INFORMATION: Forward primer UBC6 gene, Q-PCR
<220> FEATURE:
<221> NAME/KEY: source
<222> LOCATION: (1)..(29)
<223> OTHER INFORMATION: /organism="Artificial Sequence" /note="Forward primer UBC6 gene, Q-PCR" /mol_type="unassigned DNA"

<400> SEQUENCE: 9
gatacttgga atcctggctg gtctgtctc                                   29

<210> SEQ ID NO 10
<211> LENGTH: 32
<212> TYPE: DNA
<213> ORGANISM: Artificial Sequence
<220> FEATURE:
<223> OTHER INFORMATION: Reverse primer UBC6 gene, Q-PCR
<220> FEATURE:
<221> NAME/KEY: source
<222> LOCATION: (1)..(32)
<223> OTHER INFORMATION: /organism="Artificial Sequence" /note="Reverse primer UBC6 gene, Q-PCR" /mol_type="unassigned DNA"

<400> SEQUENCE: 10
aaagggtctt ctgtttcatc acctgtattt gc                               32

<210> SEQ ID NO 11
<211> LENGTH: 75
<212> TYPE: DNA
<213> ORGANISM: Artificial Sequence
<220> FEATURE:
<223> OTHER INFORMATION: Forward primer HIS3 cassette, 5' flank INT1
<220> FEATURE:
<221> NAME/KEY: source
<222> LOCATION: (1)..(75)
<223> OTHER INFORMATION: /organism="Artificial Sequence" /note="Forward primer HIS3 cassette, 5' flank INT1" /mol_type="unassigned DNA"

<400> SEQUENCE: 11
cagttttaaa aagtcagaga atgtagagaa gtatggatct tgaaaccct ttggtgagcg  60 ctaggagtca ctgcc                                                  75

<210> SEQ ID NO 12
<211> LENGTH: 75
<212> TYPE: DNA
<213> ORGANISM: Artificial Sequence
<220> FEATURE:
<223> OTHER INFORMATION: Reverse primer GLO1 cassette, 3' flank INT1
<220> FEATURE:
<221> NAME/KEY: source
<222> LOCATION: (1)..(75)
<223> OTHER INFORMATION: /organism="Artificial Sequence" /note="Reverse primer GLO1 cassette, 3' flank INT1" /mol_type="unassigned DNA"

<400> SEQUENCE: 12
atcttacata gtgtcgggaa caggtcattc taaaaaaagt aaaataaaat acgttttaaa    60
cagttgatga gaacc    75

<210> SEQ ID NO 13
<211> LENGTH: 75
<212> TYPE: DNA
<213> ORGANISM: Artificial Sequence
<220> FEATURE:
<223> OTHER INFORMATION: Reverse primer HIS3 cassette, 3' flank INT1
<220> FEATURE:
<221> NAME/KEY: source
<222> LOCATION: (1)..(75)
<223> OTHER INFORMATION: /organism="Artificial Sequence" /note="Reverse
      primer HIS3 cassette, 3' flank INT1" /mol_type="unassigned DNA"

<400> SEQUENCE: 13
cataatatgt taaaagctag atcttacata gtgtcgggaa caggtcattc ttcacaccgc    60
atatgatccg tcgag    75

<210> SEQ ID NO 14
<211> LENGTH: 19
<212> TYPE: DNA
<213> ORGANISM: Artificial Sequence
<220> FEATURE:
<223> OTHER INFORMATION: Forward primer 5' flank INT1
<220> FEATURE:
<221> NAME/KEY: source
<222> LOCATION: (1)..(19)
<223> OTHER INFORMATION: /organism="Artificial Sequence" /note="Forward
      primer 5' flank INT1" /mol_type="unassigned DNA"

<400> SEQUENCE: 14
cggcattatt gtgtatggc    19

<210> SEQ ID NO 15
<211> LENGTH: 23
<212> TYPE: DNA
<213> ORGANISM: Artificial Sequence
<220> FEATURE:
<223> OTHER INFORMATION: Reverse primer 5' flank INT1
<220> FEATURE:
<221> NAME/KEY: source
<222> LOCATION: (1)..(23)
<223> OTHER INFORMATION: /organism="Artificial Sequence" /note="Reverse
      primer 5' flank INT1" /mol_type="unassigned DNA"

<400> SEQUENCE: 15
agggtttcaa agatccatac ttc    23

<210> SEQ ID NO 16
<211> LENGTH: 24
<212> TYPE: DNA
<213> ORGANISM: Artificial Sequence
<220> FEATURE:
<223> OTHER INFORMATION: Forward primer 3' flank INT1
<220> FEATURE:
<221> NAME/KEY: source
<222> LOCATION: (1)..(24)
<223> OTHER INFORMATION: /organism="Artificial Sequence" /note="Forward
      primer 3' flank INT1" /mol_type="unassigned DNA"

<400> SEQUENCE: 16
gaatgacctg ttcccgacac tatg    24

<210> SEQ ID NO 17

```
<211> LENGTH: 24
<212> TYPE: DNA
<213> ORGANISM: Artificial Sequence
<220> FEATURE:
<223> OTHER INFORMATION: Reverse primer 3' flank INT1
<220> FEATURE:
<221> NAME/KEY: source
<222> LOCATION: (1)..(24)
<223> OTHER INFORMATION: /organism="Artificial Sequence" /note="Reverse
      primer 3' flank INT1" /mol_type="unassigned DNA"

<400> SEQUENCE: 17
cacaagctta ttcttccaaa aatc                                            24

<210> SEQ ID NO 18
<211> LENGTH: 500
<212> TYPE: DNA
<213> ORGANISM: Saccharomyces cerevisiae
<220> FEATURE:
<221> NAME/KEY: source
<222> LOCATION: (1)..(500)
<223> OTHER INFORMATION: /organism="Saccharomyces cerevisiae" /mol_type=
      "unassigned DNA"

<400> SEQUENCE: 18
cggcattatt gtgtatggct caataatttt ataaaaaaag gaactattgg ttcttagtat     60
tttcttgcta gaagacatat tcttaccaat cctttcataa gctaattatg ccatccatat    120
agcaagagaa tccggtgggg cgccatgcc tatccggcgg caacattatt actctggtat    180
acgggcgtaa ctccataata tgccaccact tacctttaac atgttcatgg taggtacccc    240
acccagccat aaggaaattt tcaaaggcgt tggatcaaaa aataggcctt tatttcatcg    300
cgtgattgag gagcataaca tgtttagtga aggtttcttt tggaaaactt cagtcgctca    360
ttattagaac cagggaggtc caggctttgc tggtgggaga gaaagcttat gaagctgggg    420
ttgcagattt gtcgattggt cgccagtaca cagtttttaaa aagtcagaga atgtagagaa    480
gtatggatct ttgaaaccct                                                500

<210> SEQ ID NO 19
<211> LENGTH: 478
<212> TYPE: DNA
<213> ORGANISM: Saccharomyces cerevisiae
<220> FEATURE:
<221> NAME/KEY: source
<222> LOCATION: (1)..(478)
<223> OTHER INFORMATION: /organism="Saccharomyces cerevisiae" /mol_type=
      "unassigned DNA"

<400> SEQUENCE: 19
gaatgacctg ttcccgacac tatgtaagat ctagcttta acatattatg gaaacctgaa     60
atgtaaaatc tgaattttg tatatgtgtt tatatttggg tagttctttt gaggaaagca    120
tgcatagact tgctgtacga actttatgtg acttgtagtg acgctgtttc atgagacttt    180 agcccttga acatattatc atatctcagc ttgaaatact atagatttac ttttgcagcc    240
atttcttggt gctccaaggt tgtgcgtatc tattacttaa tttctgtcct tgccaagttt    300
tgcagcaggg cggtcacaag actcctctgc cgtcattcct tagtccttcg ggaacacact    360
tatttatgta tttgtattct acaattctac ggtgcacaag ggttgggcac tgttgagctc    420
agcacgcaac tattgctggc atgaagataa gattgatttt tggaagaata agcttgtg     478

<210> SEQ ID NO 20
<211> LENGTH: 326
<212> TYPE: PRT
```

<213> ORGANISM: Saccharomyces cerevisiae

<400> SEQUENCE: 20

Met Ser Thr Asp Ser Thr Arg Tyr Pro Ile Gln Ile Glu Lys Ala Ser
1               5                   10                  15

Asn Asp Pro Thr Leu Leu Asn His Thr Cys Leu Arg Val Lys Asp
            20                  25                  30

Pro Ala Arg Thr Val Lys Phe Tyr Thr Glu His Phe Gly Met Lys Leu
        35                  40                  45

Leu Ser Arg Lys Asp Phe Glu Glu Ala Lys Phe Ser Leu Tyr Phe Leu
    50                  55                  60

Ser Phe Pro Lys Asp Asp Ile Pro Lys Asn Lys Asn Gly Glu Pro Asp
65                  70                  75                  80

Val Phe Ser Ala His Gly Val Leu Glu Leu Thr His Asn Trp Gly Thr
                85                  90                  95

Glu Lys Asn Pro Asp Tyr Lys Ile Asn Asn Gly Asn Glu Glu Pro His
            100                 105                 110

Arg Gly Phe Gly His Ile Cys Phe Ser Val Ser Asp Ile Asn Lys Thr
        115                 120                 125

Cys Glu Glu Leu Glu Ser Gln Gly Val Lys Phe Lys Lys Arg Leu Ser
    130                 135                 140

Glu Gly Arg Gln Lys Asp Ile Ala Phe Ala Leu Gly Pro Asp Gly Tyr
145                 150                 155                 160

Trp Ile Glu Leu Ile Thr Tyr Ser Arg Glu Gly Gln Glu Tyr Pro Lys
                165                 170                 175

Gly Ser Val Gly Asn Lys Phe Asn His Thr Met Ile Arg Ile Lys Asn
            180                 185                 190

Pro Thr Arg Ser Leu Glu Phe Tyr Gln Asn Val Leu Gly Met Lys Leu
        195                 200                 205

Leu Arg Thr Ser Glu His Glu Ser Ala Lys Phe Thr Leu Tyr Phe Leu
    210                 215                 220

Gly Tyr Gly Val Pro Lys Thr Asp Ser Val Phe Ser Cys Glu Ser Val
225                 230                 235                 240

Leu Glu Leu Thr His Asn Trp Gly Thr Glu Asn Asp Pro Asn Phe His
                245                 250                 255

Tyr His Asn Gly Asn Ser Glu Pro Gln Gly Tyr Gly His Ile Cys Ile
            260                 265                 270

Ser Cys Asp Asp Ala Gly Ala Leu Cys Lys Glu Ile Glu Val Lys Tyr
        275                 280                 285

Gly Asp Lys Ile Gln Trp Ser Pro Lys Phe Asn Gln Gly Arg Met Lys
    290                 295                 300

Asn Ile Ala Phe Leu Lys Asp Pro Asp Gly Tyr Ser Ile Glu Val Val
305                 310                 315                 320

Pro His Gly Leu Ile Ala
                325

<210> SEQ ID NO 21
<211> LENGTH: 319
<212> TYPE: PRT
<213> ORGANISM: Candida glabrata

<400> SEQUENCE: 21

Met Ser Tyr Pro His Lys Ile Ala Ala Ala His Asp Asp Pro Thr Leu
1               5                   10                  15

Met Phe Asn His Thr Cys Leu Arg Ile Lys Asp Pro Ala Lys Ser Ile

```
            20                  25                  30
Pro Phe Tyr Gln Lys His Phe Gly Met Glu Leu Leu Asn Lys Leu Asp
         35                  40                  45

Phe Pro Glu Met Lys Phe Ser Leu Phe Phe Leu Ser Phe Pro Lys Asp
     50                  55                  60

Asn Val Ala Lys Asn Ser Glu Gly Lys Asn Asp Val Phe Ser Thr Ser
 65                  70                  75                  80

Gly Ile Leu Glu Leu Thr His Asn Trp Gly Ser Glu Asn Asp Ala Asp
                 85                  90                  95

Phe Lys Ile Cys Asn Gly Asn Glu Glu Pro His Arg Gly Phe Gly His
                100                 105                 110

Ile Cys Phe Ser Tyr Ala Asp Ile Asn Ala Ala Cys Ser Lys Leu Glu
            115                 120                 125

Ala Glu Gly Val Ser Phe Lys Lys Arg Leu Thr Asp Gly Arg Met Lys
        130                 135                 140

Asp Ile Ala Phe Ala Leu Asp Pro Asp Gly Tyr Trp Ile Glu Leu Ile
145                 150                 155                 160

Arg Tyr Asp Arg Glu Asn Ser Pro Lys Lys Asp Val Gly Ser Arg Phe
                165                 170                 175

Asn His Thr Met Val Arg Val Lys Asp Pro Lys Ala Ser Leu Glu Phe
            180                 185                 190

Tyr Gln Asn Val Leu Gly Met Lys Leu Leu Arg Thr Ser Glu His Glu
        195                 200                 205

Ala Ala Lys Phe Thr Leu Tyr Phe Leu Gly Tyr Lys Val Ser Ser Glu
    210                 215                 220

Asp Asn Glu Phe Ser His Glu Gly Val Leu Glu Leu Thr His Asn Trp
225                 230                 235                 240

Gly Thr Glu Asn Glu Ala Asp Phe Lys Tyr His Asn Gly Asn Asp Lys
                245                 250                 255

Pro Gln Gly Tyr Gly His Ile Cys Val Ser Cys Lys Asp Pro Ala Lys
            260                 265                 270

Leu Cys Asn Glu Ile Glu Gln Thr Tyr Gly Asp Lys Ile Gln Trp Ala
        275                 280                 285

Pro Lys Phe Asn Gln Gly Lys Leu Lys Asn Ile Ala Phe Leu Lys Asp
    290                 295                 300

Pro Asp Gly Tyr Ser Ile Glu Val Val Pro His Gly Leu Ile Val
305                 310                 315

<210> SEQ ID NO 22
<211> LENGTH: 347
<212> TYPE: PRT
<213> ORGANISM: Zygosaccharomyces rouxii

<400> SEQUENCE: 22

Met Phe Ser Arg Val Phe Ser Arg Leu Gly Leu Ile Lys Gln His Ile
1               5                  10                  15

Arg Thr Met Ser Thr Lys Thr Ser Glu Ala Gln Tyr Tyr Thr Lys Lys
            20                  25                  30

Ile Ala Ser Ala Val Gly Asp Pro Ser Leu Arg Phe Asn His Thr Cys
        35                  40                  45

Leu Arg Ile Lys Asp Pro Ser Ala Ser Val Glu Phe Tyr Lys Lys His
    50                  55                  60

Phe Asn Met Thr Leu Leu Ser Lys Lys Asp Phe Pro Asp Met Lys Phe
65                  70                  75                  80
```

```
Ser Leu Tyr Phe Leu Val Met Thr Lys Glu Asn Leu Pro Lys Asn Glu
                85                  90                  95

Lys Gly Glu Asn Leu Val Phe Ala Asn Arg Gly Ile Leu Glu Leu Thr
            100                 105                 110

His Asn Trp Gly Thr Glu Ala Asp Pro Glu Tyr Lys Val Asn Asn Gly
        115                 120                 125

Asn Val Glu Pro His Arg Gly Phe Gly His Ile Cys Phe Ser Val Ala
    130                 135                 140

Asn Val Glu Ser Thr Cys Gln Arg Leu Glu Ser Glu Gly Val Lys Phe
145                 150                 155                 160

Gln Lys Arg Leu Val Asp Gly Arg Gln Lys Asn Ile Ala Phe Ala Leu
                165                 170                 175

Asp Pro Asp Gly Tyr Trp Ile Glu Leu Ile Gln Tyr Ile Asn Glu Ser
            180                 185                 190

Gly Glu Gly Pro Lys Thr Asp Leu Gly Asn Arg Phe Asn His Thr Met
        195                 200                 205

Val Arg Val Lys Asp Pro Val Lys Ser Leu Glu Phe Tyr Gln Asn Val
    210                 215                 220

Leu Gly Met Thr Leu His Arg Val Ser Glu His Ala Asn Ala Lys Phe
225                 230                 235                 240

Thr Leu Tyr Phe Leu Gly Tyr Asp Ile Pro Gln Gly Asp Ser Thr Gly
                245                 250                 255

Ser Ala Glu Thr Leu Leu Glu Leu Thr His Asn Trp Gly Thr Glu Asn
            260                 265                 270

Asp Pro Asp Phe His Tyr His Asn Gly Asn Ala Gln Pro Gln Gly Tyr
        275                 280                 285

Gly His Ile Cys Ile Thr Cys Lys Asp Pro Gly Ala Leu Cys Glu Glu
    290                 295                 300

Ile Glu Lys Lys Tyr Asn Glu Gln Val Val Trp Ser Pro Lys Trp Asn
305                 310                 315                 320

His Gly Lys Met Lys Asn Leu Ala Phe Ile Lys Asp Pro Asp Gly Tyr
                325                 330                 335

Ser Ile Glu Ile Val Pro Ala Glu Leu Val Leu
            340                 345

<210> SEQ ID NO 23
<211> LENGTH: 338
<212> TYPE: PRT
<213> ORGANISM: Kluyveromyces lactis

<400> SEQUENCE: 23

Met Phe Lys Glu Arg Leu Leu Asn Ile Leu Lys His Ile Arg Pro Met
1               5                   10                  15

Ser Thr Glu Thr Thr Ala Lys Tyr Tyr Pro Lys Ile Val Glu Ser Ala
            20                  25                  30

Gln Ala Asp Gln Ser Leu Lys Leu Asn His Thr Cys Phe Arg Val Lys
        35                  40                  45

Asp Pro Lys Val Thr Val Ala Phe Tyr Gln Glu Gln Phe Gly Met Lys
    50                  55                  60

Leu Leu Asp His Lys Lys Phe Pro Asp Met Lys Phe Asp Leu Tyr Phe
65                  70                  75                  80

Leu Ser Phe Pro Asn Lys Gln Phe Ser Asn Asn Ser Gln Gly Ala Ile
                85                  90                  95

Asp Val Phe Arg Glu Asn Gly Ile Leu Glu Leu Thr His Asn Tyr Gly
            100                 105                 110
```

Thr Glu Ser Asp Pro Ala Tyr Lys Val Asn Asn Gly Asn Glu Glu Pro
            115                 120                 125

His Arg Gly Phe Gly His Ile Cys Phe Ser Val Ser Asn Leu Glu Ala
        130                 135                 140

Glu Cys Glu Arg Leu Glu Ser Asn Gly Val Lys Phe Lys Lys Arg Leu
145                 150                 155                 160

Thr Asp Gly Ser Gln Arg Asn Ile Ala Phe Ala Leu Asp Pro Asn Gly
                165                 170                 175

Tyr Trp Ile Glu Leu Ile Gln Asn Asn Glu Ser Gly Glu Gly Asn Asn
            180                 185                 190

Tyr Lys Phe Asn His Thr Met Val Arg Val Lys Asp Pro Ile Lys Ser
        195                 200                 205

Leu Glu Phe Tyr Gln Asn Val Leu Gly Met Lys Ile Leu Asp Val Ser
210                 215                 220

Asp His Ser Asn Ala Lys Phe Thr Leu Tyr Phe Leu Gly Tyr Glu Asn
225                 230                 235                 240

Asp Gln Lys Gly Ile Ala Arg Gly Ser Arg Glu Ser Ile Leu Glu Leu
                245                 250                 255

Thr His Asn Trp Gly Thr Glu Asn Asp Pro Asp Phe Ala Tyr His Thr
            260                 265                 270

Gly Asn Thr Glu Pro Gln Gly Tyr Gly His Ile Cys Ile Ser Asn Lys
        275                 280                 285

Asp Pro Ala Thr Leu Cys Ala Glu Ile Glu Lys Leu Tyr Pro Asp Ile
290                 295                 300

Gln Trp Ser Pro Lys Phe Asn Gln Gly Lys Met Lys Asn Leu Ala Phe
305                 310                 315                 320

Ile Lys Asp Pro Asp Gly Tyr Ser Ile Glu Val Val Pro Tyr Gly Leu
                325                 330                 335

Gly Val

<210> SEQ ID NO 24
<211> LENGTH: 315
<212> TYPE: PRT
<213> ORGANISM: Candida magnoliae

<400> SEQUENCE: 24

Met Leu Gly Lys Val Ala Gln Lys Phe Leu Asn His Thr Cys Ile Arg
1               5                   10                  15

Ile Ala Asp Pro Ala Arg Ser Leu Ala Phe Tyr Glu Lys Asn Phe Gly
            20                  25                  30

Met Lys Leu Val Thr Gln Leu Asp Val Lys Glu Val Gly Phe Thr Leu
        35                  40                  45

Tyr Tyr Leu Gly Phe Thr Gly Pro Lys Ser Leu Tyr Lys Asp Thr Pro
    50                  55                  60

Trp Tyr Lys Arg Gly Gly Leu Leu Glu Leu Thr His Asn His Gly Ala
65                  70                  75                  80

Thr Pro Glu Asn Phe Glu Ala Asn Asn Gly Asn Lys Glu Pro His Arg
                85                  90                  95

Gly Phe Gly His Ile Cys Phe Ser Val Ser Asp Leu Glu Lys Thr Cys
            100                 105                 110

Glu Lys Leu Glu Gly Asn Gly Val Gly Phe Gln Lys Arg Leu Thr Asp
        115                 120                 125

Gly Arg Gln Lys Asn Ile Ala Phe Ala Leu Asp Pro Asp Gly Tyr Trp
    130                 135                 140

```
Ile Glu Leu Ile Arg Asn Gly Asn Glu Gly Ala Glu Ser Pro Glu Thr
145                 150                 155                 160

Cys Thr Thr Arg Phe Asn His Ser Met Ile Arg Val Lys Asp Lys Asp
                165                 170                 175

Ala Ala Leu Asp Phe Tyr Thr Asn Lys Leu Gly Met Thr Leu Val Asp
            180                 185                 190

Thr Ser Asp Phe Pro Glu Ala Lys Phe Thr Leu Phe Phe Leu Ser Phe
        195                 200                 205

Asp Pro Thr Ser Val Lys Glu Arg Ser Arg Gly Gly Thr Glu Gly Leu
    210                 215                 220

Ile Glu Leu Thr Tyr Asn Tyr Gly Ser Glu Gln Asp Val Asn Leu His
225                 230                 235                 240

Tyr His Asn Gly Asn Thr Asp Pro Gln Gly Phe Gly His Phe Gly Val
                245                 250                 255

Thr Val Pro Asp Ala Lys Ala Phe Leu Ser Glu Leu Glu Ser Lys Gly
            260                 265                 270

Val Arg Val Thr Lys Gln Leu Thr Glu Gly Lys Met Lys Phe Met Gly
        275                 280                 285

Phe Val Ser Asp Pro Asp Gly Tyr Leu Ile Glu Val Leu Pro Gln Arg
    290                 295                 300

Asp Phe Pro Lys Asp Leu Phe Ser Pro Ser Leu
305                 310                 315

<210> SEQ ID NO 25
<211> LENGTH: 32
<212> TYPE: DNA
<213> ORGANISM: Artificial Sequence
<220> FEATURE:
<223> OTHER INFORMATION: Forward primer of the GLO1 ORF
<220> FEATURE:
<221> NAME/KEY: source
<222> LOCATION: (1)..(32)
<223> OTHER INFORMATION: /organism="Artificial Sequence" /note="Forward
      primer of the GLO1 ORF" /mol_type="unassigned DNA"

<400> SEQUENCE: 25
agctgcagaa aatgtccact gatagtacac gc                                    32

<210> SEQ ID NO 26
<211> LENGTH: 35
<212> TYPE: DNA
<213> ORGANISM: Artificial Sequence
<220> FEATURE:
<223> OTHER INFORMATION: Reverse primer of the GLO1 ORF
<220> FEATURE:
<221> NAME/KEY: source
<222> LOCATION: (1)..(35)
<223> OTHER INFORMATION: /organism="Artificial Sequence" /note="Reverse
      primer of the GLO1 ORF" /mol_type="unassigned DNA"

<400> SEQUENCE: 26
aagtcgactt aggcaatcaa accatgagga acgac                                 35

<210> SEQ ID NO 27
<211> LENGTH: 981
<212> TYPE: DNA
<213> ORGANISM: Saccharomyces cerevisiae
<220> FEATURE:
<221> NAME/KEY: source
<222> LOCATION: (1)..(981)
<223> OTHER INFORMATION: /organism="Saccharomyces cerevisiae" /mol_type=
      "unassigned DNA"
```

<400> SEQUENCE: 27

```
atgtccactg atagtacacg ctatccaatt cagattgaga aagcctcgaa tgatccaacc    60
cttctgctta atcacacatg tttaagagtc aaggatccag caaggaccgt taagttctac   120
accgaacact tcggtatgaa gctattaagc agaaaggatt ttgaagaagc aaaatttagc   180
ttgtactttt taagctttcc aaaagacgac atacccaaaa ataagaatgg agagcctgat   240
gtttttagcg cacacggtgt cttagaacta actcacaatt ggggtactga aaaaaaccca   300
gactacaaga tcaacaacgg gaatgaggaa cctcatcgtg gatttgggca catctgtttt   360
tctgtatccg atatcaataa aacctgcgaa gagctagaat ctcagggtgt caaattcaag   420
aagagactct ctgaaggaag acagaaggac attgcgtttg ctttaggccc tgatggatac   480
tggattgagt tgatcacata ttctagagag ggtcaggaat acccaaaggg ctcagtaggt   540
aacaagttca atcataccat gattcgtatt aaaaacccaa cccggtcttt agaattctac   600
cagaatgtgt tgggcatgaa attattaaga actagtgagc acgaaagtgc aaaatttacg   660
ttatactttc ttggttatgg cgttccaaag accgacagcg ttttttcatg tgaaagtgtg   720
ttggagttaa ctcataattg gggaactgag aatgatccaa acttccacta tcataacggt   780
aactcagagc cccagggtta tggtcacatc tgcataagtt gtgatgacgc tggcgccctt   840
tgtaaagaaa ttgaagtgaa atacggcgat aagatccaat ggtctcctaa atttaaccaa   900
ggcagaatga agaatattgc cttttttgaag gatcctgatg ttattccat tgaagtcgtt   960
cctcatggtt tgattgccta a                                             981
```

<210> SEQ ID NO 28
<211> LENGTH: 22
<212> TYPE: DNA
<213> ORGANISM: Artificial Sequence
<220> FEATURE:
<223> OTHER INFORMATION: Forward primer homologous GLO1 expression
      cassettes
<220> FEATURE:
<221> NAME/KEY: source
<222> LOCATION: (1)..(22)
<223> OTHER INFORMATION: /organism="Artificial Sequence" /note="Forward
      primer homologous GLO1 expression cassettes" /mol_type="unassigned
      DNA"

<400> SEQUENCE: 28

```
aagcgacttc caatcgcttt gc                                             22
```

<210> SEQ ID NO 29
<211> LENGTH: 21
<212> TYPE: DNA
<213> ORGANISM: Artificial Sequence
<220> FEATURE:
<223> OTHER INFORMATION: Reverse primer homologous GLO1 expression
      cassettes
<220> FEATURE:
<221> NAME/KEY: source
<222> LOCATION: (1)..(21)
<223> OTHER INFORMATION: /organism="Artificial Sequence" /note="Reverse
      primer homologous GLO1 expression cassettes" /mol_type="unassigned
      DNA"

<400> SEQUENCE: 29

```
aaagcaaagg aaggagagaa c                                              21
```

<210> SEQ ID NO 30
<211> LENGTH: 70
<212> TYPE: DNA
<213> ORGANISM: Artificial Sequence
<220> FEATURE:
<223> OTHER INFORMATION: Forward primer HIS3 cassette, homologous GLO1 expression cassettes
<220> FEATURE:
<221> NAME/KEY: source
<222> LOCATION: (1)..(70)
<223> OTHER INFORMATION: /organism="Artificial Sequence" /note="Forward primer HIS3 cassette, homologous GLO1 expression cassettes" /mol_type="unassigned DNA"

<400> SEQUENCE: 30
ttgcccatcg aacgtacaag tactcctctg ttctctcctt cctttgcttt taactatgcg    60
gcatcagagc                                                           70

<210> SEQ ID NO 31
<211> LENGTH: 71
<212> TYPE: DNA
<213> ORGANISM: Artificial Sequence
<220> FEATURE:
<223> OTHER INFORMATION: Reverse primer HIS3 cassette, 3a flank INT1
<220> FEATURE:
<221> NAME/KEY: source
<222> LOCATION: (1)..(71)
<223> OTHER INFORMATION: /organism="Artificial Sequence" /note="Reverse primer HIS3 cassette, 3 flank INT1" /mol_type="unassigned DNA"

<400> SEQUENCE: 31
acttagtatg gtctgttgga aaggattgtg gcttcgcata caggctttct tcctgatgcg    60
gtattttctc c                                                         71

<210> SEQ ID NO 32
<211> LENGTH: 73
<212> TYPE: DNA
<213> ORGANISM: Artificial Sequence
<220> FEATURE:
<223> OTHER INFORMATION: Reverse primer INT1 5a flank, homologous GLO1 expression cassettes
<220> FEATURE:
<221> NAME/KEY: source
<222> LOCATION: (1)..(73)
<223> OTHER INFORMATION: /organism="Artificial Sequence" /note="Reverse primer INT1 5 flank, homologous GLO1 expression cassettes" /mol_type="unassigned DNA"

<400> SEQUENCE: 32
aaacgcctgt gggtgtggta ctggatatgc aaagcgattg gaagtcgctt agggtttcaa    60
agatccatac ttc                                                       73

<210> SEQ ID NO 33
<211> LENGTH: 74
<212> TYPE: DNA
<213> ORGANISM: Artificial Sequence
<220> FEATURE:
<223> OTHER INFORMATION: Forward primer INT1 3a flank, HIS3 cassette
<220> FEATURE:
<221> NAME/KEY: source
<222> LOCATION: (1)..(74)
<223> OTHER INFORMATION: /organism="Artificial Sequence" /note="Forward primer INT1 3 flank, HIS3 cassette" /mol_type="unassigned DNA"

<400> SEQUENCE: 33
agaaagcctg tatgcgaagc cacaatcctt tccaacagac catactaagt gaatgacctg    60
ttcccgacac tatg                                                      74

<210> SEQ ID NO 34
<211> LENGTH: 981
<212> TYPE: DNA

<213> ORGANISM: Artificial Sequence
<220> FEATURE:
<223> OTHER INFORMATION: GLO1 S. cerevisiae codon-pair optimized
      sequence
<220> FEATURE:
<221> NAME/KEY: source
<222> LOCATION: (1)..(981)
<223> OTHER INFORMATION: /organism="Artificial Sequence" /note="GLO1 S.
      cerevisiae codon-pair optimized sequence" /mol_type="unassigned
      DNA"

<400> SEQUENCE: 34

```
atgtccactg actctaccag atacccaatt caaattgaaa aggcctccaa cgacccaact      60
ctattattga accacacctg tttgagagtc aaggacccag ctagaactgt caaattctac    120
actgaacact tcggtatgaa attgttgtcc agaaaggact tgaagaagc taagttctct     180
ttgtacttct tgtctttccc aaaggatgac attccaaaga caagaacgg tgaaccagat     240
gttttctctg ctcacggtgt cttggaatta acccacaact ggggcactga aaagaaccca    300
gactacaaga tcaacaacgg taacgaagaa cctcaccgtg gtttcggtca tatctgtttc    360
tctgtttctg acatcaacaa gacctgtgaa gaattggaat ctcaaggtgt caagttcaag    420
aagagattat ctgaaggtcg tcaaaaggat atcgcctttg ctttgggtcc agatggttac    480
tggattgaat tgatcaccta ctccagagaa ggtcaagaat acccaaaggg ttccgttggt    540
aacaaattca ccacaccat gatcagaatc aagaacccaa ccagatcttt ggaattctac    600
caaaacgttt tgggtatgaa gttgttgaga acttctgaac acgaatctgc caagttcact    660
ttatacttct tgggttacgg tgttccaaag accgattctg tcttttcctg tgaatccgtt    720
ttggaattga cccataactg gggtactgaa aatgacccaa acttccacta ccacaatggt    780
aactctgaac tcaaggtta cggtcacatc tgtatctctt gtgatgatgc tggtgctttg    840
tgtaaggaaa ttgaagtcaa atacggtgac aagattcaat ggtccccaaa gttcaaccaa    900
ggtagaatga agaacattgc tttcttgaaa gacccagacg ttactccat cgaagttgtt    960
ccacacggtt tgatcgctta a                                             981
```

<210> SEQ ID NO 35
<211> LENGTH: 960
<212> TYPE: DNA
<213> ORGANISM: Artificial Sequence
<220> FEATURE:
<223> OTHER INFORMATION: GLO1 C. glabrata codon-pair optimized sequence
<220> FEATURE:
<221> NAME/KEY: source
<222> LOCATION: (1)..(960)
<223> OTHER INFORMATION: /organism="Artificial Sequence" /note="GLO1 C.
      glabrata codon-pair optimized sequence" /mol_type="unassigned DNA"

<400> SEQUENCE: 35

```
atgtcttacc cacacaagat tgctgctgcc cacgatgacc caactttgat gttcaaccac     60
acctgtttga gaatcaagga cccagctaag tccattccat tttaccaaaa gcatttcggt   120
atggaattgt tgaacaaatt ggacttccca gaaatgaaat ctccttgtt tttcttatct    180
ttcccaaagg acaacgttgc caagaactct gaaggtaaga acgatgtctt ctccacttct   240
ggtatcttgg aattgaccca caactggggt tctgaaaacg atgctgattt caagatctgt   300
aacggtaacg aagaaccaca ccgtggtttc ggtcacatct gtttctctta cgctgatatc   360
aacgctgctt gttccaaatt ggaagctgaa ggtgtttctt tcaagaagag attgaccgat   420
ggtagaatga aggatatcgc ctttgctttg gacccagacg ttactggat cgaattaatc    480
agatacgaca gagaaaactc tccaaagaag gacgtcggtt ccagattcaa ccataccatg   540
```

```
gtcagagtta aggacccaaa ggcttctttg gaattctacc aaaacgttct aggtatgaaa      600
ttgttgagaa cctctgaaca cgaagctgcc aagttcactt tgtacttctt aggttacaag      660
gtttcctctg aagacaacga attctctcac gaaggtgtct tagaattgac tcataactgg      720
ggtactgaaa tgaagctgac cttcaaatac acaacggta  atgacaagcc acaaggttac      780
ggtcacattt tgtgtctcctg taaggatcca gccaagttgt gtaacgaaat tgaacaaacc      840
tacggtgaca agatccaatg ggctccaaag ttcaaccaag gtaaattgaa gaacattgct      900
ttcttgaagg accctgatgg ttactccatc gaagttgttc cacacggttt gattgtataa      960
```

<210> SEQ ID NO 36
<211> LENGTH: 948
<212> TYPE: DNA
<213> ORGANISM: Artificial Sequence
<220> FEATURE:
<223> OTHER INFORMATION: GLO1 C. magnoliae codon-pair optimized sequence
<220> FEATURE:
<221> NAME/KEY: source
<222> LOCATION: (1)..(948)
<223> OTHER INFORMATION: /organism="Artificial Sequence" /note="GLO1 C. magnoliae codon-pair optimized sequence" /mol_type="unassigned DNA"

<400> SEQUENCE: 36

```
atgttgggta aggttgctca aaagttcttg aaccacacct gtatcagaat tgctgaccca       60
gctcgttctt tggctttcta cgaaaagaac tttggtatga aattggttac tcaattggat      120
gtcaaggaag tcggtttcac tttgtactac ttgggtttca ccggtccaaa gtctttatac      180
aaggacactc catggtacaa gagaggtggt ctattggaat tgactcacaa ccatggtgcc      240
actccagaaa actttgaagc taacaatggt aacaaggaac cacacagagg ttttggtcac      300
atctgtttct ccgtttctga tttggaaaag acctgtgaaa aattggaagg taacggtgtc      360
ggtttccaaa agagattgac cgatggtaga caaaagaaca ttgcctttgc tttggaccca      420
gacggttact ggattgaatt gatcagaaac ggtaacgaag tgctgaatc  tccagaaacc      480 tgtaccacca gattcaacca ctccatgatc agagttaagg acaaggacgc tgctttggat      540
ttctacacca acaaattggg tatgactttg gttgacacct tgacttccc  agaagccaag      600 ttcactttat tcttcttgtc tttcgaccca acttccgtca aggaaagatc cagaggtggt      660
actgaaggtt aatcgaatt gacctacaac tacggttctg aacaagatgt caacttgcac      720
taccacaacg gtaacactga cccacaaggt ttcggtcact cggtgtcac cgttccagat      780 gctaaggctt tcttgtccga attggaatcc aagggtgtcc gtgtcaccaa gcaattgact      840
gaaggtaaga tgaaattcat gggtttcgtt tctgacccag atggttactt gattgaagtt      900
ttgcctcaaa gagatttccc aaaggactta ttctctccat cgctctaa                   948
```

<210> SEQ ID NO 37
<211> LENGTH: 1017
<212> TYPE: DNA
<213> ORGANISM: Artificial Sequence
<220> FEATURE:
<223> OTHER INFORMATION: GLO1 K. lactis codon-pair optimized sequence
<220> FEATURE:
<221> NAME/KEY: source
<222> LOCATION: (1)..(1017)
<223> OTHER INFORMATION: /organism="Artificial Sequence" /note="GLO1 K. lactis codon-pair optimized sequence" /mol_type="unassigned DNA"

<400> SEQUENCE: 37

```
atgttcaagg aaagattatt gaacatcttg aagcacatca gaccaatgtc tactgaaacc       60
```

```
accgccaagt actacccaaa gattgtcgaa tctgctcaag ctgaccaatc tttgaaatta      120
aaccatacct gtttcagagt caaggatcca aaggttaccg ttgctttcta ccaagaacaa      180
tttggtatga aattgttgga ccacaagaag ttcccagaca tgaagttcga cttgtacttc      240
ttgtctttcc caaacaagca attctccaac aactctcaag gtgccattga tgttttcaga      300
gaaaacggta tcttggaatt gacccacaac tacggtactg aatctgaccc agcttacaag      360
gtcaacaacg gtaacgaaga accacaccgt ggtttcggtc acatctgttt ctccgtttcc      420
aacttggaag ctgaatgtga agattggaa tccaacggtg tcaagttcaa gaagagattg       480 accgatggt ctcaaagaaa cattgctttc gctttggacc caaacggtta ctggattgaa       540
ttgatccaaa caacgaatc tggtgaaggt aacaactaca aattcaacca caccatggtt       600
cgtgttaagg acccaatcaa atctttgaa ttctaccaaa acgtcttggg tatgaagatc       660
ttggatgtct ctgaccattc caatgctaag ttcactttat acttcttggg ttacgaaaat      720
gaccaaaagg gtattgccag aggttccaga gaatccatct tagaattgac tcacaactgg      780
ggtactgaaa acgacccaga ttttgcttac cacaccggta acactgaacc tcaaggttac      840
ggtcacattt gtatctctaa caaagaccca gctactctat gtgctgaaat tgaaaagttg      900
tacccagata tccaatggtc cccaaagttc aaccaaggta agatgaagaa cttggccttt     960
atcaaggacc cagatggtta ctctattgaa gttgttccat acggtttagg ggtgtaa       1017
```

<210> SEQ ID NO 38
<211> LENGTH: 1044
<212> TYPE: DNA
<213> ORGANISM: Artificial Sequence
<220> FEATURE:
<223> OTHER INFORMATION: GLO1 Z. rouxii codon-pair optimized sequence
<220> FEATURE:
<221> NAME/KEY: source
<222> LOCATION: (1)..(1044)
<223> OTHER INFORMATION: /organism="Artificial Sequence" /note="GLO1 Z. rouxii codon-pair optimized sequence" /mol_type="unassigned DNA"

<400> SEQUENCE: 38

```
atgttctccc gtgttttctc cagattaggt ttgatcaagc aacacatcag aaccatgtcc       60
accaagactt ctgaagccca atactacacc aagaagattg cttctgctgt cggtgaccca      120
tctttgcgtt tcaaccacac ctgtttgaga atcaaggacc catctgcttc cgtcgaattc      180
tacaagaagc acttcaacat gactttgttg tccaagaagg acttcccaga catgaaattc      240
tctctatact ttttggttat gaccaaggaa aacttgccaa gaacgaaaa gggtgaaaac      300 ttggttttg ctaacagagg tatcttggaa ttaacccaca ctggggcac tgaagctgac       360 ccagaataca aggtcaacaa tggtaacgtt gaacctcaca gaggtttcgg tcacatttgt      420
ttctctgttg ctaacgtcga atccacttgt caaagattgg aatctgaagg tgttaagttc      480
caaaagagat tagtcgatgg tagacaaaag aacattgcct tgctttggaa cccagatggt      540
tactggatcg aattgattca atacatcaac gaatctggtg aaggtccaaa gaccgatttg      600
ggtaacagat caaccatac catggttaga gtcaaggatc cagttaagtc tttggaattc       660
taccaaaatg tcttaggtat gactttgcac agagttctg aacacgctaa cgccaaattc       720
actttgtact tcttgggtta cgatatccca caaggtgact ctactggttc tgctgaaact      780 tgttggaat tgacccataa ctggggtact gaaaacgacc cagatttcca ctaccacaac      840
ggtaacgccc aaccacaagg ttacggtcac atctgtatca cctgtaagga cccaggtgct      900
ttgtgtgaag aaattgaaaa gaaatacaac gaacaagttg tctggtcccc aaaatggaac      960
```

```
cacggtaaga tgaagaactt ggctttcatc aaagatccag acggttactc cattgaaatt    1020
gttccagctg aattggtctt ataa                                           1044
```

US 10,273,507 B2

CELLS WITH IMPROVED PENTOSE CONVERSION

FIELD OF THE INVENTION

The invention is directed to cells with improved pentose conversion. More specifically the invention relates to cells that have improved conversion of xylose and/or L-arabinose. The cells are useful for the production of fermentation products, for instance for the production of ethanol from sugars that are derived from lignocellulosic material.

BACKGROUND OF THE INVENTION

Large-scale consumption of traditional, fossil fuels (petroleum-based fuels) in recent decades has contributed to high levels of pollution. This, along with the realisation that the world stock of fossil fuels is not unlimited and a growing environmental awareness, has stimulated new initiatives to investigate the feasibility of alternative fuels such as ethanol, which is a particulate-free burning fuel source that releases less $CO_2$ than unleaded gasoline on a per liter basis.

Although biomass-derived ethanol may be produced by the fermentation of hexose sugars obtained from many different sources, the substrates typically used for commercial scale production of fuel alcohol, such as cane sugar and corn starch, are expensive. Increases in the production of fuel ethanol will therefore require the use of lower-cost feedstocks.

Currently, only lignocellulosic feedstock derived from plant biomass is available in sufficient quantities to substitute the crops currently used for ethanol production. In most lignocellulosic material, the second-most-common sugar, after glucose, is xylose. Also L-arabinose is a sugar derived from some lignocellulosic material. Thus, for an economically feasible fuel production process, both hexose and pentose sugars must be fermented to form ethanol. The yeast *Saccharomyces cerevisae* is robust and well adapted for ethanol production, but it is unable to produce ethanol using xylose as a carbon source. There is therefore a need for an organism possessing these properties so as to enable the commercially-viable production of ethanol from lignocellulosic feedstocks. Xylose isomerase from the anaerobic fungus *Piromyces* Sp.E2 was introduced in *S. cerevisiae* and high levels of enzyme activities were observed enabling this strain to grow anaerobically and produce ethanol from xylose (WO2003/062430 and WO06/009434). Such yeast strains for the first time provided specific rates of xylose consumption and ethanol formation that are compatible with ethanol production at a commercial scale.

However, it is still desirable to improve pentose conversion and to reduce fermentation time.

SUMMARY OF THE INVENTION

An object of the invention is to provide cells with improved pentose conversion. Another object of the invention is to provide recombinant strains that have improved conversion of xylose and/or L-arabinose. Another object is to provide strains that have improved conversion of xylose and/or L-arabinose in the presence of glucose. Another object is to reduce the fermentation time in fermentation of pentose and hexose comprising sugar mixtures.

One or more of these objects are attained according to the invention. According to the present invention, there is provided a cell which constitutively expresses a heterologous or homologous polypeptide, having the amino acid sequence of SEQ ID NO: 20 or an amino acid sequence encoded by the nucleotide sequence of SEQ ID NO: 27, or a variant thereof having an amino acid sequence having at least 45% sequence identity to SEQ ID NO: 20.

The cells according to the examples have improved pentose conversion and lead to reduced fermentation times in fermentation of pentose and hexose comprising sugar mixtures. In an embodiment the polypeptide has glyoxalase activity.

The invention also provides:
- a process for producing a fermentation product which process comprises fermenting a medium containing a source of xylose and or L-arabinose with a cell of the invention such that the cell ferments xylose and/or L-arabinose to the fermentation product;
- the use of a cell of the invention in a process for the production of a fermentation product.

BRIEF DESCRIPTION OF THE SEQUENCE LISTING

Figure 1:
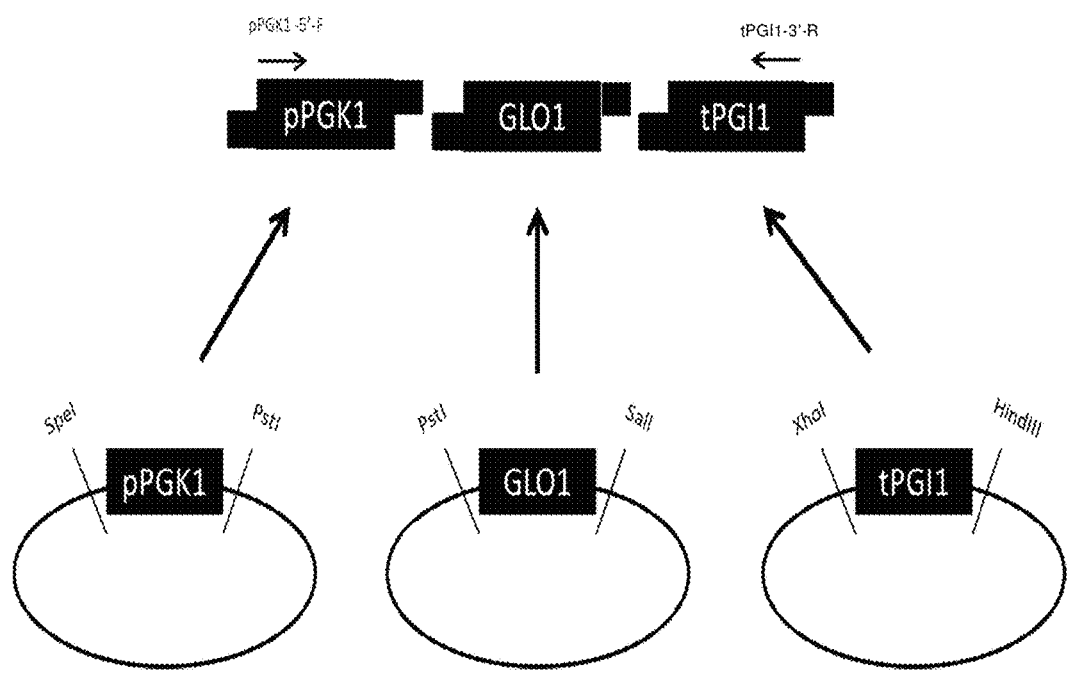
FIG. 1: Graph of GLO1 expression cassette with the PGK1 promoter and PGI1 terminator.

SEQ ID NO 1: Forward primer PGK1 promoter;
SEQ ID NO 2: Reverse primer PGI1 terminator;
SEQ ID NO 3: Forward primer ACT1 gene;
SEQ ID NO 4: Reverse primer ACT1 gene;
SEQ ID NO 5: Forward primer GLO1 gene, Q-PCR;
SEQ ID NO 6: Reverse primer GLO1 gene, Q-PCR;
SEQ ID NO 7: Forward primer ALG9 gene, Q-PCR;
SEQ ID NO 8: Reverse primer ALG9 gene, Q-PCR;
SEQ ID NO 9: Forward primer UBC6 gene, Q-PCR;
SEQ ID NO 10: Reverse primer UBC6 gene, Q-PCR;
SEQ ID NO 11: Forward primer HIS3 cassette, 5' flank INT1;
SEQ ID NO 12: Reverse primer GLO1 cassette, 3' flank INT1;
SEQ ID NO 13: Reverse primer HIS3 cassette, 3' flank INT1;
SEQ ID NO 14: Forward primer 5' flank INT1;
SEQ ID NO 15: Reverse primer 5' flank INT1;
SEQ ID NO 16: Forward primer 3' flank INT1;
SEQ ID NO 17: Reverse primer 3' flank INT1;
SEQ ID NO 18: Nucleotide sequence 5' flank of integration site INT1;
SEQ ID NO 19: Nucleotide sequence 3' flank of integration site INT1;
SEQ ID NO 20: Protein sequence of GLO1 from *S. cerevisiae*;
SEQ ID NO 21: Protein sequence of GLO1 from *Candida glabrata*;
SEQ ID NO 22: Protein sequence of GLO1 from *Zygosaccharomyces rouxii*;
SEQ ID NO 23: Protein sequence of GLO1 from *Kluyveromyces lactis*;
SEQ ID NO 24: Protein sequence of GLO1 from *Candida magnolia*;
SEQ ID NO 25: Forward primer of the GLO1 ORF;
SEQ ID NO 26: Reverse primer of the GLO1 ORF;
SEQ ID NO 27: Nucleotide sequence of GLO1 from *S. cerevisiae*;
SEQ ID NO 28: Forward primer of the homologous GLO1 expression cassettes (including promoter and terminator);
SEQ ID NO 29: Reverse primer of the homologous GLO1 expression cassettes (including promoter and terminator);
SEQ ID NO 30: Forward primer of the HIS3 cassette, consisting of 20 nucleotides and a tail of 50 nucleotides on the 5'-end, identical to the 50 nucleotides of the 3'-end of the homologous GLO1 expression cassettes;
SEQ ID NO 31: Reverse primer of the HIS3 cassette, consisting of 21 nucleotides and a tail of 50 nucleotides on the 5'-end, identical to the 50 nucleotides of the 5'-end of the 3' 500 bp INT1 flank;
SEQ ID NO 32: Reverse primer of the 5' 500 bp INT1 flank, consisting of 23 nucleotides and a tail of 50 nucleotides on the 5'-end, identical to the 50 nucleotides of the 5'-end of the homologous GLO1 expression cassettes;
SEQ ID NO 33: Forward primer of the 3' 500 bp INT1 flank, consisting of 24 nucleotides and a tail of 50 nucleotides on the 5'-end, identical to the 50 nucleotides of the 3'-end of the HIS3 expression cassette;
SEQ ID NO 34: Codon pair optimized nucleotide sequence of GLO1 from *S. cerevisiae*;
SEQ ID NO 35: Codon pair optimized nucleotide sequence of GLO1 from *Candida glabrata*;
SEQ ID NO 36: Codon pair optimized nucleotide sequence of GLO1 from *Candida magnolia*;
SEQ ID NO 37: Codon pair optimized nucleotide sequence of GLO1 from *Kluyveromyces lactis*;
SEQ ID NO 38: Codon pair optimized nucleotide sequence of GLO1 from *Zygosaccharomyces rouxii*.

DETAILED DESCRIPTION OF THE INVENTION

Throughout the present specification and the accompanying claims the words "comprise" and "include" and variations such as "comprises", "comprising", "includes" and "including" are to be interpreted inclusively. That is, these words are intended to convey the possible inclusion of other elements or integers not specifically recited, where the context allows.

According to the invention, the cell may comprises a glyoxalase activity, preferebaly a glyoxalase I acitivity. Glyoxalase1 (GLO1) is a gene that encodes that encodes glyoxalase I (EC 4.4.1.5), which is involved in methylglyoxal catabolism (2). Methylglyoxal is a toxic compound formed as a by-product of glycolysis.

Alternative names for glyoxalase are for instance lactoyl-glutathione lyase, aldoketomutase, ketone-aldehyde mutase, methylglyoxalase, S-D-lactoylglutathione methylglyoxal lyase.

One method of methylglyoxal catabolism comprises a glyoxalase system in which methylglyoxal is condensed with glutathione by Glo1p to produce S-D-lactoylglutathione. This glutathione thiolester is then hydrolyzed to lactic acid and glutathione by glyoxalase II (Glo2p and Glo4p). GLO1 expression is induced by methylglyoxal and is specifically induced by osmotic stress in a high osmolarity glycerol (Hog1p)-mitogen-activated protein (MAP) kinase-dependent manner (1).

Deletion of GLO1 results in hypersensitivity to methylglyoxal. In *S. cerevisiae*, glyoxalase I (Glo1p) is native and occurs is a monomer. This system shows many of the typical features of the enzymes that dispose of endogenous toxins. Firstly, in contrast to the amazing substrate range of many of the enzymes involved in xenobiotic metabolism, it shows narrow substrate specificity. Secondly, intracellular thiols are required as part of its enzymatic mechanism and thirdly, the system acts to recycle reactive metabolites back to a form which may be useful to cellular metabolism.

In an embodiment, the invention relates to a cell which expresses a glyoxalase, wherein the amino acid sequence of the glyoxalase has at least 45% identity to the amino acid sequence set out in SEQ ID NO: 20 and wherein the nucleotide sequence is constitutively integrated homologous or heterologous to the cell.

Amino Acid/Polynucleotide Sequence

The cell of the invention is defined with reference to a protein having the amino acid sequence of SEQ ID NO: 20 or a sequence having at least 45% sequence identity thereto. In an embodiment, the protein has at least about 50%, at least about 55%, at least about 60%, at least about 65%, at least about 70%, at least about 80%, at least about 90%, at least about 94%, at least about 95%, at least about 96%, at least about 97%, at least about 98% or at least about 99% sequence identity with the amino acid sequence of SEQ ID NO: 20.

In an embodiment, the cell comprises and/or expresses a polypeptide having amino acids H, E, H and E corresponding to the positions H25, E89, H269 and E318 and/or H185, E242, H117 and E163 in SEQ ID NO: 20. In an embodiment, the cell comprises and/or expresses a polypeptide having a fragment (E,s,d)-L-X-(H,Y)-(N,s) corresponding to the fragment E242-L243-X-H245-N246 in SEQ ID NO: 20. In an embodiment the cell comprises and/or expresses a polypeptide having a fragment G-(F,Y)-G-H corresponding to the fragment G266-Y267-G268-H269 in SEQ ID NO: 20. In an embodiment the cell comprises and/or expresses a polypeptide having a fragment G-X(6)-(F,i)-X(2,3)-D-X(3)-Y corresponding to the fragment G301-X(6)-F308-X(2)-D311-X(3)-Y315 in SEQ ID NO: 20.

In the above, amino acids are indicated with one letter code. X is any amino acid; (X,Y) aminoacid X or Y; X(y) an y number aminoacids X and X(y,z) an y or z number of aminoacids X. Small letter code indicates an amino acid that has minor occurrence.

In an embodiment the cell comprises and/or expresses a polypeptide having glyoxalase activity.

A cell according to the present invention may comprise a nucleotide sequence encoding a glyoxalase having the nucleotide sequence of SEQ ID NO: 27 or a sequence which has at least about 50%, at least about 55%, at least about 60%, at least about 65%, at least about 70%, at least about 75%, preferably at least about 80%, at least about 85%, at least about 90%, at least about 92%, at least about 93%, at least about 94%, at least about 95%, at least about 96%, at least about 97%, at least about 98% or at least about 99% or at least 75%, at least 80%, at least 85%, at least 90%, at least 92%, at least 93%, at least 94%, at least 95%, at least 96%, at least 97%, at least 98% or at least 99% sequence identity with the nucleic acid sequence set out in SEQ ID NO: 27.

The invention therefore provides cells with polynucleotide sequences comprising the gene encoding the glyoxalase polypeptide, as well as its coding sequence.

The polynucleotides of the invention may be isolated or synthesized. The glyoxalase polypeptides and glyoxalase polynucleotides herein may be synthetic polypeptides, respectively polynucleotides. The synthetic polynucleotides may be optimized in codon use, preferably according to the methods described in WO2006/077258 and/or PCT/EP2007/055943, which are herein incorporated by reference. PCT/EP2007/055943 addresses codon-pair optimization.

The term refers to a polynucleotide molecule, which is a ribonucleic acid (RNA) or deoxyribonucleic acid (DNA) molecule, either single stranded or double stranded. A polynucleotide may either be present in isolated form, or be comprised in recombinant nucleic acid molecules or vectors, or be comprised in a host cell.

The word "polypeptide" is used herein for chains containing more than seven amino acid residues. All oligopeptide and polypeptide formulas or sequences herein are written from left to right and in the direction from amino terminus to carboxy terminus. The one-letter code of amino acids used herein is commonly known in the art.

By "isolated" polypeptide or protein is intended a polypeptide or protein removed from its native environment. For example, recombinantly produced polypeptides and proteins expressed in host cells are considered isolated for the purpose of the invention as are native or recombinant polypeptides which have been substantially purified by any suitable technique such as, for example, the single-step purification method disclosed in Smith and Johnson, Gene 67:31-40 (1988).

The polynucleotides of the present invention, such as a polynucleotide encoding the glyoxalase polypeptide can be isolated or synthesized using standard molecular biology techniques and the sequence information provided herein.

The polynucleotide encoding the glyoxalase polypeptide of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis.

Enzyme Kinetics

Enzymes are protein catalysts that, like all catalysts, speed up the rate of a chemical reaction without being used up in the process.

They achieve their effect by temporarily binding to the substrate and, in doing so, lowering the activation energy needed to convert it into a product.

The rate at which an enzyme works is influenced by several factors, e.g., the concentration of substrate molecules (designated [S], expressed in units of molarity), the temperature, the presence of inhibitors (competitive inhibitors binding to the same site as the substrate or noncompetitive inhibitors binding to another site on the enzyme reducing its catalytic power), pH, and the like.

Enzyme kinetics studies and describes the rate at which enzymes work. There are many methods of measurement. The enzyme converts substrate into product at an initial rate that is approximately linear for a short period after the start of the reaction. As the reaction proceeds and substrate is consumed, the rate continuously slows, as substrate is still present at saturating levels. To measure the initial (and maximal) rate, enzyme assays are typically carried out while the reaction has progressed only a few percent towards total completion. The length of the initial rate period depends amongst others on the assay conditions.

The study of enzyme kinetics is important for two basic reasons. Firstly, it helps to explain how enzymes work, and secondly, it helps to predict how enzymes behave in living organisms. The kinetic constants, Km and Vmax, are critical to attempts to understand how enzymes work together to control metabolism.

The Michaelis constant Km is experimentally defined as the concentration at which the rate of the enzyme reaction is half Vmax. Vmax is the maximal velocity at which the enzyme catalyzes the reaction: as [S] gets higher, the enzyme becomes saturated with substrate and the rate reaches Vmax, the enzyme's maximum rate.

Km is (roughly) an inverse measure of the affinity or strength of binding between the enzyme and its substrate. The lower the Km value (in mM), the greater the affinity, hence the lower the concentration of substrate needed to achieve a given rate.

The Host Cell

The host cell may be any host cell suitable for production of a useful product. A host cell may be any suitable cell, such as a prokaryotic cell, such as a bacterium, or a eukaryotic cell. Typically, the cell will be a eukaryotic cell, for example a yeast or a filamentous fungus. The host cell is capable of converting one or more pentose sugar, such as L-arabinose or xylose into fermentation product.

The host cell may be a bacterium. In an embodiment the bacterium is genetically engineered for pentose conversion. In an embodiment the bacterium is not *Escherichia coli* (*E. coli*). An example of a bacterium that is a suitable host for the application of the invention is genetically engineered *Zymomonas mobilis*. Such strain is for example described in Yanna et al, *Appl Microbiol Biotechnol.* 2012 June; 94(6): 1667-78.

The host for the invention may be (genetically engineered) yeast. Genetic engineering is hereinafter described in detail. Yeasts are herein defined as eukaryotic microorganisms and include all species of the subdivision Eumycotina (Alexopoulos, C. J., 1962, In: Introductory Mycology, John Wiley & Sons, Inc., New York) that predominantly grow in unicellular form.

Yeasts may either grow by budding of a unicellular thallus or may grow by fission of the organism. A preferred yeast as a transformed host cell may belong to the genera *Saccharomyces, Kluyveromyces, Candida, Pichia, Schizosaccharomyces, Hansenula, Kloeckera, Schwanniomyces* or *Yarrowia*. Preferably the yeast is one capable of anaerobic fermentation, more preferably one capable of anaerobic alcoholic fermentation.

In one embodiment the host cell is yeast.

Preferably the host is an industrial host, more preferably an industrial yeast. An industrial host and industrial yeast cell may be defined as follows. The living environments of yeast cells in industrial processes are significantly different from that in the laboratory. Industrial yeast cells must be able to perform well under multiple environmental conditions which may vary during the process. Such variations include change in nutrient sources, pH, ethanol concentration, temperature, oxygen concentration, etc., which together have potential impact on the cellular growth and ethanol production of *Saccharomyces cerevisiae*. Under adverse industrial conditions, the environmental tolerant strains should allow robust growth and production. Industrial yeast strains are generally more robust towards these changes in environmental conditions which may occur in the applications they are used, such as in the baking industry, brewing industry, wine making and the ethanol industry. Examples of industrial yeast (*S. cerevisiae*) are Ethanol Red® (Fermentis) Fermiol® (DSM) and Thermosacc® (Lallemand).

In an embodiment the host is inhibitor tolerant. Inhibitor tolerant host cells may be selected by screening strains for growth on inhibitors containing materials, such as illustrated in Kadar et al, Appl. Biochem. Biotechnol. (2007), Vol. 136-140, 847-858, wherein an inhibitor tolerant *S. cerevisiae* strain ATCC 26602 was selected.

Transformation

The polynucleotides according to the invention may be expressed in a suitable host. Therefore standard transformation techniques may be used.

The invention further relates to a nucleic acid construct comprising the polynucleotide as described before, e.g. a vector.

Another aspect of the invention thus pertains to vectors, including cloning and expression vectors, comprising a polynucleotide of the invention encoding a glyoxalase polypeptide protein or a functional equivalent thereof and methods of growing, transforming or transfecting such vectors in a suitable host cell, for example under conditions in which expression of a glyoxalase of the invention occurs. As used herein, the term "vector" refers to a nucleic acid molecule capable of transporting another nucleic acid to which it has been linked.

Polynucleotides of the invention can be incorporated into a recombinant replicable vector, for example a cloning or expression vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells are described below.

It will be appreciated by those skilled in the art that the design of the expression vector can depend on such factors as the choice of the host cell to be transformed, the level of expression of protein desired, etc. The vectors, such as expression vectors, of the invention can be introduced into host cells to thereby produce proteins or peptides, encoded by nucleic acids as described herein. The vectors, such as recombinant expression vectors, of the invention can be designed for expression of glyoxalase polypeptide proteins in prokaryotic or eukaryotic cells.

For example, glyoxalase polypeptides can be expressed in bacterial cells such as *E. coli*, insect cells (using baculovirus expression vectors), filamentous fungi, yeast cells or mammalian cells. Suitable host cells are discussed further in Goeddel, *Gene Expression Technology: Methods in Enzymology* 185, Academic Press, San Diego, Calif. (1990). Representative examples of appropriate hosts are described hereafter.

Appropriate culture mediums and conditions for the above-described host cells are known in the art.

For most filamentous fungi and yeast, the vector or expression construct is preferably integrated in the genome of the host cell in order to obtain stable transformants. However, for certain yeasts also suitable episomal vectors are available into which the expression construct can be incorporated for stable and high level expression, examples thereof include vectors derived from the 2p and pKD1 plasmids of *Saccharomyces* and *Kluyveromyces*, respectively, or vectors containing an AMA sequence (e.g. AMA1 from *Aspergillus*). In case the expression constructs are integrated in the host cells genome, the constructs are either integrated at random loci in the genome, or at predetermined target loci using homologous recombination, in which case the target loci preferably comprise a highly expressed gene.

Accordingly, expression vectors useful in the present invention include chromosomal-, episomal- and virus-derived vectors e.g., vectors derived from bacterial plasmids, bacteriophage, yeast episome, yeast chromosomal elements, viruses such as baculoviruses, papova viruses, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids.

The vector may further include sequences flanking the polynucleotide giving rise to RNA which comprise sequences homologous to eukaryotic genomic sequences or viral genomic sequences. This will allow the introduction of the polynucleotides of the invention into the genome of a host cell.

An integrative cloning vector may integrate at random or at a predetermined target locus in the chromosome(s) of the host cell into which it is to be integrated.

The vector system may be a single vector, such as a single plasmid, or two or more vectors, such as two or more plasmids, which together contain the total DNA to be introduced into the genome of the host cell.

The vector may contain a polynucleotide of the invention oriented in an antisense direction to provide for the production of antisense RNA.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, transduction, infection, lipofection, cationic lipid-mediated transfection or electroporation. Suitable methods for transforming or transfecting host cells can be found in Sambrook, et al. (*Molecular Cloning: A Laboratory Manual*, $2^{nd}$, ed. Cold Spring Harbor Laboratory, Cold Spring Harbor Laboratory Press, Cold Spring Harbor, N.Y., 1989), Davis et al., *Basic Methods in Molecular Biology* (1986) and other laboratory manuals.

The polynucleotide according to the invention is constitutively expressed. Herein, the term "constitutive", usually with respect to the host cell, means that the polynucleotide is present not (or not only) as it is present naturally in the host. In that sense it can also be explained as that the polynucleotide is brought into the cell by human intervention. A characteristic of constitutive expressed gene is that the gene is transcribed continuously, irrespective of the growth conditions, such as the carbon source or the growth phase of the cells. The polynucleotide may be heterologous to the genome of the host cell. The term "heterologous", usually with respect to the host cell, means that the polynucleotide does not naturally occur in the genome of the host cell or that the polypeptide is not naturally produced by that cell.

The polynucleotide may be homologous to the genome of the host cell. The term "homologous", usually with respect to the host cell, means that the polynucleotide naturally occurs in the genome of the host cell or that the polypeptide is naturally produced by that cell.

In another embodiment, the invention features cells, e.g., transformed host cells or recombinant host cells that contain a nucleic acid encompassed by the invention. A "transformed cell" or "recombinant cell" is a cell into which (or into an ancestor of which) has been introduced, by means of recombinant DNA techniques, a nucleic acid according to the invention. Both prokaryotic and eukaryotic cells are included, e.g., bacteria, fungi, yeast, and the like, especially preferred are yeast cells including e.g. *Saccharomyces*, for example *Saccharomyces cerevisiae*.

A host cell can be chosen that modulates the expression of the inserted sequences, or modifies and processes the gene product in a specific, desired fashion. Such modifications (e.g., glycosylation) and processing (e.g. cleavage) of protein products may facilitate optimal functioning of the protein.

Various host cells have characteristic and specific mechanisms for post-translational processing and modification of proteins and gene products. Appropriate cell lines or host systems familiar to those of skill in the art of molecular biology and/or microbiology can be chosen to ensure the desired and correct modification and processing of the foreign protein expressed. To this end, eukaryotic host cells that possess the cellular machinery for proper processing of the primary transcript, glycosylation, and phosphorylation of the gene product can be used. Such host cells are well known in the art.

If desired, a cell as described above may be used to in the preparation of a polypeptide according to the invention. Such a method typically comprises cultivating a host cell (e.g. transformed or transfected with an expression vector as described above) under conditions to provide for expression (by the vector) of a coding sequence encoding the polypeptide, and optionally recovering the expressed polypeptide. Polynucleotides of the invention can be incorporated into a recombinant replicable vector, e.g. an expression vector. The vector may be used to replicate the nucleic acid in a compatible host cell. Thus in a further embodiment, the invention provides a method of making a polynucleotide of the invention by introducing a polynucleotide of the invention into a replicable vector, introducing the vector into a compatible host cell, and growing the host cell under conditions which bring about the replication of the vector. The vector may be recovered from the host cell.

The vectors may be transformed or transfected into a suitable host cell as described above to provide for expression of a polypeptide of the invention. This process may comprise culturing a host cell transformed with an expression vector as described above under conditions to provide for expression by the vector of a coding sequence encoding the polypeptide.

Herein standard isolation, hybridization, transformation and cloning techniques are used (e.g., as described in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989).

Homology & Identity

Amino acid or nucleotide sequences are said to be homologous when exhibiting a certain level of similarity. Two sequences being homologous indicate a common evolutionary origin. Whether two homologous sequences are closely related or more distantly related is indicated by "percent identity" or "percent similarity", which is high or low respectively. Although disputed, to indicate "percent identity" or "percent similarity", "level of homology" or "percent homology" is frequently used interchangeably.

A comparison of sequences and determination of percent identity between two sequences can be accomplished using a mathematical algorithm. The skilled person will be aware of the fact that several different computer programs are available to align two sequences and determine the homology between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent identity between two amino acid sequences can be determined using the Needleman and Wunsch algorithm for the alignment of two sequences. (Needleman, S. B. and Wunsch, C. D. (1970) J. Mol. Biol. 48, 443-453). The algorithm aligns amino acid sequences as well as nucleotide sequences. The Needleman-Wunsch algorithm has been implemented in the computer program NEEDLE. For the purpose of this invention the NEEDLE program from the EMBOSS package was used (version 2.8.0 or higher, *EMBOSS: The European Molecular Biology Open Software Suite* (2000) Rice, P. Longden, I. and Bleasby, A. Trends in Genetics 16, (6) pp 276-277, http://emboss.bioinformatics.nl/). For protein sequences, EBLO-SUM62 is used for the substitution matrix. For nucleotide sequences, EDNAFULL is used. Other matrices can be specified. The optional parameters used for alignment of amino acid sequences are a gap-open penalty of 10 and a gap extension penalty of 0.5. The skilled person will appreciate that all these different parameters will yield slightly different results but that the overall percentage identity of two sequences is not significantly altered when using different algorithms.

Global Homology Definition

The homology or identity is the percentage of identical matches between the two full sequences over the total aligned region including any gaps or extensions. The homology or identity between the two aligned sequences is calculated as follows: Number of corresponding positions in the alignment showing an identical amino acid in both sequences divided by the total length of the alignment including the gaps. The identity defined as herein can be obtained from NEEDLE and is labelled in the output of the program as "IDENTITY".

Longest Identity Definition

The homology or identity between the two aligned sequences is calculated as follows: Number of corresponding positions in the alignment showing an identical amino acid in both sequences divided by the total length of the alignment after subtraction of the total number of gaps in the alignment. The identity defined as herein can be obtained from NEEDLE by using the NOBRIEF option and is labelled in the output of the program as "longest-identity".

With the identity to SEQ ID NO: 20 as defined herein above an overview of GLO1 aminoacids that are active in cells according to the invention is given in table 1.

TABLE 1

Overview of GLO1 aminoacids active in cell according to invention (see examples) and identity to GLO1 of *Saccharomyces cerevisiae* (SEQ ID NO: 20).

| Source of GLO1 | % identity to SEQ ID NO: 20 | SEQ ID NO |
|---|---|---|
| *Saccharomyces cerevisiae* | 100 | 20 |
| *Candida glabrata* | 69 | 21 |
| *Kluyveromyces lactis* | 61 | 23 |
| *Zygosaccharomyces rouxii* | 61 | 22 |
| *Candida magnoliae* | 45 | 24 |

Therefore, in an embodiment the GLO1 nucleotide or amino acid is derived from a microorganism chosen from the group consisting of *Saccharomyces cerevisiae, Candida glabrata, Kluyveromyces lactis, Zygosaccharomyces rouxii* and *Candida magnolia*.

In an embodiment the GLO1 nucleotide or amino acid is derived from a microorganism chosen from the group consisting of *Saccharomyces cerevisiae, Candida glabrata, Kluyveromyces lactis* and *Candida magnolia*.

In an embodiment, the GLO nucleotide is a codon pair optimized nucleotide sequence, wherein the sequence is SED ID NO: 34, SED ID NO: 35, SED ID NO: 36, SED ID NO: 37, SED ID NO: 38.

In an embodiment, the GLO nucleotide is a codon pair optimized nucleotide sequence, wherein the sequence is SED ID NO: 34, SED ID NO: 35, SED ID NO: 36, or SED ID NO: 37.

The various embodiments of the invention described herein may be cross-combined. The invention relates to a cell according to claim 1. Such cell is herein also designated as transformed host cell. Embodiments thereof are now described.

The cell is capable of using L-arabinose and xylose. In an embodiment, the cell is capable of converting L-arabinose into L-ribulose and/or xylulose 5-phosphate and/or into a desired fermentation product, for example one of those mentioned herein.

Organisms, for example *S. cerevisiae* strains, able to produce ethanol from L-arabinose may be produced by modifying a host cell introducing the araA (L-arabinose isomerase), araB (L-ribulokinase) and araD (L-ribulose-5-P4-epimerase) genes from a suitable source. Such genes may be introduced into a host cell in order that it is capable of using arabinose. Such an approach is given is described in WO2003/095627. araA, araB and araD genes from *Lactobacillus plantarum* may be used and are disclosed in WO2008/041840. The araA gene from *Bacillus subtilis* and the araB and araD genes from *Escherichia coli* may be used and are disclosed in EP1499708. In another embodiment, araA, araB and araD genes may derived from of at least one of the genus *Clavibacter, Arthrobacter* and/or *Gramella*, in particular one of *Clavibacter michiganensis, Arthrobacter aurescens*, and/or *Gramella forsetii*, as disclosed in WO 2009011591.

In an embodiment, the transformed host cell may also comprise one or more copies of xylose isomerase gene and/or one or more copies of xylose reductase and/or xylitol dehydrogenase.

The number of copies may be determined by the skilled person by any known method. In an embodiment, the transformed host cell is able to ferment glucose, arabinose, xylose and galactose.

In an embodiment, the cell is capable of converting 90% or more glucose, xylose arabinose, galactose and mannose available, into a fermentation product. In an embodiment, cell is capable of converting 91% or more, 92% or more, 94% or more, 95% or more, 96% or more, 97% or more, 98% or more or 100% of all glucose, xylose arabinose, galactose and mannose available, into a fermentation product.

In one embodiment of the invention the transformed host cell is able to ferment one or more additional sugar, preferably C5 and/or C6 sugar e.g. mannose. In an embodiment of the invention the transformed host cell comprises one or more of: a xylA-gene, XYL1 gene and XYL2 gene and/or XKS1-gene, to allow the transformed host cell to ferment xylose; deletion of the aldose reductase (GRE3) gene; overexpression of PPP-genes TAD, TKL1, RPE1 and RKI1 to allow the increase of the flux through the pentose phosphate pathway in the cell.

In an embodiment, the transformed host cell is an industrial cell, more preferably an industrial yeast (as defined herein above in the section host).

In an embodiment the transformed host cell is inhibitor tolerant. Inhibitor tolerance is resistance to inhibiting compounds. The presence and level of inhibitory compounds in lignocellulose may vary widely with variation of feedstock, pretreatment method hydrolysis process. Examples of categories of inhibitors are carboxylic acids, furans and/or phenolic compounds. Examples of carboxylic acids are lactic acid, acetic acid or formic acid. Examples of furans are furfural and hydroxy-methylfurfural. Examples or phenolic compounds are vanillin, syringic acid, ferulic acid and coumaric acid. The typical amounts of inhibitors are for carboxylic acids: several grams per liter, up to 20 grams per liter or more, depending on the feedstock, the pretreatment and the hydrolysis conditions. For furans: several hundreds of milligrams per liter up to several grams per liter, depending on the feedstock, the pretreatment and the hydrolysis conditions.

For phenolics: several tens of milligrams per liter, up to a gram per liter, depending on the feedstock, the pretreatment and the hydrolysis conditions.

The transformed host cells according to the invention may be inhibitor tolerant, i.e. they can withstand common inhibitors at the level that they typically have with common pretreatment and hydrolysis conditions, so that the transformed host cells can find broad application, i.e. it has high applicability for different feedstock, different pretreatment methods and different hydrolysis conditions.

In one embodiment, the industrial transformed host cell is constructed on the basis of an inhibitor tolerant host cell, wherein the construction is conducted as described hereinafter. Inhibitor tolerant host cells may be selected by screening strains for growth on inhibitors containing materials, such as illustrated in Kadar et al, Appl. Biochem. Biotechnol. (2007), Vol. 136-140, 847-858, wherein an inhibitor tolerant S. cerevisiae strain ATCC 26602 was selected.

In an embodiment, the transformed host cell is marker-free. As used herein, the term "marker" refers to a gene encoding a trait or a phenotype which permits the selection of, or the screening for, a host cell containing the marker. Marker-free means that markers are essentially absent in the transformed host cell. Being marker-free is particularly advantageous when antibiotic markers have been used in construction of the transformed host cell and are removed thereafter. Removal of markers may be done using any suitable prior art technique, e.g intramolecular recombination. A suitable method of marker removal is illustrated in the examples.

A transformed host cell may be able to convert plant biomass, celluloses, hemicelluloses, pectins, starch, starch derivatives, for example into fermentable sugars. Accordingly, a transformed host cell may express one or more enzymes such as a cellulase (an endocellulase or an exocellulase), a hemicellulase (an endo- or exo-xylanase or arabinase) necessary for the conversion of cellulose into glucose monomers and hemicellulose into xylose and arabinose monomers, a pectinase able to convert pectins into glucuronic acid and galacturonic acid or an amylase to convert starch into glucose monomers.

The transformed host cell further may comprise those enzymatic activities required for conversion of sugar to a desired fermentation product, such as ethanol, butanol, lactic acid, 3-hydroxy-propionic acid, acrylic acid, acetic acid, succinic acid, citric acid, fumaric acid, malic acid, itaconic acid, an amino acid, 1,3-propane-diol, ethylene, glycerol, a β-lactam antibiotic or a cephalosporin.

In an embodiment, the transformed host cell is a cell that is naturally capable of alcoholic fermentation, preferably, anaerobic alcoholic fermentation. A transformed host cell preferably has a high tolerance to ethanol, a high tolerance to low pH (i.e. capable of growth at a pH lower than about 5, about 4, about 3, or about 2.5) and towards organic and/or a high tolerance to elevated temperatures.

Any of the above characteristics or activities of a transformed host cell may be naturally present in the cell or may be introduced or modified by genetic modification.

Construction of the Transformed Host Cell

According to an embodiment, the genes may be introduced in the host cell by introduction into a host cell one or more of:

a) the genes araA, araB and araD under control of strong constitutive promoter(s);
b) PPP-genes TAD, TKL1, RPE1 and RKI1, optionally under control of one or more strong constitutive promoter;
c) deletion of an aldose reductase gene;
d) a xylA-gene and a XKS1-gene under control of strong constitutive promoter(s);
e) a xylA gene under control of a strong constitutive promoter, which has the ability to integrate into the genome on multiple loci;

and adaptive evolution to produce the transformed host cell. The above cell may be constructed using recombinant expression techniques.

Recombinant Expression

The transformed host cell is a recombinant cell. That is to say, a transformed host cell comprises, or is transformed with or is genetically modified with a nucleotide sequence that does not naturally occur in the cell in question.

Techniques for the recombinant expression of enzymes in a cell, as well as for the additional genetic modifications of a transformed host cell are well known to those skilled in the art. Typically such techniques involve transformation of a cell with nucleic acid construct comprising the relevant sequence. Such methods are, for example, known from standard handbooks, such as Sambrook and Russel (2001) "Molecular Cloning: A Laboratory Manual (3rd edition), Cold Spring Harbor Laboratory, Cold Spring Harbor Laboratory Press, or F. Ausubel et al., eds., "Current protocols in molecular biology", Green Publishing and Wiley Interscience, New York (1987). Methods for transformation and genetic modification of host cells are known from e.g. EP-A-0635 574, WO 98/46772, WO 99/60102, WO 00/37671, WO90/14423, EP-A-0481008, EP-A-0635574 and U.S. Pat. No. 6,265,186.

Typically, the nucleic acid construct may be a plasmid, for instance a low copy plasmid or a high copy plasmid. The cell according to the present invention may comprise a single or multiple copies of the nucleotide sequence encoding a enzyme, for instance by multiple copies of a nucleotide construct or by use of construct which has multiple copies of the enzyme sequence.

The nucleic acid construct may be maintained episomally and thus comprise a sequence for autonomous replication, such as an autosomal replication sequence. A suitable episomal nucleic acid construct may e.g. be based on the yeast 2μ or pKD1 plasmids (Gleer et al., 1991, Biotechnology 9: 968-975), or the AMA plasmids (Fierro et al., 1995, Curr Genet. 29:482-489). Alternatively, each nucleic acid construct may be integrated in one or more copies into the genome of the cell. Integration into the cell's genome may occur at random by non-homologous recombination but preferably, the nucleic acid construct may be integrated into the cell's genome by homologous recombination as is well known in the art (see e.g. WO90/14423, EP-A-0481008, EP-A-0635 574 and U.S. Pat. No. 6,265,186).

Most episomal or 2μ plasmids are relatively unstable in yeast, being lost in approximately $10^{-2}$ or more cells after each generation. Even under conditions of selective growth, only 60% to 95% of the cells retain the episomal plasmid. The copy number of most episomal plasmids ranges from 20-100 per cell of cir$^+$ hosts. However, the plasmids are not equally distributed among the cells, and there is a high variance in the copy number per cell in populations. Strains transformed with integrative plasmids are extremely stable, even in the absence of selective pressure. However, plasmid loss can occur at approximately $10^{-3}$ to $10^{-4}$ frequencies by homologous recombination between tandemly repeated DNA, leading to looping out of the vector sequence. Preferably, the vector design in the case of stable integration is thus, that upon loss of the selection marker genes (which also occurs by intramolecular, homologous recombination) that looping out of the integrated construct is no longer possible. Preferably the genes are thus stably integrated. Stable integration is herein defined as integration into the genome, wherein looping out of the integrated construct is no longer possible. Preferably selection markers are absent. Typically, the enzyme encoding sequence will be operably linked to one or more nucleic acid sequences, capable of providing for or aiding the transcription and/or translation of the enzyme sequence.

The term "operably linked" refers to a juxtaposition wherein the components described are in a relationship permitting them to function in their intended manner. For instance, a promoter or enhancer is operably linked to a coding sequence the said promoter or enhancer affects the transcription of the coding sequence.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences known to one of skilled in the art. A "constitutive" promoter is a promoter that is active under most environmental and developmental conditions. An "inducible" promoter is a promoter that is active under environmental or developmental regulation.

The promoter that could be used to achieve the expression of a nucleotide sequence coding for an enzyme according to the present invention, may be not native to the nucleotide sequence coding for the enzyme to be expressed, i.e. a promoter that is heterologous to the nucleotide sequence (coding sequence) to which it is operably linked. The promoter may, however, be homologous, i.e. endogenous, to the host cell.

Promotors are widely available and known to the skilled person. Suitable examples of such promoters include e.g. promoters from glycolytic genes, such as the phosphofructokinase (PFK), triose phosphate isomerase (TPI), glyceraldehyde-3-phosphate dehydrogenase (GPD, TDH3 or GAPDH), pyruvate kinase (PYK), phosphoglycerate kinase (PGK) promoters from yeasts or filamentous fungi; more details about such promoters from yeast may be found in (WO 93/03159). Other useful promoters are ribosomal protein encoding gene promoters, the lactase gene promoter (LAC4), alcohol dehydrogenase promoters (ADH1, ADH4, and the like), and the enolase promoter (ENO). Other promoters, both constitutive and inducible, and enhancers or upstream activating sequences will be known to those of skill in the art. The promoters used in the host cells of the invention may be modified, if desired, to affect their control characteristics. Suitable promoters in this context include both constitutive and inducible natural promoters as well as engineered promoters, which are well known to the person skilled in the art. Suitable promoters in eukaryotic host cells may be GAL7, GAL10, or GAL1, CYC1, HIS3, ADH1, PGL, PHO5, GAPDH, ADC1, TRP1, URA3, LEU2, ENO1, TPI1, and AOX1. Other suitable promoters include PDC1, GPD1, PGK1, TEF1, and TDH3.

In a transformed host cell, the 3'-end of the nucleotide acid sequence encoding enzyme preferably is operably linked to a transcription terminator sequence. Preferably the terminator sequence is operable in a host cell of choice, such as e.g. the yeast species of choice. In any case the choice of the terminator is not critical; it may e.g. be from any yeast gene, although terminators may sometimes work if from a non-yeast, eukaryotic, gene. Usually a nucleotide sequence encoding the enzyme comprises a terminator. Preferably, such terminators are combined with mutations that prevent nonsense mediated mRNA decay in the host transformed host cell (see for example: Shirley et al., 2002, Genetics 161:1465-1482).

The transcription termination sequence further preferably comprises a polyadenylation signal.

Optionally, a selectable marker may be present in a nucleic acid construct suitable for use in the invention. As used herein, the term "marker" refers to a gene encoding a trait or a phenotype which permits the selection of, or the screening for, a host cell containing the marker. The marker gene may be an antibiotic resistance gene whereby the appropriate antibiotic can be used to select for transformed cells from among cells that are not transformed. Examples of suitable antibiotic resistance markers include e.g. dihydrofolate reductase, hygromycin-B-phosphotransferase, 3'-O-phosphotransferase II (kanamycin, neomycin and G418 resistance). Antibiotic resistance markers may be most convenient for the transformation of polyploid host cells, Also non-antibiotic resistance markers may be used, such as auxotrophic markers (URA3, TRP1, LEU2) or the *S. pombe* TPI gene (described by Russell P R, 1985, Gene 40: 125-130). In a preferred embodiment the host cells transformed with the nucleic acid constructs are marker gene free. Methods for constructing recombinant marker gene free microbial host cells are disclosed in EP-A-0635 574 and are based on the use of bidirectional markers such as the *A. nidulans* amdS (acetamidase) gene or the yeast URA3 and LYS2 genes. Alternatively, a screenable marker such as Green Fluorescent Protein, lacL, luciferase, chloramphenicol acetyltransferase, beta-glucuronidase may be incorporated into the nucleic acid constructs of the invention allowing to screen for transformed cells.

Optional further elements that may be present in the nucleic acid constructs suitable for use in the invention include, but are not limited to, one or more leader sequences, enhancers, integration factors, and/or reporter genes, intron sequences, centromers, telomers and/or matrix attachment (MAR) sequences. The nucleic acid constructs of the invention may further comprise a sequence for autonomous replication, such as an ARS sequence.

The recombination process may thus be executed with known recombination techniques. Various means are known to those skilled in the art for expression and overexpression of enzymes in a transformed host cell. In particular, an enzyme may be overexpressed by increasing the copy number of the gene coding for the enzyme in the host cell, e.g. by integrating additional copies of the gene in the host cell's genome, by expressing the gene from an episomal multicopy expression vector or by introducing a episomal expression vector that comprises multiple copies of the gene.

Alternatively, overexpression of enzymes in the host cells of the invention may be achieved by using a promoter that is not native to the sequence coding for the enzyme to be overexpressed, i.e. a promoter that is heterologous to the coding sequence to which it is operably linked. Although the promoter preferably is heterologous to the coding sequence to which it is operably linked, it is also preferred that the promoter is homologous, i.e. endogenous to the host cell. Preferably the heterologous promoter is capable of producing a higher steady state level of the transcript comprising the coding sequence (or is capable of producing more transcript molecules, i.e. mRNA molecules, per unit of time) than is the promoter that is native to the coding sequence. Suitable promoters in this context include both constitutive and inducible natural promoters as well as engineered promoters.

In an embodiment, the transformed host cell is marker-free, which means that no auxotrophic or dominant markers, in particular antibiotic resistance markers, are present in the genome or extra-chromosomally.

The coding sequence used for overexpression of the enzymes mentioned above may preferably be homologous to the host cell. However, coding sequences that are heterologous to the host may be used.

Overexpression of an enzyme, when referring to the production of the enzyme in a genetically modified cell, means that the enzyme is produced at a higher level of specific enzymatic activity as compared to the unmodified host cell under identical conditions. Usually this means that the enzymatically active protein (or proteins in case of multi-subunit enzymes) is produced in greater amounts, or rather at a higher steady state level as compared to the unmodified host cell under identical conditions. Similarly this usually means that the mRNA coding for the enzymatically active protein is produced in greater amounts, or again rather at a higher steady state level as compared to the unmodified host cell under identical conditions. Preferably in a host, an enzyme to be overexpressed is overexpressed by at least a factor of about 1.1, about 1.2, about 1.5, about 2, about 5, about 10 or about 20 as compared to a strain which is genetically identical except for the genetic modification causing the overexpression. It is to be understood that these levels of overexpression may apply to the steady state level of the enzyme's activity, the steady state level of the enzyme's protein as well as to the steady state level of the transcript coding for the enzyme.

Preferably, the glyoxalase is expressed in the cytosol.

Adaptation

Adaptation is the evolutionary process whereby a population becomes better suited (adapted) to its habitat or habitats. This process takes place over several to many generations, and is one of the basic phenomena of biology.

The term adaptation may also refer to a feature which is especially important for an organism's survival. Such adaptations are produced in a variable population by the better suited forms reproducing more successfully, by natural selection.

Changes in environmental conditions alter the outcome of natural selection, affecting the selective benefits of subsequent adaptations that improve an organism's fitness under the new conditions. In the case of an extreme environmental change, the appearance and fixation of beneficial adaptations can be essential for survival. A large number of different factors, such as e.g. nutrient availability, temperature, the availability of oxygen, etcetera, can drive adaptive evolution.

Fitness

There is a clear relationship between adaptedness (the degree to which an organism is able to live and reproduce in a given set of habitats) and fitness. Fitness is an estimate and a predictor of the rate of natural selection. By the application of natural selection, the relative frequencies of alternative phenotypes will vary in time, if they are heritable.

Genetic Changes

When natural selection acts on the genetic variability of the population, genetic changes are the underlying mechanism. By this means, the population adapts genetically to its circumstances. Genetic changes may result in visible structures, or may adjust the physiological activity of the organism in a way that suits the changed habitat.

It may occur that habitats frequently change. Therefore, it follows that the process of adaptation is never finally complete. In time, it may happen that the environment changes gradually, and the species comes to fit its surroundings better and better. On the other hand, it may happen that changes in the environment occur relatively rapidly, and then the species becomes less and less well adapted. Adaptation is a genetic process, which goes on all the time to some extent, also when the population does not change the habitat or environment.

The Adaptive Evolution

The transformed host cells may in their preparation be subjected to adaptive evolution. A transformed host cell may be adapted to sugar utilisation by selection of mutants, either spontaneous or induced (e.g. by radiation or chemicals), for growth on the desired sugar, preferably as sole carbon source, and more preferably under anaerobic conditions. Selection of mutants may be performed by techniques including serial transfer of cultures as e.g. described by Kuyper et al. (2004, FEMS Yeast Res. 4: 655-664) or by cultivation under selective pressure in a chemostat culture. E.g. in a preferred host cell at least one of the genetic modifications described above, including modifications obtained by selection of mutants, confer to the host cell the ability to grow on the xylose as carbon source, preferably as sole carbon source, and preferably under anaerobic conditions. When XI is used as gene to convert xylose, preferably the cell produce essentially no xylitol, e.g. the xylitol produced is below the detection limit or e.g. less than about 5, about 2, about 1, about 0.5, or about 0.3% of the carbon consumed on a molar basis.

Adaptive evolution is also described e.g. in Wisselink H. W. et al, Applied and Environmental Microbiology August 2007, p. 4881-4891

In one embodiment of adaptive evolution a regimen consisting of repeated batch cultivation with repeated cycles of consecutive growth in different media is applied, e.g. three media with different compositions (glucose, xylose, and arabinose; xylose and arabinose. See Wisselink et al. (2009) Applied and Environmental Microbiology, February 2009, p. 907-914.

Yeast Transformation and Genetic Stability

Genetic engineering, i.e. transformation of yeast cells with recombinant DNA, became feasible for the first time in 1978 [Beggs, 1978; Hinnen et al., 1978]. Recombinant DNA technology in yeast has established itself since then. A multitude of different vector constructs are available. Generally, these plasmid vectors, called shuttle vectors, contain genetic material derived from *E. coli* vectors consisting of an origin of replication and a selectable marker (often the β-lactamase gene, ampR), which enable them to be propagated in *E. coli* prior to transformation into yeast cells. Additionally, the shuttle vectors contain a selectable marker for selection in yeast. Markers can be genes encoding enzymes for the synthesis of a particular amino acid or nucleotide, so that cells carrying the corresponding genomic deletion (or mutation) are complemented for auxotrophy or autotrophy. Alternatively, these vectors contain heterologous dominant resistance markers, which provides recombinant yeast cells (i.e. the cells that have taken up the DNA and express the marker gene) resistance towards certain antibiotics, like G418 (geneticin), hygromycin B or phleomycin. In addition, these vectors may contain a sequence of (combined) restriction sites (multiple cloning site or MCS) which will allow cloning foreign DNA into these sites, although alternative methods exist as well.

Traditionally, four types of shuttle vectors can be distinguished by the absence or presence of additional genetic elements:

- Integrative plasmids (YIp) which by homologous recombination are integrated into the host genome at the locus of the marker or another gene, when this is opened by restriction and the linearized DNA is used for transformation of the yeast cells. This generally results in the presence of one copy of the foreign DNA inserted at this particular site in the genome.
- Episomal plasmids (YEp) which carry part of the 2p plasmid DNA sequence necessary for autonomous replication in yeast cells. Multiple copies of the transformed plasmid are propagated in the yeast cell and maintained as episomes.
- Autonomously replicating plasmids (YRp) which carry a yeast origin of replication (ARS, autonomously replicated sequence) that allows the transformed plasmids to be propagated several hundred-fold.
- CEN plasmids (YCp) which carry in addition to an ARS sequence a centromeric sequence (derived from one of the nuclear chromosomes) which normally guarantees stable mitotic segregation and usually reduces the copy number of self-replicated plasmid to just one.

These plasmids are being introduced into the yeast cells by transformation. Transformation of yeast cells may be achieved by several different techniques, such as permeabilization of cells with lithium acetate (Ito et al, 1983) and electroporation methods.

In commercial application of recombinant microorganisms, plasmid instability is the most important problem. Instability is the tendency of the transformed cells to lose their engineered properties because of changes to, or loss of, plasmids. This issue is discussed in detail by Zhang et al (Plasmid stability in recombinant *Saccharomyces cerevisiae*. Biotechnology Advances, Vol. 14, No. 4, pp. 401-435, 1996). Strains transformed with integrative plasmids are extremely stable, even in the absence of selective pressure (Sherman, F. http://dbb.urmc.rochester.edu/labs/sherman_f/yeast/9.html and references therein).

The heterologous DNA is usually introduced into the organism in the form of extra-chromosomal plasmids (YEp, YCp and YRp). Unfortunately, it has been found with both bacteria and yeasts that the new characteristics may not be retained, especially if the selection pressure is not applied continuously. This is due to the segregational instability of the hybrid plasmid when recombinant cells grow for a long period of time. This leads to population heterogeneity and clonal variability, and eventually to a cell population in which the majority of the cells has lost the properties that were introduced by transformation. If vectors with auxotrophic markers are being used, cultivation in rich media often leads to rapid loss of the vector, since the vector is only retained in minimal media. The alternative, the use of dominant antibiotic resistance markers, is often not compatible with production processes. The use of antibiotics may not be desired from a registration point of view (the possibility that trace amounts of the antibiotic end up in the end product) or for economic reasons (costs of the use of antibiotics at industrial scale).

Loss of vectors leads to problems in large scale production situations. Alternative methods for introduction of DNA do exist for yeasts, such as the use of integrating plasmids (YIp). The DNA is integrated into the host genome by recombination, resulting in high stability. (Gaunt, P. Stability of recombinant plasmids in yeast. Journal of Biotechnology 9(1988) 173-192). We have found that an integration method using the host transposons are a good alternative. In an embodiment genes may be integrated into the transformed host cell. Initial introduction (i.e. before adaptive evolution) of multiple copies be executed in any way known in the art that leads to introduction of the genes. In an embodiment, this may be accomplished using a vector with parts homologous to repeated sequences (transposons), of the host cell. When the host cell is a yeast cell, suitable repeated sequences are the long terminal repeats (LTR) of the Ty element, known as delta sequence. Ty elements fall into two rather similar subfamilies called Ty1 and Ty2. These elements are about 6 kilobases (kb) in length and are bounded by long terminal repeats (LTR), sequences of about 335 base pairs (Boeke J D et al, The *Saccharomyces cerevisiae* Genome Contains Functional and Nonfunctional Copies of Transposon Ty1. Molecular and Cellular Biology, April 1988, p. 1432-1442 Vol. 8, No. 4). In the fully sequenced *S. cerevisiae* strain, S288c, the most abundant transposons are Ty1 (31 copies) and Ty2 (13 copies) (Gabriel A, Dapprich J, Kunkel M, Gresham D, Pratt S C, et al. (2006) Global mapping of transposon location. PLoS Genet 2(12): e212.doi:10.1371/journal.pgen.0020212). These transposons consist of two overlapping open reading frames (ORFS), each of which encode several proteins. The coding regions are flanked by the aforementioned, nearly identical LTRs. Other, but less abundant and more distinct Ty elements in *S. cerevisiae* comprise Ty3, Ty4 and Ty5. For each family of full-length Ty elements there are an order of magnitude more solo LTR elements dispersed through the genome. These are thought to arise by LTR-LTR recombination of full-length elements, with looping out of the internal protein encoding regions.

The retrotransposition mechanism of the Ty retrotransposon has been exploited to integrate multiple copies throughout the genome (Boeke et al., 1988; Jacobs et al., 1988). The long terminal repeats (LTR) of the Ty element, known as delta sequences, are also good targets for integration by homologous recombination as they exist in about 150-200 copies that are either Ty associated or solo sites (Boeke, 1989; Kingsman and Kingsman, 1988). (Parekh R. N. (1996). An Integrating Vector for Tunable, High Copy, Stable Integration into the Dispersed Ty DELTA Sites of *Saccharomyces cerevisiae*. Biotechnol. Prog. 1996, 12, 16-21). By adaptive evolution, the number of copies may change.

araA, araB and araD Genes

A transformed host cell is capable of using arabinose. A transformed host cell is therefore, be capable of converting L-arabinose into L-ribulose and/or xylulose 5-phosphate and/or into a desired fermentation product, for example one of those mentioned herein.

Organisms, for example *S. cerevisiae* strains, able to produce ethanol from L-arabinose may be produced by modifying a cell introducing the araA (L-arabinose isomerase), araB (L-ribulokinase) and araD (L-ribulose-5-P4-epimerase) genes from a suitable source. Such genes may be introduced into a transformed host cell is order that it is capable of using arabinose. Such an approach is given is described in WO2003/095627. araA, araB and araD genes from *Lactobacillus plantarum* may be used and are disclosed in WO2008/041840. The araA gene from *Bacillus subtilis* and the araB and araD genes from *Escherichia coli* may be used and are disclosed in EP1499708. In another embodiment, araA, araB and araD genes may derived from of at least one of the genus *Clavibacter, Arthrobacter* and/or

*Gramella*, in particular one of *Clavibacter Michiganensis, Arthrobacter Aurescens*, and/or *Gramella Forsetii*, as disclosed in WO 2009011591.

PPP-Genes

A transformed host cell may comprise one or more genetic modifications that increases the flux of the pentose phosphate pathway (PPP). In particular, the genetic modification(s) may lead to an increased flux through the non-oxidative part of the pentose phosphate pathway. A genetic modification that causes an increased flux of the non-oxidative part of the pentose phosphate pathway is herein understood to mean a modification that increases the flux by at least a factor of about 1.1, about 1.2, about 1.5, about 2, about 5, about 10 or about 20 as compared to the flux in a strain which is genetically identical except for the genetic modification causing the increased flux. The flux of the non-oxidative part of the pentose phosphate pathway may be measured by growing the modified host on xylose as sole carbon source, determining the specific xylose consumption rate and subtracting the specific xylitol production rate from the specific xylose consumption rate, if any xylitol is produced. However, the flux of the non-oxidative part of the pentose phosphate pathway is proportional with the growth rate on xylose as sole carbon source, preferably with the anaerobic growth rate on xylose as sole carbon source. There is a linear relation between the growth rate on xylose as sole carbon source ($\mu_{max}$) and the flux of the non-oxidative part of the pentose phosphate pathway. The specific xylose consumption rate ($Q_s$) is related to the specific growth rate ($\mu$) and to the yield of biomass on sugar ($Y_{xs}$) according to:

$$Q_s = m_s + \mu/y_{sx}^{max}$$

or $$1/y_{sx} = m_s/\mu + 1/y_{sx}^{max}$$

Therefore if $\mu$ is constant, the increased flux of the non-oxidative part of the pentose phosphate pathway may be deduced from the increase in maximum growth rate under these conditions unless transport (uptake is limiting).

One or more genetic modifications that increase the flux of the pentose phosphate pathway may be introduced in the host cell in various ways. These including e.g. achieving higher steady state activity levels of xylulose kinase and/or one or more of the enzymes of the non-oxidative part pentose phosphate pathway and/or a reduced steady state level of unspecific aldose reductase activity. These changes in steady state activity levels may be effected by selection of mutants (spontaneous or induced by chemicals or radiation) and/or by recombinant DNA technology e.g. by overexpression or inactivation, respectively, of genes encoding the enzymes or factors regulating these genes.

In a preferred host cell, the genetic modification comprises overexpression of at least one enzyme of the (non-oxidative part) pentose phosphate pathway. Preferably the enzyme is selected from the group consisting of the enzymes encoding for ribulose-5-phosphate isomerase, ribulose-5-phosphate epimerase, transketolase and transaldolase. Various combinations of enzymes of the (non-oxidative part) pentose phosphate pathway may be overexpressed. E.g. the enzymes that are overexpressed may be at least the enzymes ribulose-5-phosphate isomerase and ribulose-5-phosphate epimerase; or at least the enzymes ribulose-5-phosphate isomerase and transketolase; or at least the enzymes ribulose-5-phosphate isomerase and transaldolase; or at least the enzymes ribulose-5-phosphate epimerase and transketolase; or at least the enzymes ribulose-5-phosphate epimerase and transaldolase; or at least the enzymes transketolase and transaldolase; or at least the enzymes ribulose-5-phosphate epimerase, transketolase and transaldolase; or at least the enzymes ribulose-5-phosphate isomerase, transketolase and transaldolase; or at least the enzymes ribulose-5-phosphate isomerase, ribulose-5-phosphate epimerase, and transaldolase; or at least the enzymes ribulose-5-phosphate isomerase, ribulose-5-phosphate epimerase, and transketolase. In one embodiment of the invention each of the enzymes ribulose-5-phosphate isomerase, ribulose-5-phosphate epimerase, transketolase and transaldolase are overexpressed in the host cell. More preferred is a host cell in which the genetic modification comprises at least overexpression of both the enzymes transketolase and transaldolase as such a host cell is already capable of anaerobic growth on xylose. In fact, under some conditions xylose converting host cells overexpressing only the transketolase and the transaldolase already have the same anaerobic growth rate on xylose as do host cells that overexpress all four of the enzymes, i.e. the ribulose-5-phosphate isomerase, ribulose-5-phosphate epimerase, transketolase and transaldolase. Moreover, host cells overexpressing both of the enzymes ribulose-5-phosphate isomerase and ribulose-5-phosphate epimerase are preferred over host cells overexpressing only the isomerase or only the epimerase as overexpression of only one of these enzymes may produce metabolic imbalances.

The enzyme "ribulose 5-phosphate epimerase" (EC 5.1.3.1) is herein defined as an enzyme that catalyses the epimerisation of D-xylulose 5-phosphate into D-ribulose 5-phosphate and vice versa. The enzyme is also known as phosphoribulose epimerase; erythrose-4-phosphate isomerase; phosphoketopentose 3-epimerase; xylulose phosphate 3-epimerase; phosphoketopentose epimerase; ribulose 5-phosphate 3-epimerase; D-ribulose phosphate-3-epimerase; D-ribulose 5-phosphate epimerase; D-ribulose-5-P 3-epimerase; D-xylulose-5-phosphate 3-epimerase; pentose-5-phosphate 3-epimerase; or D-ribulose-5-phosphate 3-epimerase. A ribulose 5-phosphate epimerase may be further defined by its amino acid sequence. Likewise a ribulose 5-phosphate epimerase may be defined by a nucleotide sequence encoding the enzyme as well as by a nucleotide sequence hybridising to a reference nucleotide sequence encoding a ribulose 5-phosphate epimerase. The nucleotide sequence encoding for ribulose 5-phosphate epimerase is herein designated RPE1.

The enzyme "ribulose 5-phosphate isomerase" (EC 5.3.1.6) is herein defined as an enzyme that catalyses direct isomerisation of D-ribose 5-phosphate into D-ribulose 5-phosphate and vice versa. The enzyme is also known as phosphopentosisomerase; phosphoriboisomerase; ribose phosphate isomerase; 5-phosphoribose isomerase; D-ribose 5-phosphate isomerase; D-ribose-5-phosphate ketol-isomerase; or D-ribose-5-phosphate aldose-ketose-isomerase. A ribulose 5-phosphate isomerase may be further defined by its amino acid sequence. Likewise a ribulose 5-phosphate isomerase may be defined by a nucleotide sequence encoding the enzyme as well as by a nucleotide sequence hybridising to a reference nucleotide sequence encoding a ribulose 5-phosphate isomerase. The nucleotide sequence encoding for ribulose 5-phosphate isomerase is herein designated RKI1.

The enzyme "transketolase" (EC 2.2.1.1) is herein defined as an enzyme that catalyses the reaction: D-ribose 5-phosphate+D-xylulose 5-phosphate<->sedoheptulose 7-phosphate+D-glyceraldehyde 3-phosphate and vice versa. The enzyme is also known as glycolaldehydetransferase or sedoheptulose-7-phosphate; D-glyceraldehyde-3-phosphate glycolaldehydetransferase. A transketolase may be further defined by its amino acid. Likewise a transketolase may be defined by a nucleotide sequence encoding the enzyme as well as by a nucleotide sequence hybridising to a reference nucleotide sequence encoding a transketolase. The nucleotide sequence encoding for transketolase is herein designated TKL1.

The enzyme "transaldolase" (EC 2.2.1.2) is herein defined as an enzyme that catalyses the reaction: sedoheptulose 7-phosphate+D-glyceraldehyde 3-phosphate<->D-erythrose 4-phosphate+D-fructose 6-phosphate and vice versa. The enzyme is also known as dihydroxyacetonetransferase; dihydroxyacetone synthase; formaldehyde transketolase; or sedoheptulose-7-phosphate:D-glyceraldehyde-3-phosphate glyceronetransferase. A transaldolase may be further defined by its amino acid sequence. Likewise a transaldolase may be defined by a nucleotide sequence encoding the enzyme as well as by a nucleotide sequence hybridising to a reference nucleotide sequence encoding a transaldolase. The nucleotide sequence encoding for transketolase from is herein designated TAL1.

Xylose Isomerase or Xylose Reductase Genes

According to the invention, one or more copies of one or more xylose isomerase gene and/or one or more xylose reductase and xylitol dehydrogenase are introduced into the genome of the host cell. The presence of these genetic elements confers on the cell the ability to convert xylose by isomerisation or reduction.

In one embodiment, the one or more copies of one or more xylose isomerase gene are introduced into the genome of the host cell.

A "xylose isomerase" (EC 5.3.1.5) is herein defined as an enzyme that catalyses the direct isomerisation of D-xylose into D-xylulose and/or vice versa. The enzyme is also known as a D-xylose ketoisomerase. A xylose isomerase herein may also be capable of catalysing the conversion between D-glucose and D-fructose (and accordingly may therefore be referred to as a glucose isomerase). A xylose isomerase herein may require a bivalent cation, such as magnesium, manganese or cobalt as a cofactor.

Accordingly, such a transformed host cell is capable of isomerising xylose to xylulose. The ability of isomerising xylose to xylulose is conferred on the host cell by transformation of the host cell with a nucleic acid construct comprising a nucleotide sequence encoding a defined xylose isomerase. A transformed host cell isomerises xylose into xylulose by the direct isomerisation of xylose to xylulose.

The Xylose isomerase gene may have various origin, such as for example *Piromyces* sp. as disclosed in WO2006/009434. Other suitable origins are *Bacteroides*, in particular *Bacteroides uniformis* as described in PCT/EP2009/52623 In another embodiment, one or more copies of one or more xylose reductase and xylitol dehydrogenase genes are introduced into the genome of the host cell. In this embodiment the conversion of xylose is conducted in a two-step conversion of xylose into xylulose via a xylitol intermediate as catalyzed by xylose reductase and xylitol dehydrogenase, respectively. In an embodiment thereof xylose reductase (XR), xylitol dehydrogenase (XDH), and xylulokinase (XK) may be overexpressed, and optionally one or more of genes encoding NADPH producing enzymes are up-regulated and one or more of the genes encoding NADH consuming enzymes are up-regulated, as disclosed in WO 2004085627.

XKS1 Gene

A transformed host cell may comprise one or more genetic modifications that increase the specific xylulose kinase activity. Preferably the genetic modification or modifications causes overexpression of a xylulokinase, e.g. by overexpression of a nucleotide sequence encoding a xylulokinase. The gene encoding the xylulokinase may be endogenous to the host cell or may be a xylulokinase that is heterologous to the host cell. A nucleotide sequence used for overexpression of xylulokinase in the host cell is a nucleotide sequence encoding a polypeptide with xylulokinase activity.

The enzyme "xylulokinase" (EC 2.7.1.17) is herein defined as an enzyme that catalyses the reaction ATP+D-xylulose=ADP+D-xylulose 5-phosphate. The enzyme is also known as a phosphorylating xylulokinase, D-xylulokinaseor ATP:D-xylulose 5-phosphotransferase. A xylulokinase used in the invention may be further defined by its amino acid sequence. Likewise a xylulokinase may be defined by a nucleotide sequence encoding the enzyme as well as by a nucleotide sequence hybridising to a reference nucleotide sequence encoding a xylulokinase.

In a transformed host cell, a genetic modification or modifications that increase(s) the specific xylulokinase activity may be combined with any of the modifications increasing the flux of the pentose phosphate pathway as described above. This is not, however, essential.

In the host cells of the invention, a xylulokinase to be overexpressed is overexpressed by at least a factor of about 1.1, about 1.2, about 1.5, about 2, about 5, about 10 or about 20 as compared to a strain which is genetically identical except for the genetic modification(s) causing the overexpression. It is to be understood that these levels of overexpression may apply to the steady state level of the enzyme's activity, the steady state level of the enzyme's protein as well as to the steady state level of the transcript coding for the enzyme.

Aldose Reductase (GRE3) Gene Deletion

In the embodiment, where XI is used as gene to convert xylose, it may be advantageous to reduce aldose reductase activity. A transformed host cell may therefore comprise one or more genetic modifications that reduce aldose reductase activity in the host cell. Preferably, unspecific aldose reductase activity is reduced in the host cell by one or more genetic modifications that reduce the expression of or inactivates a gene encoding an unspecific aldose reductase. Preferably, the genetic modification(s) reduce or inactivate the expression of each endogenous copy of a gene encoding an aldose reductase in the host cell, in an embodiment GRE3 aldose reductase deletion (herein called GRE3 deletion). Transformed host cells may comprise multiple copies of genes encoding unspecific aldose reductases as a result of di-, poly- or aneuploidy, and/or the host cell may contain several different (iso)enzymes with aldose reductase activity that differ in amino acid sequence and that are each encoded by a different gene. Also in such instances preferably the expression of each gene that encodes an unspecific aldose reductase is reduced or inactivated. Preferably, the gene is inactivated by deletion of at least part of the gene or by disruption of the gene, whereby in this context the term gene also includes any non-coding sequence up- or down-stream of the coding sequence, the (partial) deletion or inactivation of which results in a reduction of expression of unspecific aldose reductase activity in the host cell.

A nucleotide sequence encoding an aldose reductase whose activity is to be reduced in the host cell is a nucleotide sequence encoding a polypeptide with aldose reductase activity.

Thus, a host cell comprising only a genetic modification or modifications that reduce(s) unspecific aldose reductase activity in the host cell is specifically included in the invention.

The enzyme "aldose reductase" (EC 1.1.1.21) is herein defined as any enzyme that is capable of reducing xylose or xylulose to xylitol. In the context of the present invention an aldose reductase may be any unspecific aldose reductase that is native (endogenous) to a host cell of the invention and that is capable of reducing xylose or xylulose to xylitol. Unspecific aldose reductases catalyse the reaction:

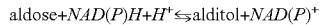

$$\text{aldose} + NAD(P)H + H^+ \leftrightarrows \text{alditol} + NAD(P)^+$$

The enzyme has a wide specificity and is also known as aldose reductase; polyol dehydrogenase (NADP+); alditol:NADP oxidoreductase; alditol:NADP+1-oxidoreductase; NADPH-aldopentose reductase; or NADPH-aldose reductase.

A particular example of such an unspecific aldose reductase that is endogenous to *S. cerevisiae* and that is encoded by the GRE3 gene (Traff et al., 2001, Appl. Environ. Microbiol. 67: 5668-74). Thus, an aldose reductase of the invention may be further defined by its amino acid sequence. Likewise an aldose reductase may be defined by the nucleotide sequences encoding the enzyme as well as by a nucleotide sequence hybridising to a reference nucleotide sequence encoding an aldose reductase.

Bioproducts Production

Over the years suggestions have been made for the introduction of various organisms for the production of bio-ethanol from crop sugars. In practice, however, all major bio-ethanol production processes have continued to use the yeasts of the genus *Saccharomyces* as ethanol producer. This is due to the many attractive features of *Saccharomyces* species for industrial processes, i.e., a high acid-, ethanol- and osmo-tolerance, capability of anaerobic growth, and of course its high alcoholic fermentative capacity. Preferred yeast species as host cells include *S. cerevisiae, S. bulderi, S. barnetti, S. exiguus, S. uvarum, S. diastaticus, K. lactis, K. marxianus* or *K. fragilis*.

A transformed host cell may be a cell suitable for the production of ethanol. A transformed host cell may, however, be suitable for the production of fermentation products other than ethanol Such non-ethanolic fermentation products include in principle any bulk or fine chemical that is producible by a eukaryotic microorganism such as a yeast or a filamentous fungus.

A transformed host cell that may be used for production of non-ethanolic fermentation products is a host cell that contains a genetic modification that results in decreased alcohol dehydrogenase activity.

In an embodiment the transformed host cell may be used in a process wherein sugars originating from lignocellulose are converted into ethanol.

Lignocellulose

Lignocellulose, which may be considered as a potential renewable feedstock, generally comprises the polysaccharides cellulose (glucans) and hemicelluloses (xylans, heteroxylans and xyloglucans). In addition, some hemicellulose may be present as glucomannans, for example in wood-derived feedstocks. The enzymatic hydrolysis of these polysaccharides to soluble sugars, including both monomers and multimers, for example glucose, cellobiose, xylose, arabinose, galactose, fructose, mannose, rhamnose, ribose, galacturonic acid, glucuronic acid and other hexoses and pentoses occurs under the action of different enzymes acting in concert.

In addition, pectins and other pectic substances such as arabinans may make up considerably proportion of the dry mass of typically cell walls from non-woody plant tissues (about a quarter to half of dry mass may be pectins).

Pretreatment

Before enzymatic treatment, the lignocellulosic material may be pretreated. The pretreatment may comprise exposing the lignocellulosic material to an acid, a base, a solvent, heat, a peroxide, ozone, mechanical shredding, grinding, milling or rapid depressurization, or a combination of any two or more thereof. This chemical pretreatment is often combined with heat-pretreatment, e.g. between 150-220° C. for 1 to 30 minutes.

Enzymatic Hydrolysis

The pretreated material is commonly subjected to enzymatic hydrolysis to release sugars that may be fermented according to the invention. This may be executed with conventional methods, e.g. contacting with cellulases, for instance cellobiohydrolase(s), endoglucanase(s), beta-glucosidase(s) and optionally other enzymes. The conversion with the cellulases may be executed at ambient temperatures or at higher tempatures, at a reaction time to release sufficient amounts of sugar(s). The result of the enzymatic hydrolysis is hydrolysis product comprising C5/C6 sugars, herein designated as the sugar composition.

The Sugar Composition

The sugar composition according to the invention comprises glucose, arabinose and xylose. Any sugar composition may be used in the invention that suffices those criteria. Optional sugars in the sugar composition are galactose and mannose. In a preferred embodiment, the sugar composition is a hydrolysate of one or more lignocellulosic material. Lignocelllulose herein includes hemicellulose and hemicellulose parts of biomass. Also lignocellulose includes lignocellulosic fractions of biomass. Suitable lignocellulosic materials may be found in the following list: orchard primings, chaparral, mill waste, urban wood waste, municipal waste, logging waste, forest thinnings, short-rotation woody crops, industrial waste, wheat straw, oat straw, rice straw, barley straw, rye straw, flax straw, soy hulls, rice hulls, rice straw, corn gluten feed, oat hulls, sugar cane, corn stover, corn stalks, corn cobs, corn husks, switch grass, miscanthus, sweet sorghum, canola stems, soybean stems, prairie grass, gamagrass, foxtail; sugar beet pulp, citrus fruit pulp, seed hulls, cellulosic animal wastes, lawn clippings, cotton, seaweed, trees, softwood, hardwood, poplar, pine, shrubs, grasses, wheat, wheat straw, sugar cane bagasse, corn, corn husks, corn hobs, corn kernel, fiber from kernels, products and by-products from wet or dry milling of grains, municipal solid waste, waste paper, yard waste, herbaceous material, agricultural residues, forestry residues, municipal solid waste, waste paper, pulp, paper mill residues, branches, bushes, canes, corn, corn husks, an energy crop, forest, a fruit, a flower, a grain, a grass, a herbaceous crop, a leaf, bark, a needle, a log, a root, a sapling, a shrub, switch grass, a tree, a vegetable, fruit peel, a vine, sugar beet pulp, wheat midlings, oat hulls, hard or soft wood, organic waste material generated from an agricultural process, forestry wood waste, or a combination of any two or more thereof.

An overview of some suitable sugar compositions derived from lignocellulose and the sugar composition of their hydrolysates is given in table 2. The listed lignocelluloses include: corn cobs, corn fiber, rice hulls, melon shells, sugar beet pulp, wheat straw, sugar cane bagasse, wood, grass and olive pressings.

TABLE 2

Overview of sugar compositions from lignocellulosic materials.

| Lignocellulosic material | Gal | Xyl | Ara | Man | Glu | Rham | Sum | % Gal. |
|---|---|---|---|---|---|---|---|---|
| Corn cob a | 10 | 286 | 36 | | 227 | 11 | 570 | 1.7 |
| Corn cob b | 131 | 228 | 160 | | 144 | | 663 | 19.8 |
| Rice hulls a | 9 | 122 | 24 | 18 | 234 | 10 | 417 | 2.2 |
| Rice hulls b | 8 | 120 | 28 | | 209 | 12 | 378 | 2.2 |
| Melon Shells | 6 | 120 | 11 | | 208 | 16 | 361 | 1.7 |
| Sugar beet pulp | 51 | 17 | 209 | 11 | 211 | 24 | 523 | 9.8 |
| Wheat straw Idaho | 15 | 249 | 36 | | 396 | | 696 | 2.2 |
| Corn fiber | 36 | 176 | 113 | | 372 | | 697 | 5.2 |
| Cane Bagasse | 14 | 180 | 24 | 5 | 391 | | 614 | 2.3 |
| Corn stover | 19 | 209 | 29 | | 370 | | 626 | |
| Athel (wood) | 5 | 118 | 7 | 3 | 493 | | 625 | 0.7 |
| *Eucalyptus* (wood) | 22 | 105 | 8 | 3 | 445 | | 583 | 3.8 |
| CWR (grass) | 8 | 165 | 33 | | 340 | | 546 | 1.4 |
| JTW (grass) | 7 | 169 | 28 | | 311 | | 515 | 1.3 |
| MSW | 4 | 24 | 5 | 20 | 440 | | 493 | 0.9 |
| Reed Canary Grass Veg | 16 | 117 | 30 | 6 | 209 | 1 | 379 | 4.2 |
| Reed Canary Grass Seed | 13 | 163 | 28 | 6 | 265 | 1 | 476 | 2.7 |
| Olive pressing residu | 15 | 111 | 24 | 8 | 329 | | 487 | 3.1 |

Gal = galactose, Xyl = xylose, Ara = arabinose, Man = mannose, Glu = glucose, Rham = rhamnose.
The percentage galactose (% Gal) is given.

It is clear from table 2 that in these lignocelluloses a high amount of sugar is presence in de form of glucose, xylose, arabinose and galactose. The conversion of glucose, xylose, arabinose and galactose to fermentation product is thus of great economic importance. Also mannose is present in some lignocellulose materials be it usually in lower amounts than the previously mentioned sugars. Advantageously therefore also mannose is converted by the transformed host cell.

Fermentation

The fermentation process may be an aerobic or an anaerobic fermentation process. An anaerobic fermentation process is herein defined as a fermentation process run in the absence of oxygen or in which substantially no oxygen is consumed, preferably less than about 5, about 2.5 or about 1 mmol/L/h, more preferably 0 mmol/L/h is consumed (i.e. oxygen consumption is not detectable), and wherein organic molecules serve as both electron donor and electron acceptors. In the absence of oxygen, NADH produced in glycolysis and biomass formation, cannot be oxidised by oxidative phosphorylation. To solve this problem many microorganisms use pyruvate or one of its derivatives as an electron and hydrogen acceptor thereby regenerating $NAD^+$.

Thus, in a preferred anaerobic fermentation pentose is converted into fermentation products such as ethanol, butanol, lactic acid, 3-hydroxy-propionic acid, acrylic acid, acetic acid, succinic acid, citric acid, malic acid, fumaric acid, an amino acid, 1,3-propane-diol, ethylene, glycerol, a β-lactam antibiotic and a cephalosporin.

The fermentation process is preferably run at a temperature that is optimal for the cell. Thus, for most yeasts or fungal host cells, the fermentation process is performed at a temperature which is less than about 42° C., preferably less than about 38° C. For yeast or filamentous fungal host cells, the fermentation process is preferably performed at a temperature which is lower than about 35, about 33, about 30 or about 28° C. and at a temperature which is higher than about 20, about 22, or about 25° C.

The ethanol yield on xylose and/or glucose in the process preferably is at least about 50, about 60, about 70, about 80, about 90, about 95 or about 98%. The ethanol yield is herein defined as a percentage of the theoretical maximum yield.

The invention also relates to a process for producing a fermentation product.

The fermentation process according to the present invention may be run under aerobic and anaerobic conditions. In an embodiment, the process is carried out under microaerophilic or oxygen limited conditions.

An anaerobic fermentation process is herein defined as a fermentation process run in the absence of oxygen or in which substantially no oxygen is consumed, preferably less than about 5, about 2.5 or about 1 mmol/L/h, and wherein organic molecules serve as both electron donor and electron acceptors.

In a preferred process the cell ferments both the xylose and glucose, preferably simultaneously in which case preferably a cell is used which is insensitive to glucose repression. In addition to a source of xylose (and glucose) as carbon source, the fermentation medium will further comprise the appropriate ingredient required for growth of the cell. Compositions of fermentation media for growth of microorganisms such as yeasts are well known in the art The fermentation processes may be carried out in batch, fed-batch or continuous mode. A separate hydrolysis and fermentation (SHF) process or a simultaneous saccharification and fermentation (SSF) process may also be applied. A combination of these fermentation process modes may also be possible for optimal productivity. These processes are described hereafter in more detail.

SSF Mode

For Simultaneous Saccharification and Fermentation (SSF) mode, the reaction time for liquefaction/hydrolysis or presaccharification step is dependent on the time to realize a desired yield, i.e. cellulose to glucose conversion yield. Such yield is preferably as high as possible, preferably 60% or more, 65% or more, 70% or more, 75% or more 80% or more, 85% or more, 90% or more, 95% or more, 96% or more, 97% or more, 98% or more, 99% or more, even 99.5% or more or 99.9% or more.

According to the invention very high sugar concentrations in SHF mode and very high product concentrations (e.g. ethanol) in SSF mode are realized. In SHF operation the glucose concentration is 25 g/L or more, 30 g/L or more, 35 g/L or more, 40 g/L or more, 45 g/L or more, 50 g/L or more, 55 g/L or more, 60 g/L or more, 65 g/L or more, 70 g/L or more, 75 g/L or more, 80 g/L or more, 85 g/L or more, 90 g/L or more, 95 g/L or more, 100 g/L or more, 110 g/L or more, 120 g/L or more or may e.g. be 25 g/L-250 g/L, 30 gl/L-200 g/L, 40 g/L-200 g/L, 50 g/L-200 g/L, 60 g/L-200 g/L, 70 g/L-200 g/L, 80 g/L-200 g/L, 90 g/L, 80 g/L-200 g/L.

Product Concentration in SSF Mode

In SSF operation, the product concentration (g/L) is dependent on the amount of glucose produced, but this is not visible since sugars are converted to product in the SSF, and product concentrations can be related to underlying glucose concentration by multiplication with the theoretical maximum yield (Yps max in gr product per gram glucose)

The theoretical maximum yield (Yps max in gr product per gram glucose) of a fermentation product can be derived from textbook biochemistry. For ethanol, 1 mole of glucose (180 gr) yields according to normal glycolysis fermentation pathway in yeast 2 moles of ethanol (=2×46=92 gr ethanol. The theoretical maximum yield of ethanol on glucose is therefore 92/180=0.51 gr ethanol/gr glucose.

For Butanol (MW 74 gr/mole) or iso butanol, the theoretical maximum yield is 1 mole of butanol per mole of glucose. So Yps max for (iso-)butanol=74/180=0.41 gr (iso-)butanol/gr glucose.

For lactic acid the fermentation yield for homolactic fermentation is 2 moles of lactic acid (MW=90 gr/mole) per mole of glucose. According to this stoichiometry, the Yps max=1 gr lactic acid/gr glucose.

For other fermentation products a similar calculation may be made.

SSF Mode

In SSF operation the product concentration is 25 g*Yps g/L/L or more, 30*Yps g/L or more, 35 g*Yps/L or more, 40*Yps g/L or more, 45*Yps g/L or more, 50*Yps g/L or more, 55*Yps g/L or more, 60*Yps g/L or more, 65*Yps g/L or more, 70*Yps g/L or more, 75*Yps g/L or more, 80*Yps g/L or more, 85*Yps g/L or more, 90*Yps g/L or more, 95*Yps g/L or more, 100*Yps g/L or more, 110*Yps g/L or more, 120 g/L*Yps or more or may e.g. be 25*Yps g/L-250*Yps g/L, 30*Yps gl/L-200*Yps g/L, 40*Yps g/L-200*Yps g/L, 50*Yps g/L-200*Yps g/L, 60*Yps g/L-200*Yps g/L, 70*Yps g/L-200*Yps g/L, 80*Yps g/L-200*Yps g/L, 90*Yps g/L, 80*Yps g/L-200*Yps g/L Accordingly, the invention provides a method for the preparation of a fermentation product, which method comprises:
  a. degrading lignocellulose using a method as described herein; and
  b. fermenting the resulting material, thereby to prepare a fermentation product.

Fermentation Product

The fermentation product of the invention may be any useful product. In one embodiment, it is a product selected from the group consisting of ethanol, n-butanol, isobutanol, lactic acid, 3-hydroxy-propionic acid, acrylic acid, acetic acid, succinic acid, fumaric acid, malic acid, itaconic acid, maleic acid, citric acid, adipic acid, an amino acid, such as lysine, methionine, tryptophan, threonine, and aspartic acid, 1,3-propane-diol, ethylene, glycerol, a β-lactam antibiotic and a cephalosporin, vitamins, pharmaceuticals, animal feed supplements, specialty chemicals, chemical feedstocks, plastics, solvents, fuels, including biofuels and biogas or organic polymers, and an industrial enzyme, such as a protease, a cellulase, an amylase, a glucanase, a lactase, a lipase, a lyase, an oxidoreductases, a transferase or a xylanase. For example the fermentation products may be produced by cells according to the invention, following prior art cell preparation methods and fermentation processes, which examples however should herein not be construed as limiting. n-butanol may be produced by cells as described in WO2008121701 or WO2008086124; lactic acid as described in US2011053231 or US2010137551; 3-hydroxy-propionic acid as described in WO2010010291; acrylic acid as described in WO2009153047.

Recovery of the Fermentation Product

For the recovery of the fermentation product existing technologies are used. For different fermentation products different recovery processes are appropriate. Existing methods of recovering ethanol from aqueous mixtures commonly use fractionation and adsorption techniques. For example, a beer still can be used to process a fermented product, which contains ethanol in an aqueous mixture, to produce an enriched ethanol-containing mixture that is then subjected to fractionation (e.g., fractional distillation or other like techniques). Next, the fractions containing the highest concentrations of ethanol can be passed through an adsorber to remove most, if not all, of the remaining water from the ethanol.

The following Examples illustrate the invention:

EXAMPLES

General Molecular Biology Techniques

Unless indicated otherwise, the methods used are standard biochemical techniques. Examples of suitable general methodology textbooks include Sambrook et al., Molecular Cloning, a Laboratory Manual (1989) and Ausubel et al., Current Protocols in Molecular Biology (1995), John Wiley & Sons, Inc.

Media

The media used in the experiments was either YEP-medium (10 g/l yeast extract, 20 g/l peptone) or solid YNB-medium (6.7 g/l yeast nitrogen base, 15 g/l agar), supplemented with sugars as indicated in the examples. For solid YEP medium, 15 g/l agar was added to the liquid medium prior to sterilization.

In the AFM experiments, Mineral Medium was used. The composition of Mineral Medium has been described by Verduyn et al. (Yeast (1992), Volume 8, 501-517) and was supplemented with 2,325 g/l urea and sugars as indicated in the examples.

Transformation of Yeast Cells

Yeast transformation was done according to the method described by Schiestl and Gietz (Current Genetics (1989), Volume 16, 339-346).

Colony PCR

Genomic DNA was extracted from single yeast colonies for PCR according to the method described by Lõoke et al. (BioTechniques (2011), Volume 50, 325-328).

AFM Procedure

The Alcohol Fermentation Monitor (AFM; Halotec, Veenendaal, the Netherlands) is a robust and user-friendly laboratory parallel bioreactor that allows for accurate comparisons of carbon conversion rates and yields for six simultaneous anaerobic fermentations.

The starting culture of the AFM experiment contained 50 mg of yeast (dry weight). To determine this, a calibration curve was made of the RN1001 strain of biomass vs. OD700. This calibration curve was used in the experiment to determine the volume of cell culture needed for 50 mg of yeast (dry weight).

Prior to the start of the AFM experiment, precultures were grown as indicated in the examples. For each strain the $OD_{700}$ was measured and 50 mg of yeast (dry weight) was inoculated in 400 ml Mineral Medium (Verduyn et al. (Yeast (1992), Volume 8, 501-517), supplemented with 2,325 g/l urea and sugars as indicated in the examples.

RNA Isolation

RNA was isolated using the Nucleospin RNA II kit (Machery-Nagel, GmbH & Co. KG, Düren, Germany), with a slightly adapted manufacturer's protocol. Prior to the start of the protocol the freshly grown yeast cells were treated in 0.2 mg lyticase/ml, 1M Sorbitol and 0.1M EDTA buffer for 30 minutes at 30° C. After this step, the manufacturers protocol was carried out, with exception of step 6 and 7 (desalting of silica membrane and the DNase treatment). To remove genomic DNA, a DNase treatment was carried out after elution of the RNA from the column. For this 10 μl RNA solution was mixed with 7 μl DNase and RNase free water, 2 μl 10× buffer and 1 μl DNase (Fermentas, 68789 St.

Leon-Rot/Germany). This mix was incubated for 30 minutes at 37° C. For inactivation of the enzyme, 1 µl 25 mM EDTA (Fermentas, 68789 St. Leon-Rot/Germany) was added and incubated for 10 minutes at 65° C.

cDNA Synthesis cDNA synthesis was performed on the RNA using the RevertAid™ H Minus First Strand cDNA Synthesis Kit (Fermentas, 68789 St. Leon-Rot/Germany).

Q-PCR

For the Q-PCR experiment the DyNAmo Colorflash SYBR Green qPCR kit (Finnzymes, 01620 Vantaa, Finland) was used. A DNA mix was made with 1 hl cDNA, 39 µl H$_2$O and 10 µl yellow sample dye. For each reaction 5 µl DNA mix was used with 10 IA 2x DyNAmo mastermix, 7 µl H$_2$O, 1 µl 10 µM forward primer and 1 µl 10 µM reverse primer (primer numbers are indicated in the examples). The Q-PCR was run on the Bio-Rad CFX96 Real-Time system (Bio-Rad, Hercules, Calif., USA), using the program as indicated in Table 3.

TABLE 3

Q-PCR program
PROGRAM 95.0° C. for 5:00
95.0° C. for 0:20
67.0° C. for 0:20
72.0° C. for 0:20
+Plate Read
GOTO 2, 49 more times
Melt Curve 65.0 to 95.0° C., increment 0.5° C., 0:05 + Plate Read
END Strains The strains used in the experiments are RN1001, RN1041 and RN1216. RN1041 has been described in WO 2012067510. This strain has the following genotype:

MAT a, ura3-52, leu2-112, his3::loxP, gre3::loxP, loxP-pTPI1::TAL1, loxP-pTP11::RK/1, loxP-pTP11-TKL1, loxP-pTP11-RPE1, delta::pADH1-XKS1-tCYC1-LEU2, delta::URA3-pTPI1-xylA-tCYC1

MAT a=Mating Type a ura3-52, leu2-112, H/S3::loxP mutations in the URA3, LEU2 and HIS3 genes respectively. The ura3-52 mutation is complemented by the URA3 gene on the xylA overexpression construct; the leu2-112 mutation is complemented by the LEU2 gene on the XKS1 overexpression construct. The deletion of the H/S3-gene causes a histidine auxotrophy. For this reason, RN1041 needs histidine in the medium for growth. gre3::loxP is a deletion of the GRE3 gene, encoding aldose reductase. The loxP site is left behind in the genome after marker removal.

loxP-pTPI1 designates the overexpression of genes of, in the experiments described herein, the non-oxidative pentose phosphate pathway by replacement of the native promoter by the promoter of the TPI1 gene. The loxP site upstream of the strong, constitutive TP/1 promoter remains in the genome after marker removal (Kuyper et al, FEMS Yeast Research 5 (2005) 925-934).

delta::means chromosomal integration of the construct after recombination on the long terminal repeats of the Ty1 retrotransposon.

Strain RN1001 is the parent strain of strain RN1041, i.e. before deletion of the H/S3-gene.

Strain RN1216 has the same genotype as strain RN1041.

Example 1

Construction of a Glyoxalase Overexpression Plasmid

The GLO1 ORF was obtained from CEN.PK113-7D using primers SEQ ID NO 25 and SEQ ID NO 26. Subsequently the PCR amplified GLO1 ORF was cloned in a TOPO blunt vector using the Zero Blunt® TOPO® PCR Cloning kit (Invitrogen, Carlsbad, Calif., USA) and transformed to One Shot® TOP10 chemically competent *E. coli* (Invitrogen, Carlsbad, Calif., USA). Miniprep DNA isolations were performed on several colonies. The obtained plasmids were checked by restriction enzyme analyses. The correct plasmid was called pRN935.

Figure 2:
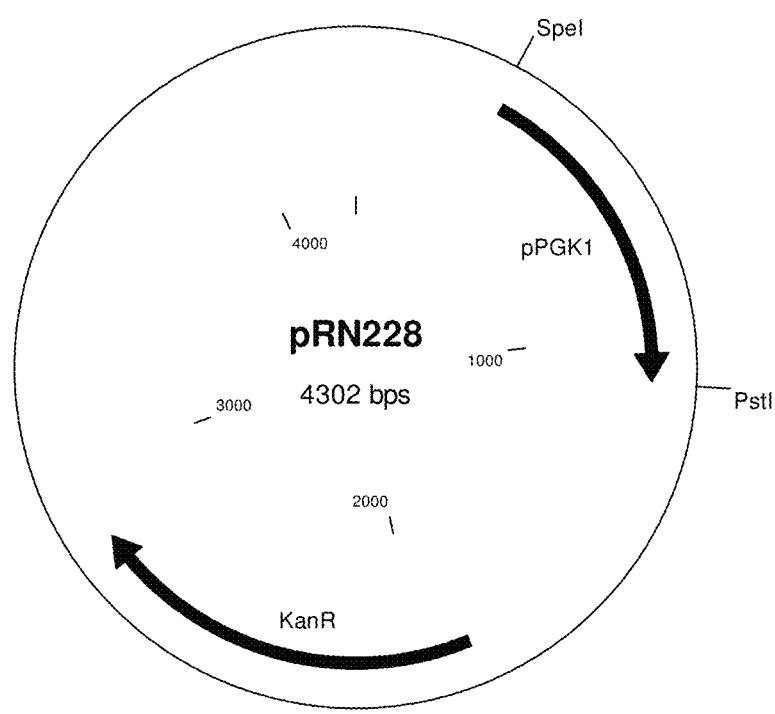
FIG. 2: Map of plasmid pRN228 (see examples)
Figure 3:
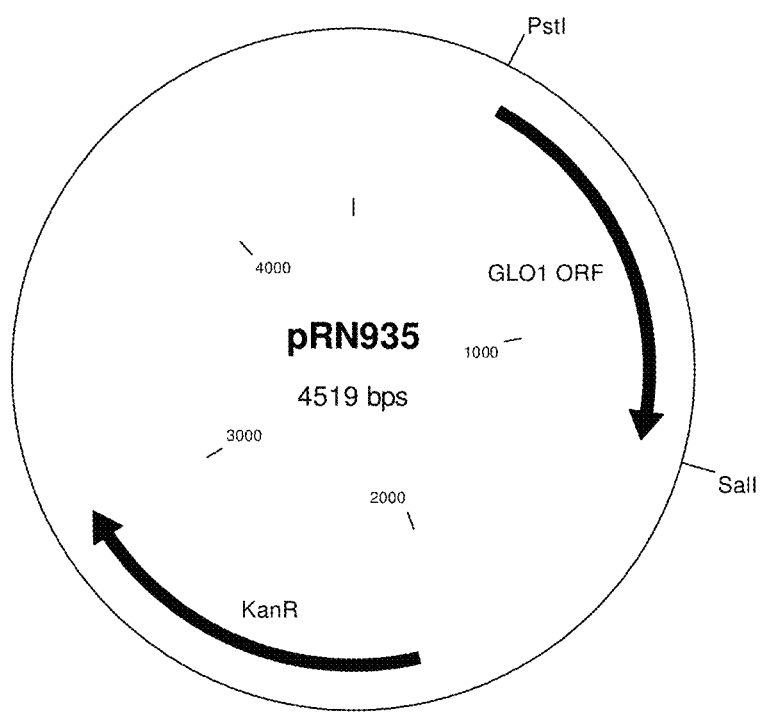
FIG. 3: Map of plasmid pRN935 (see examples)
Figure 4:
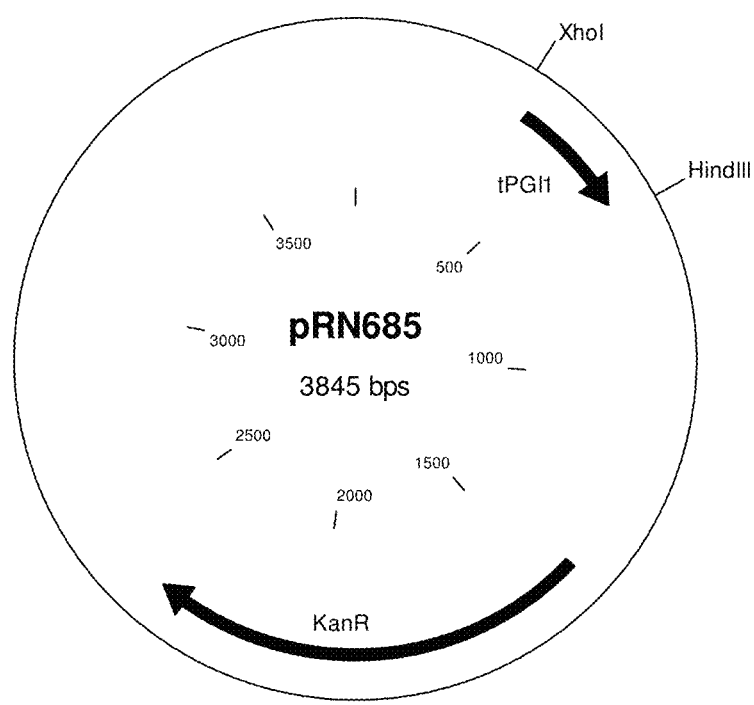
FIG. 4: Map of plasmid pRN685 (see examples)
Figure 5:
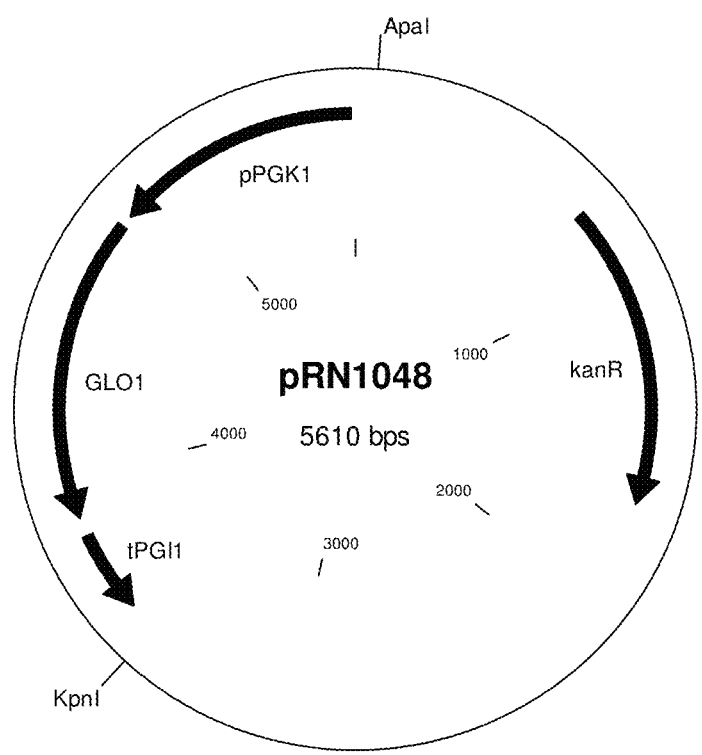
FIG. 5: Map of plasmid pRN1048 (see examples)
Figure 7:
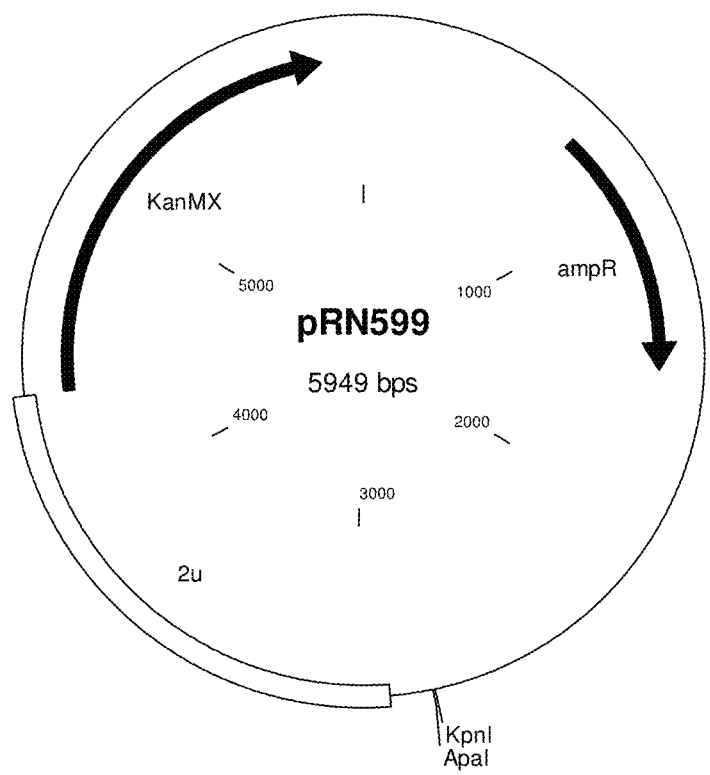
FIG. 7: Map of yeast shuttle vector pRN599 (see examples)
Figure 8:
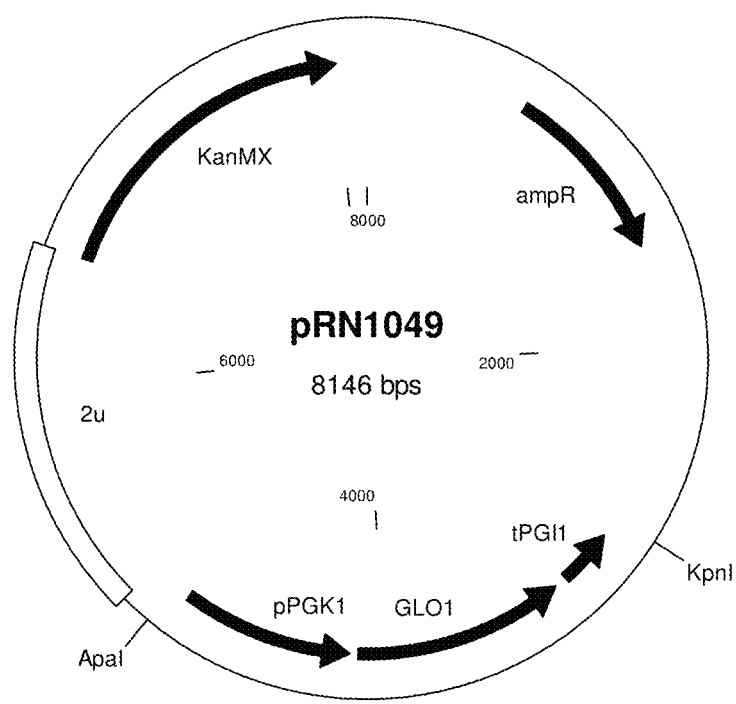
FIG. 8: Map of plasmid pRN1049.

Overexpression of GLO1 was carried out on a 2µ plasmid. Therefore a 2µ plasmid with the GLO1 expression cassette was constructed. The construction of the GLO1 expression cassette with the PGK1 promoter and PGI1 terminator is shown in FIG. 1. Physical maps of the plasmids containing these three elements, present in plasmids pRN228, pRN935 and pRN685, are given in FIGS. 2, 3 and 4 respectively. Subsequently the constructed GLO1 expression cassette was PCR amplified using primers SEQ ID NO 1 (pPGK1-5'-F; FIG. 1) and SEQ ID NO 2 (tPGI1-3'-R; FIG. 1). The PCR product was purified over column by using the GeneJET™ Gel Extraction kit (Fermentas, 68789 St. Leon-Rot/Germany), cloned in a TOPO blunt vector using the Zero Blunt® TOPO® PCR Cloning kit (Invitrogen, Carlsbad, Calif., USA) and transformed to One Shot® TOP10 chemically competent *E. coli* (Invitrogen, Carlsbad, Calif., USA). Miniprep DNA isolations were performed on several colonies. The obtained plasmids were checked by restriction enzyme analyses. Two different plasmids were obtained, one plasmid with the GLO1 expression cassette inserted in reverse orientation (pRN1048, FIG. 5) and one plasmid with the GLO1 expression cassette inserted in forward orientation (pRN1129, FIG. 6). Subsequently the GLO1 expression cassette, from pRN1048, was cloned into the yeast shuttle vector pRN599 (FIG. 7) between the KpnI and ApaI sites. The resulting plasmid was transformed to One Shot® TOP10 chemically competent *E. coli* (Invitrogen, Carlsbad, Calif., USA). Miniprep DNA isolations were performed on several colonies. The obtained plasmids were checked by restriction enzyme analyses. The correct plasmid was called pRN1049 (FIG. 8).

Plasmid pRN228 contains the following relevant elements: the PGK1 promoter flanked by restriction sites SpeI and PstI and a kanamycin resistance marker.

Plasmid pRN935 contains the following relevant elements: the GLO1 ORF flanked by restriction sites PstI and SalI and a kanamycin resistance marker.

Plasmid pRN685 contains the following relevant elements: the PGI1 terminator flanked by restriction sites XhoI and HindIII and a kanamycin resistance marker.

Plasmid pRN599 contains the following relevant elements: a 2µ origin of replication followed by a kanMX marker (consisting of an *Ashbya gossypii* TEF1 promoter, a KanMX resistance gene and the *Ashbya gossypii* TEF1 terminator) and an ampicillin resistance marker.

Primer SEQ ID NO 1 is the forward primer of the PGK1 promoter.

Primer SEQ ID NO 2 is the reverse primer of the PGI1 terminator.

Primer SEQ ID NO 25 is the forward primer for amplification of the GLO1 gene.

Primer SEQ ID NO 26 is the reverse primer for amplification of the GLO1 gene.

Example 2

Transformation of Yeast Strain with Overexpression Plasmid

The constructed GLO1 overexpression plasmid pRN1049 was used to transform the yeast strain RN1001. Also a control strain was created by transforming the yeast strain RN1001 with the empty plasmid pRN599. Correct transformants were selected on YEP plates containing 2% glucose and 200 µg/ml G418. The RN1001 strain containing pRN1049 is named RN1001Gpl. The control strain RN1001 containing the empty plasmid pRN599 is named RN1001Epl.

Figure 9:
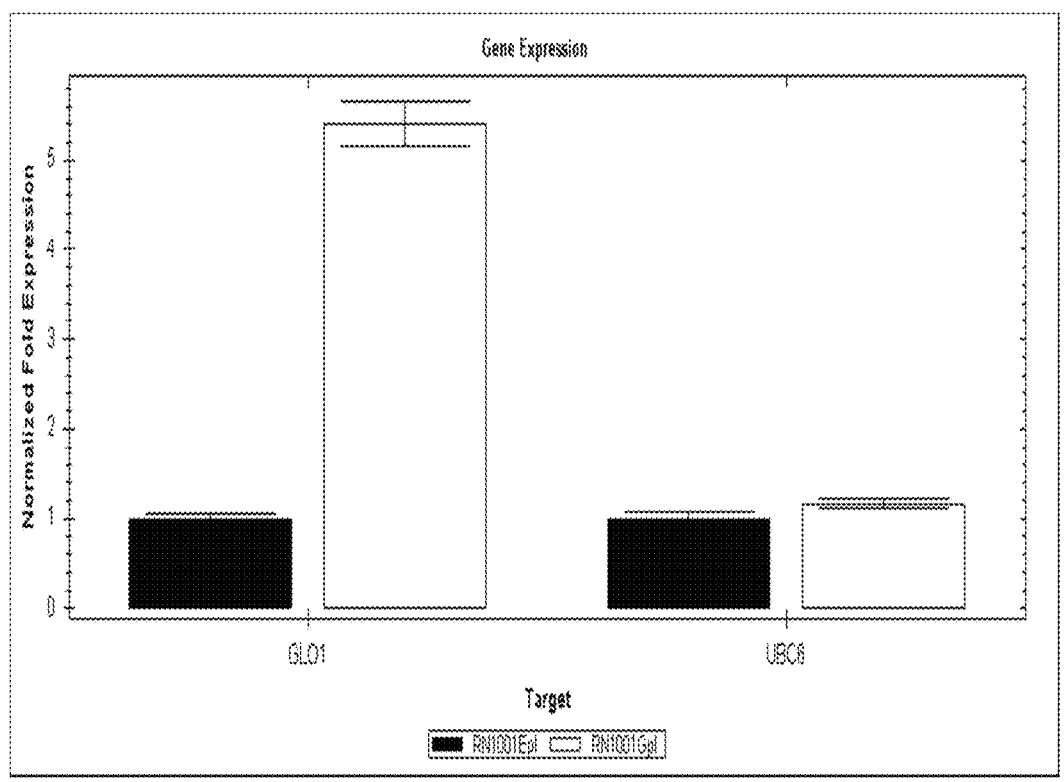
FIG. 9: Gene expression data. Normalized Fold Expression for Strains RN1001Epl and RN1001Gpl.

The level of GLO1 expression in RN1001Gpl was determined with Q-PCR. The control strain RN1001Epl was used as a reference. For this experiment both strains were grown overnight in YEP medium containing 2% glucose and 200 µg/ml G418. Subsequently RNA was isolated from the cultures and was checked for genomic DNA contamination by PCR using primers SEQ ID NO 3 and SEQ ID NO 4. No contamination was found. Then a cDNA synthesis was performed on the RNA using the RevertAid kit (Fermentas, 68789 St. Leon-Rot/Germany). Next a Q-PCR experiment was done with primers SEQ ID NO 5 and SEQ ID NO 6. Two housekeeping genes were used as a reference, ALG9 using primers SEQ ID NO 7 and SEQ ID NO 8 and UBC6 using primers SEQ ID NO 9 and SEQ ID NO 10. The GLO1 expression data was normalized on the housekeeping gene with the best duplo CT-values, in this case ALG9. The RN1001Gpl strain showed a higher expression of GLO1 as compared to RN1001Epl (FIG. 9). As indicated in FIG. 9, the normalized expression level of the GLO1-gene was about 5 times higher in strain RN1001Gpl as compared to RN1001Epl, while the normalized expression of the UBC6-gene was the same in both strains Primer SEQ ID NO 3 is identical to a sequence of the ACT1 gene.

Primer SEQ ID NO 4 is identical to a sequence of the ACT1 gene.

Primer SEQ ID NO 5 is identical to a sequence of the GLO1 gene.

Primer SEQ ID NO 6 is identical to a sequence of the GLO1 gene.

Primer SEQ ID NO 7 is identical to a sequence of the ALG9 gene.

Primer SEQ ID NO 8 is identical to a sequence of the ALG9 gene.

Primer SEQ ID NO 9 is identical to a sequence of the UBC6 gene.

Primer SEQ ID NO 10 is identical to a sequence of the UBC6 gene.

Example 3

AFM Experiments

After verification of higher GLO1 expression in RN1001Gpl as compared to the control strain RN1001Epl by Q-PCR (Example 2), an AFM experiment was started to determine the conversion rate of the presented sugars to ethanol by measuring the $CO_2$ production during the experiment, since ethanol and $CO_2$ are being produced in equimolar amounts. During the experiment, HPLC samples of the cultures were taken at different time points, in order to determine the glucose and xylose consumption rate and the ethanol production rate.

Precultures were made of both strains, by inoculating some cell material from agar plate in 100 ml YEP containing 2% glucose and 200 µg/ml G418. The next day, 400 ml Mineral Medium containing 2% glucose and 2% xylose was inoculated with cell material from the precultures. No G418 was added to the Mineral Medium in the AFM experiment.

Figure 10:
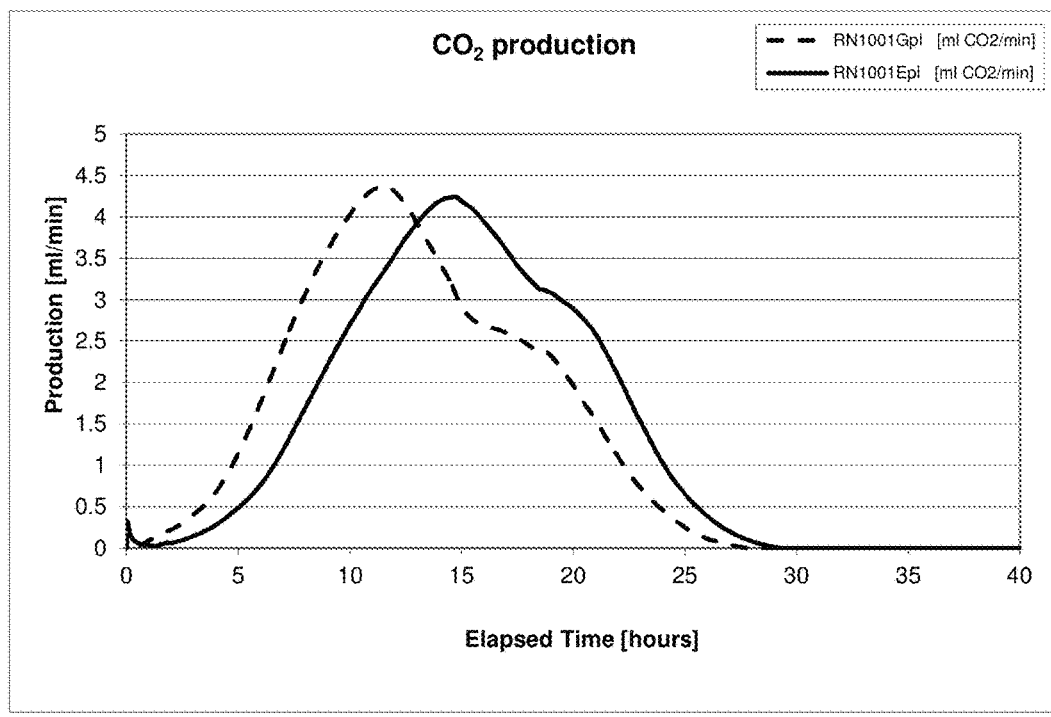
FIG. 10: $CO_2$ production curve for growth of strains RN1001Gpl (top) and RN1001Epl (bottom)
Figure 11:
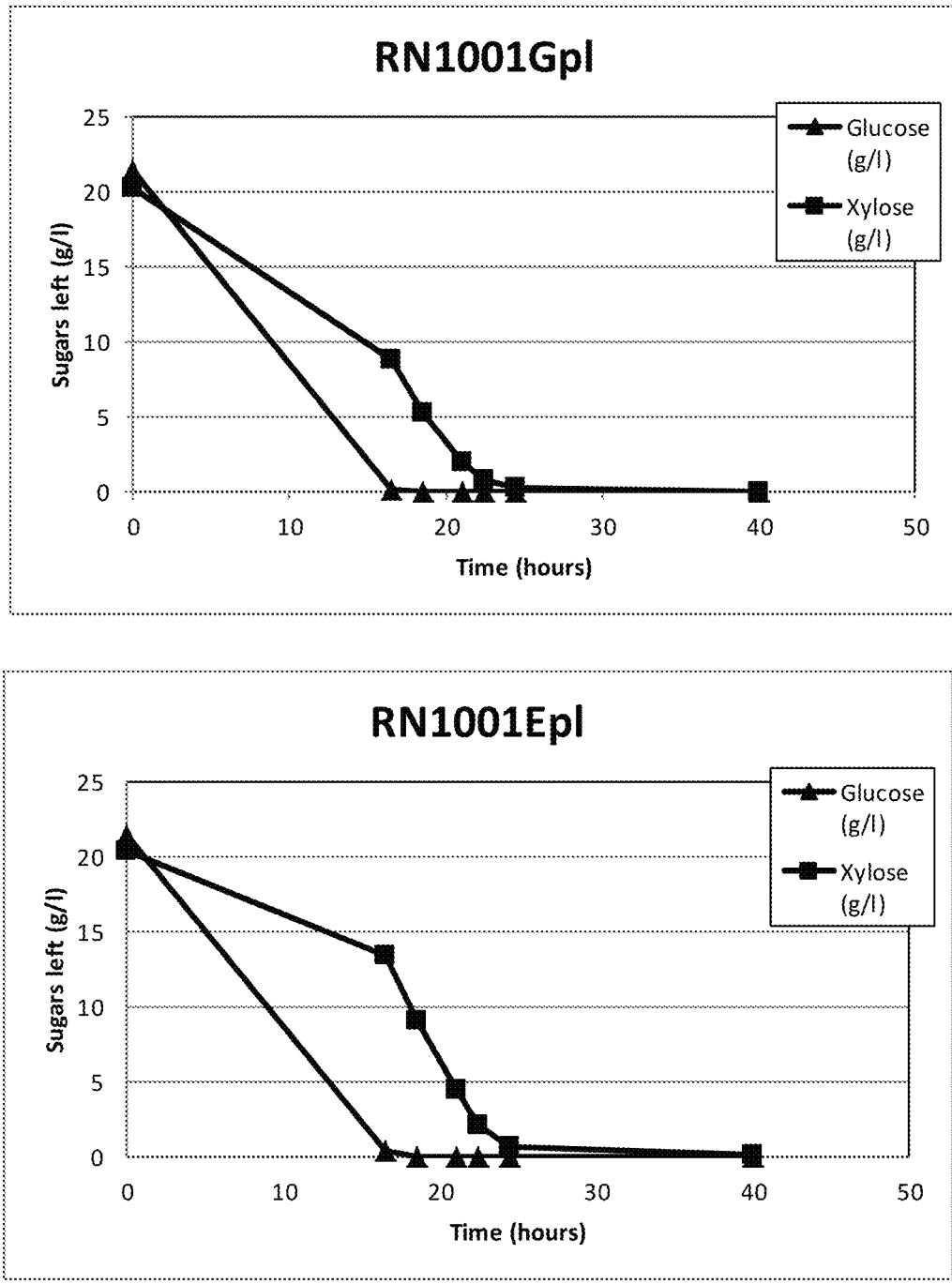
FIG. 11: Growth curve of strains RN1001Epl and RN1001Gpl showing sugar consumption.

The $CO_2$ production curves (FIG. 10) exhibit a faster and higher $CO_2$ production rate in RN1001Gpl as compared to RN1001Epl, indicating a faster glucose and xylose consumption in the RN1001Gpl as compared to the control strain RN1001Epl. HPLC data (Tables 4 and 5, and FIG. 11) confirmed faster xylose consumption rates in the RN1001Gpl strain as compared to the RN1001Epl strain. The glucose was already consumed at the second timepoint (16.5 hours), while this was not the case in strain RN1001 Epl.

TABLE 4

HPLC data RN1001Gpl

| Time (hrs) | Glucose (g/l) | Xylose (g/l) | Ethanol (g/l) |
|---|---|---|---|
| 0 | 21.4 | 20.2 | 0.0 |
| 16.5 | 0.1 | 8.8 | 20.0 |
| 18.5 | 0.0 | 5.2 | 16.1 |
| 21 | 0.0 | 1.9 | 16.6 |
| 22.5 | 0.0 | 0.8 | 17.0 |
| 24.5 | 0.0 | 0.3 | 17.3 |
| 40 | 0.0 | 0.0 | 17.6 |

TABLE 5

HPLC data RN1001Epl

| Time (hrs) | Glucose (g/l) | Xylose (g/l) | Ethanol (g/l) |
|---|---|---|---|
| 0 | 21.4 | 20.3 | 0.0 |
| 16.5 | 0.3 | 13.4 | 17.7 |
| 18.5 | 0.0 | 9.1 | 14.4 |
| 21 | 0.0 | 4.5 | 15.8 |
| 22.5 | 0.0 | 2.0 | 16.8 |
| 24.5 | 0.0 | 0.6 | 17.5 |
| 40 | 0.0 | 0.1 | 17.9 |

Because no G418 was added to the AFM experiment, it was determined how many cells still contained their plasmid. Therefore at the end of the last AFM experiment the same amount of cell culture was plated on YEPD agar plates and YEPD agar plates containing G418. Four times as much colonies were obtained on the agarplates without G418. These results showed that approximately 25% of the cells still contained their plasmid, indicating plasmid loss in both RN1001Gpl and RN1001Epl. Therefore new transformants were constructed which contain an extra, constitutively expressed copy of the GLO1 gene, stably integrated in the genome.

Example 4

Construction of the Integrative Fragments

Figure 6:
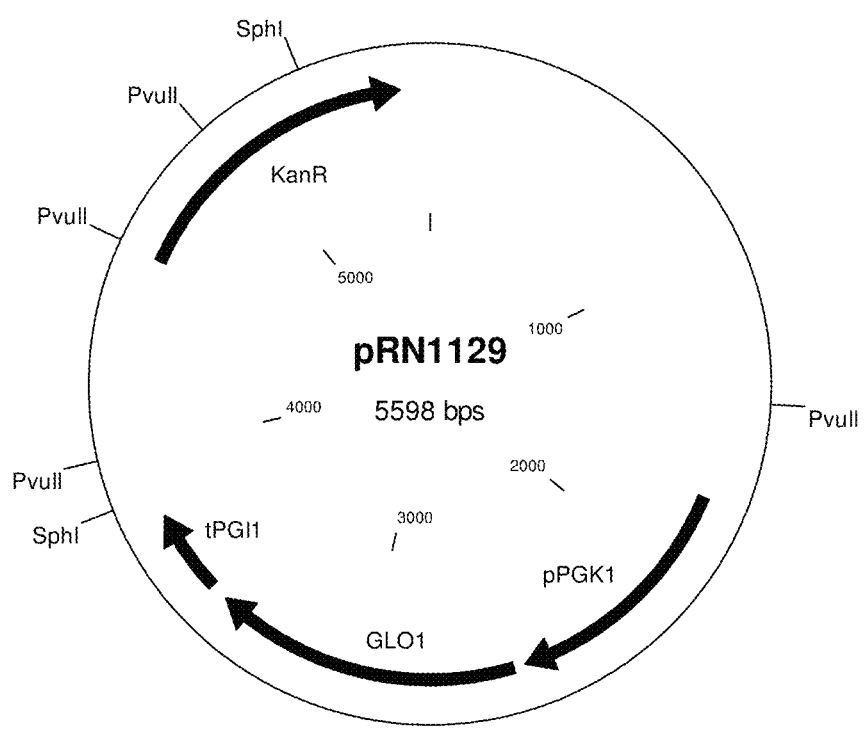
FIG. 6: Map of plasmid pRN1129 (see examples)
Figure 12:
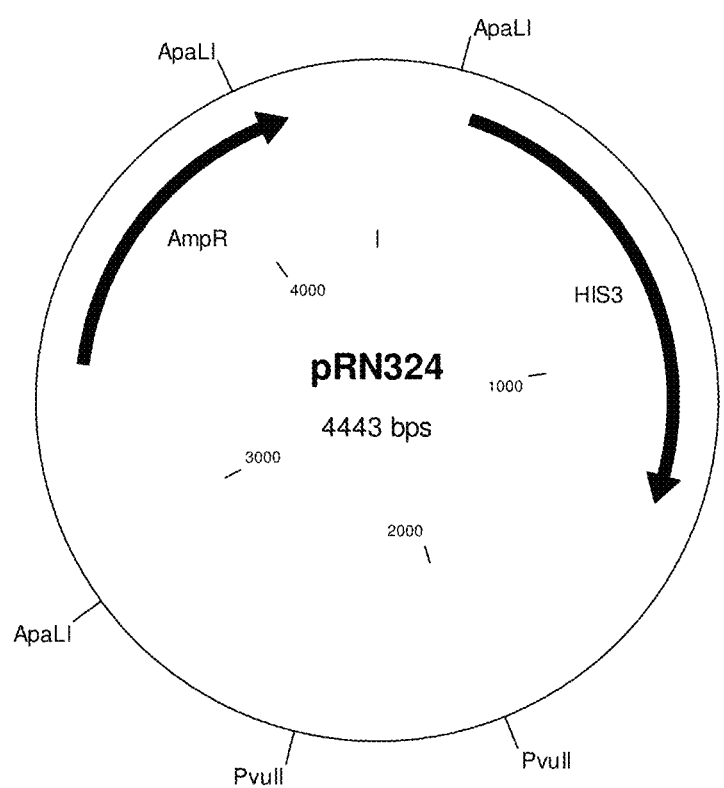
FIG. 12: Map of plasmid pRN324.
Figure 13:
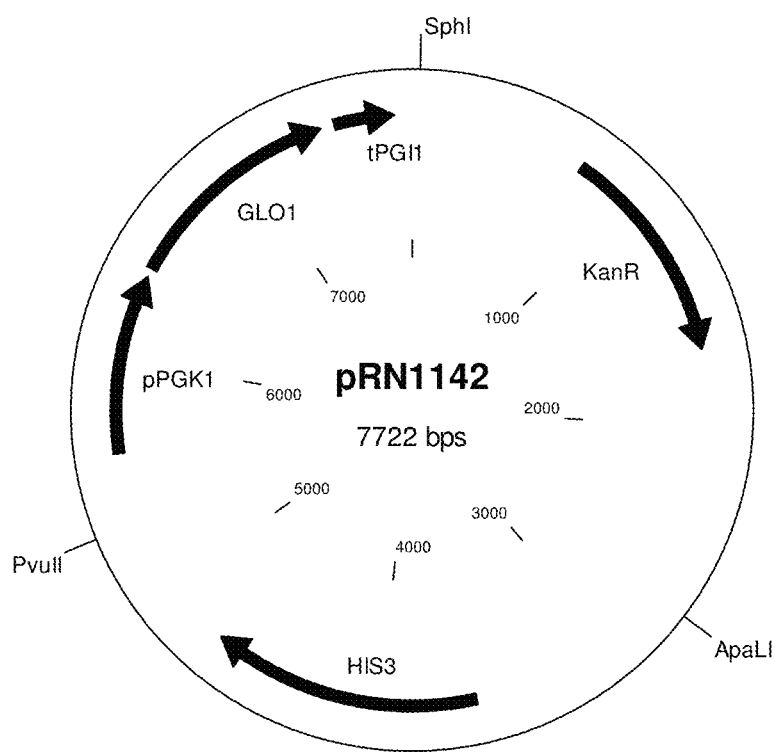
FIG. 13: Map of plasmid pRN1142.

To overcome the problem of plasmid loss during the AFM experiment, the GLO1 expression cassette was integrated into the genome of the yeast strains together with HIS3 for selection of correct transformants. To this end, a plasmid was constructed containing the GLO1 expression cassette and the HIS3 expression cassette. The GLO1 expression cassette (present in pRN1129) and the HIS3 expression cassette (present in pRN324) were extracted from the plasmid using restriction enzymes PvuII and SphI or ApaLI (FIGS. 6 and 12). Subsequently both fragments were ligated together on the PvuII site. The resulting fragment was amplified by PCR using primers SEQ ID NO 11 and SEQ ID NO 12, cloned in a TOPO blunt vector using the Zero Blunt® TOPO® PCR Cloning kit (Invitrogen, Carlsbad, Calif., USA) and transformed to One Shot® TOP10 chemically competent *E. coli* (Invitrogen, Carlsbad, Calif., USA). Miniprep DNA isolations were performed on several colonies. The obtained plasmids were checked by restriction enzyme analyses. The correct plasmid was called pRN1142 (FIG. 13).

Figure 14:
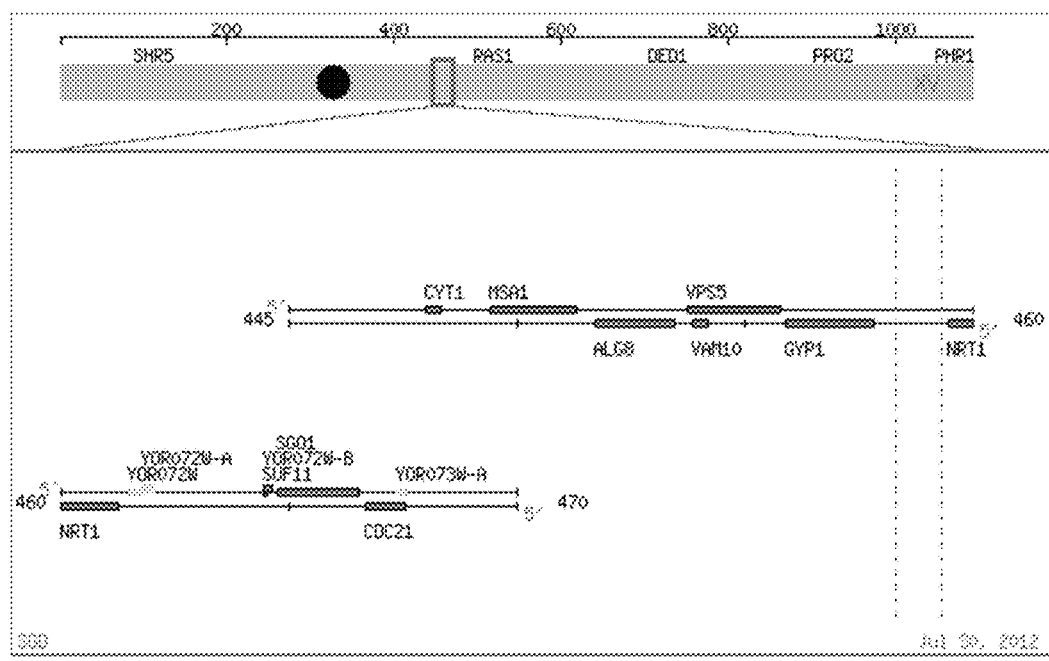
FIG. 14: Map showing integration site in *S. cervisiae* genome: Integration site 1 (Chr XV, coordinates 458319 bp to 459320 bp). The specified map is indicated by the region between the two vertical dashed lines.

Subsequently the GLO1 and HIS3 fragment was PCR amplified using primers SEQ ID NO 11 and SEQ ID NO 12 and pRN1142 as template. To create a control strain, the HIS3 expression cassette was PCR amplified with primers SEQ ID NO 11 and SEQ ID NO 13 and pRN324 as template. For integration in the genome, two 500 bp flanks needed to be obtained of integration site 1 (INT1), a map of the integration site is given in FIG. 14 (obtained from http://www.yeastgenome.org/). A 5' and 3' 500 bp flank, for integration to INT1, were PCR amplified using primers SEQ ID NO 14 and SEQ ID NO 15 for the 5' flank and primers SEQ ID NO 16 and SEQ ID NO 17 for the 3' flank. As a template genomic DNA from RN1001 was used. All PCR reactions were purified over column by using the GeneJET™ Gel Extraction kit (Fermentas, 68789 St. Leon-Rot/Germany). The nucleotide sequence of the 5' flank is included as SEQ ID NO 18 and the 3' flank as SEQ ID NO 19.

Plasmid pRN324 contains the following relevant elements: the HIS3 expression cassette flanked by restriction sites ApaLI and PvuII, and an ampicillin resistance marker.

Plasmid pRN1129 contains the following relevant elements: the GLO1 expression cassette (consisting of the PGK1 promoter, the GLO1 ORF and the PGI1 terminator) flanked by restriction sites PvuII and SphI, and a kanamycin resistance marker.

Primer SEQ ID NO 11 is the forward primer of the HIS3 cassette, consisting of 25 nucleotides and a tail of 50 nucleotides on the 5'-end, identical to the 50 nucleotides of the 3'-end of the 5' 500 bp INT1 flank.

Primer SEQ ID NO 12 is the reverse primer of the GLO1 cassette, consisting of 25 nucleotides and a tail of 50 nucleotides on the 5'-end, identical to the 50 nucleotides of the 5'-end of the 3' 500 bp INT1 flank.

Primer SEQ ID NO 13 is the reverse primer of the HIS3 cassette, consisting of 25 nucleotides and a tail of 50 nucleotides on the 5'-end, identical to the 50 nucleotides of the 5'-end of the 3' 500 bp INT1 flank.

Primer SEQ ID NO 14 is the forward primer of the 5' 500 bp INT1 flank.

Primer SEQ ID NO 15 is the reverse primer of the 5' 500 bp INT1 flank.

Primer SEQ ID NO 16 is the forward primer of the 3' 500 bp INT1 flank.

Primer SEQ ID NO 17 is the reverse primer of the 3' 500 bp INT1 flank.

All primer sequences mentioned above are also indicated in FIG. 15.

Example 5

Transformation of Yeast Strains with Integrative Fragments

Figure 15:
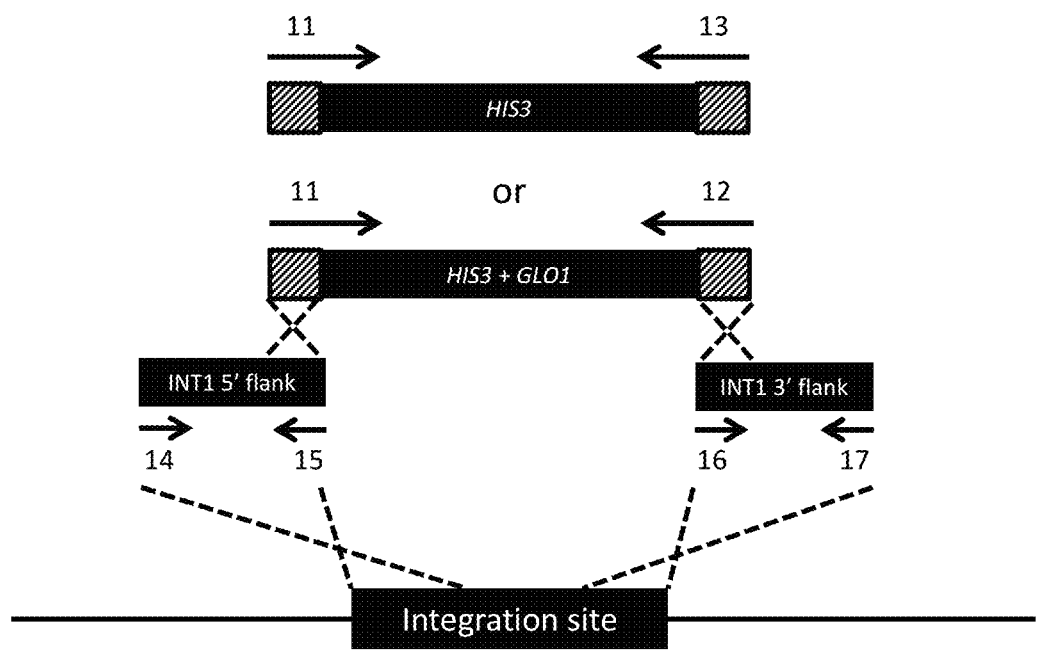
FIG. 15: Scheme that shows mechanism of integration of the PCR fragments (His or His-Glo) into the *S. cervisiae* genome.

The mechanism of integration of the PCR fragments into the genome is schematically shown in FIG. 15. The obtained PCR fragments (Example 4) were used to transform the strains RN1041 and RN1216, both containing an auxotrophy for histidine. Correct transformants were selected on YNB plates containing 2% glucose. Transformants were checked with colony PCR, using primers SEQ ID NO 14 and SEQ ID NO 17, for integration of the expression cassettes into the genome. The RN1041 strain containing the HIS3 and GLO1 expression cassettes is named RN1041HG, and the RN1041 control strain containing the HIS3 expression cassette is named RN1041H. The RN1216 strain containing the HIS3 and GLO1 expression cassettes is named RN1216HG, and the RN1216 control strain containing the HIS3 expression cassette is named RN1216H.

From both control strains, RN1041H and RN1216H, one colony each was selected for Q-PCR. From RN1041HG and RN1216HG, two individual colonies each were selected for Q-PCR (clone 1 and clone 2).

Figure 16:
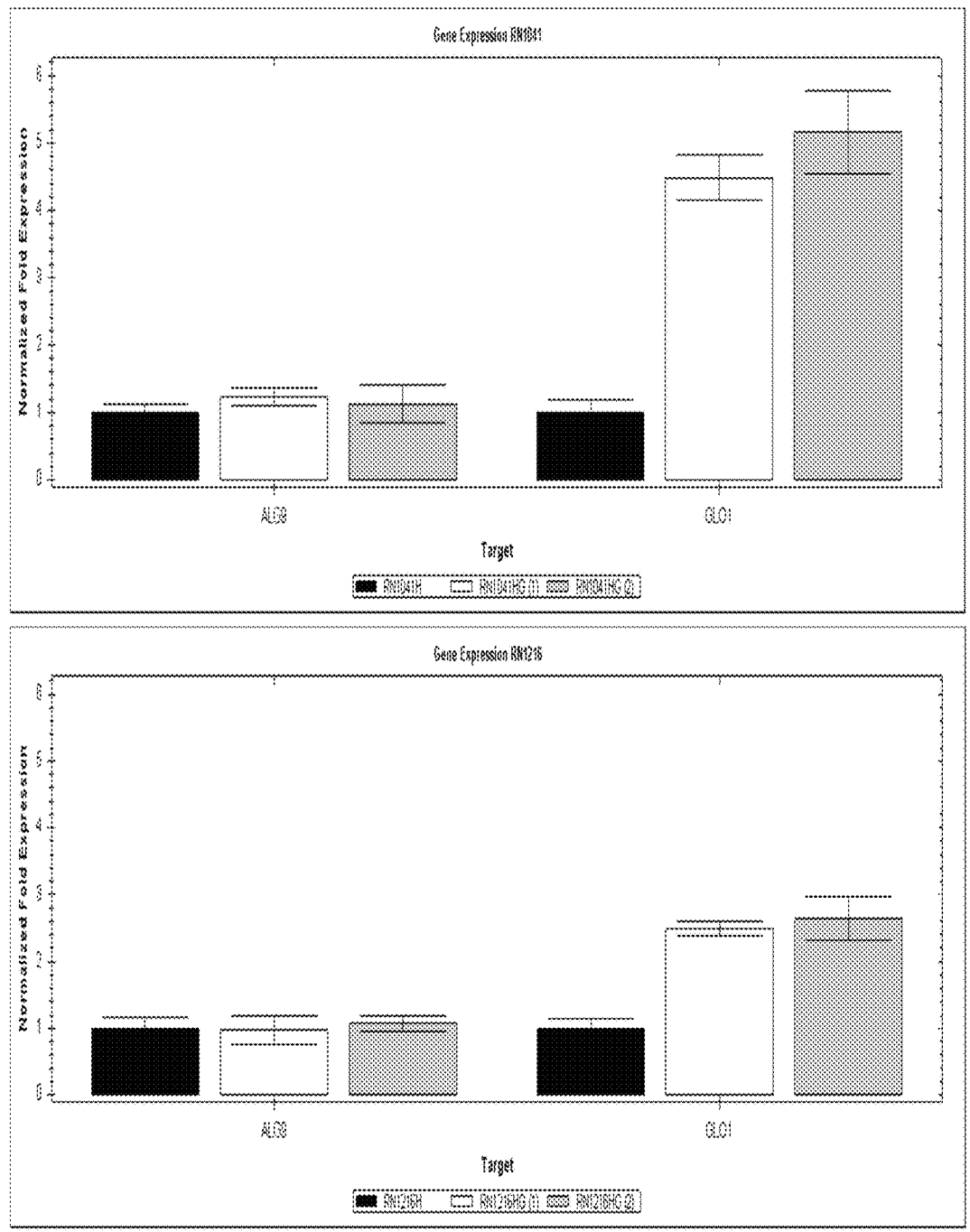
FIG. 16: Gene expression data. Normalized Fold Expression for GLO1 of strains RN1041 (top) and RN1216 (bottom)

The expression of the GLO1-gene in the transformants was checked in a Q-PCR experiment. For the Q-PCR experiment all selected strains were grown overnight in YEP medium containing 2% glucose. Subsequently RNA was isolated from the cultures and was checked for genomic DNA contamination by PCR using primers SEQ ID NO 3 and SEQ ID NO 4. No contamination was found. Then a cDNA synthesis was performed on the RNA using the RevertAid kit (Fermentas, 68789 St. Leon-Rot/Germany). Next a Q-PCR experiment was done with primers SEQ ID NO 5 and SEQ ID NO 6. Two housekeeping genes were used as a reference, ALG9 using primers SEQ ID NO 7 and SEQ ID NO 8 and UBC6 using primers SEQ ID NO 9 and SEQ ID NO 10. The GLO1 expression data was normalized on the housekeeping gene with the best duplo CT-values, in this case UBC6. All 4 strains containing HIS3 and GLO1 showed a higher normalized expression of GLO1 as compared to their control strain (FIG. 16), about 4-5 times higher in the RN1041 background compared to ALG9 and about 2-3 times higher in the RN1216 background.

Example 6

AFM Experiments

After verification of higher GLO1 expression in all 4 strains containing HIS3 and GLO1 compared to their control strain by Q-PCR (Example 5), an AFM experiment was started to determine the conversion rate of the presented sugars into ethanol by measuring the $CO_2$ production during the experiment, since ethanol and $CO_2$ are being produced in equimolar amounts. During the experiment, HPLC samples of the cultures were taken at different time points, in order to determine the sugar consumption rate and the ethanol production rate. The same 6 strains were tested in this AFM experiment as were used in the Q-PCR experiment for determination of GLO1 expression.

Precultures were made of all 3 RN1041 derived strains (RN1041H, RN1041 HG-1 and RN1041 HG-2), by inoculating some cell material from plate in 100 ml YEP containing 2% glucose. The next day 400 ml Mineral Medium containing 2% glucose and 2% xylose was inoculated with cell material from the precultures.

Figure 17:
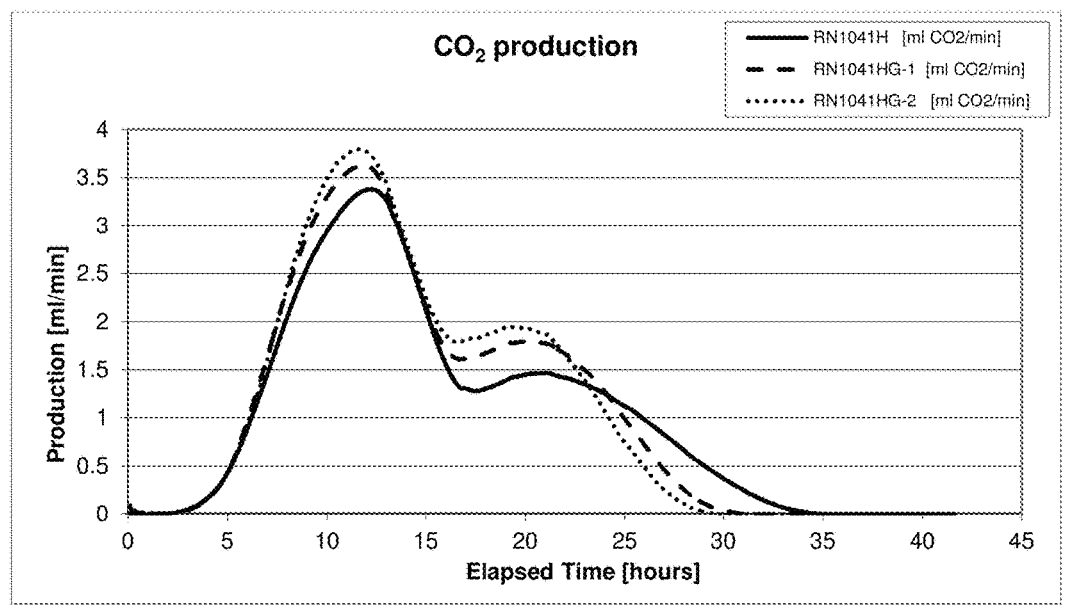
FIG. 17: $CO_2$ production curve for growth of strains RN1041H, RN1041HG-1 and RN1041HG-2.
Figure 18:
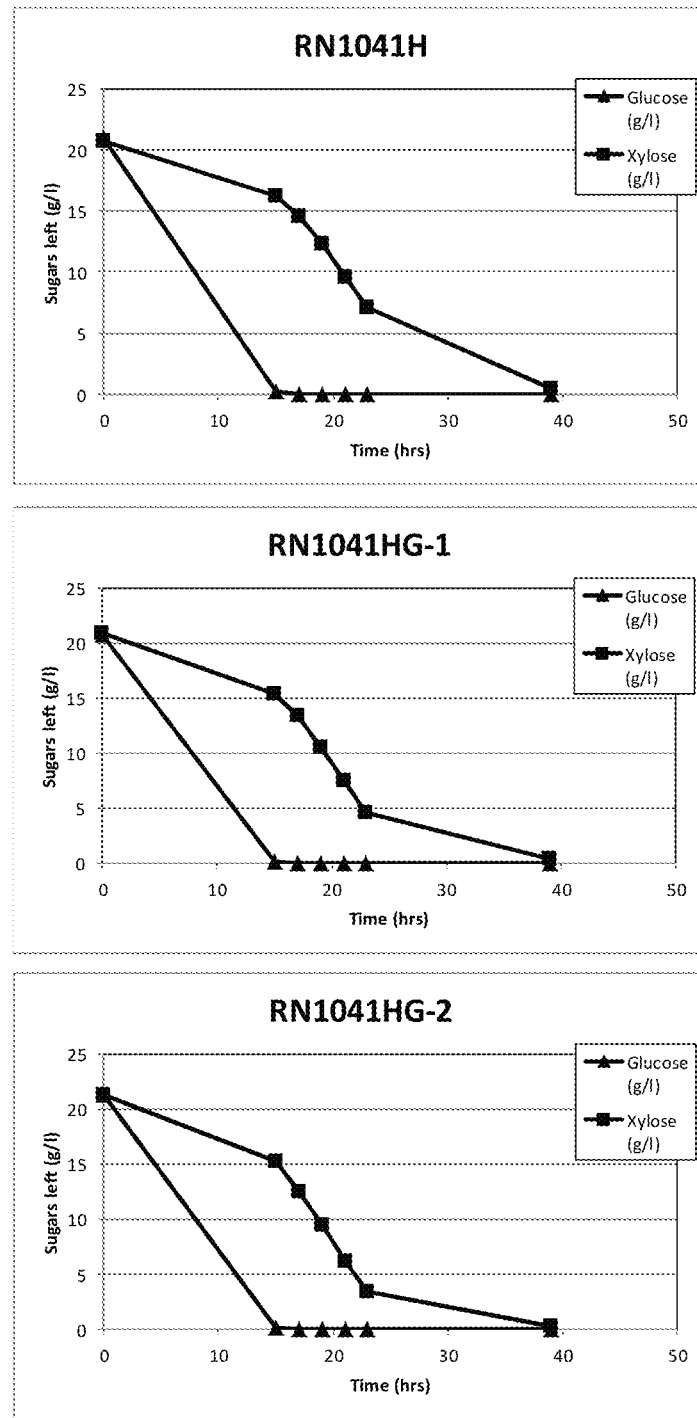
FIG. 18: Sugar consumption curve of strains RN1041H (top), RN1041HG-1 (mid) and RN1041 HG-2 (bottom)

The $CO_2$ production curves of the RN1041 derived strains (FIG. 17) showed faster and higher $CO_2$ production rates in RN1041HG (clone 1 and 2) as compared to RN1041H, indicating a faster glucose and xylose consumption in RN1041HG (clone 1 and 2) as compared to the control strain RN1041H. The HPLC data (Tables 6, 7 and 8, and FIG. 18) indeed confirm faster xylose consumption in the RN1041 HG (clone 1 and 2) strains as compared to the RN1041H strain, the glucose was already consumed at the second timepoint (15 hours).

TABLE 6

HPLC data RN1041H

| Time (hrs) | Glucose (g/l) | Xylose (g/l) | Ethanol (g/l) |
|---|---|---|---|
| 0 | 20.9 | 20.7 | 0.0 |
| 15 | 0.3 | 16.1 | 14.2 |
| 17 | 0.0 | 14.5 | 12.5 |
| 19 | 0.0 | 12.3 | 12.6 |
| 21 | 0.0 | 9.6 | 13.4 |
| 23 | 0.0 | 7.1 | 14.5 |
| 39 | 0.0 | 0.5 | 17.5 |

TABLE 7

HPLC data RN1041HG-1

| Time (hrs) | Glucose (g/l) | Xylose (g/l) | Ethanol (g/l) |
|---|---|---|---|
| 0 | 20.8 | 20.8 | 0.0 |
| 15 | 0.1 | 15.4 | 14.0 |
| 17 | 0.0 | 13.4 | 12.9 |
| 19 | 0.0 | 10.6 | 13.1 |
| 21 | 0.0 | 7.5 | 14.2 |
| 23 | 0.0 | 4.6 | 15.6 |
| 39 | 0.0 | 0.4 | 17.6 |

TABLE 8

HPLC data RN1041HG-2

| Time (hrs) | Glucose (g/l) | Xylose (g/l) | Ethanol (g/l) |
|---|---|---|---|
| 0 | 21.3 | 21.3 | 0.0 |
| 15 | 0.1 | 15.3 | 13.3 |
| 17 | 0.0 | 12.5 | 13.6 |
| 19 | 0.0 | 9.4 | 14.2 |
| 21 | 0.0 | 6.2 | 15.6 |
| 23 | 0.0 | 3.3 | 16.6 |
| 39 | 0.0 | 0.2 | 18.2 |

These results clearly showed that overexpression of the GLO1-gene leads to a faster and more efficient fermentation of biomass sugars, leading to a reduced fermentation time. This means that the sugars are more efficiently being converted into ethanol.

A new AFM experiment was started with the RN1216 derived strains. Precultures were made of all 3 strains (RN1216H, RN1216HG-1 and RN1216HG-2), by inoculating some cell material from agar plate in 100 ml YEP containing 2% glucose. The next day 400 ml Mineral Medium containing 5% glucose and 5% xylose was inoculated with cell material from the precultures.

Figure 19:
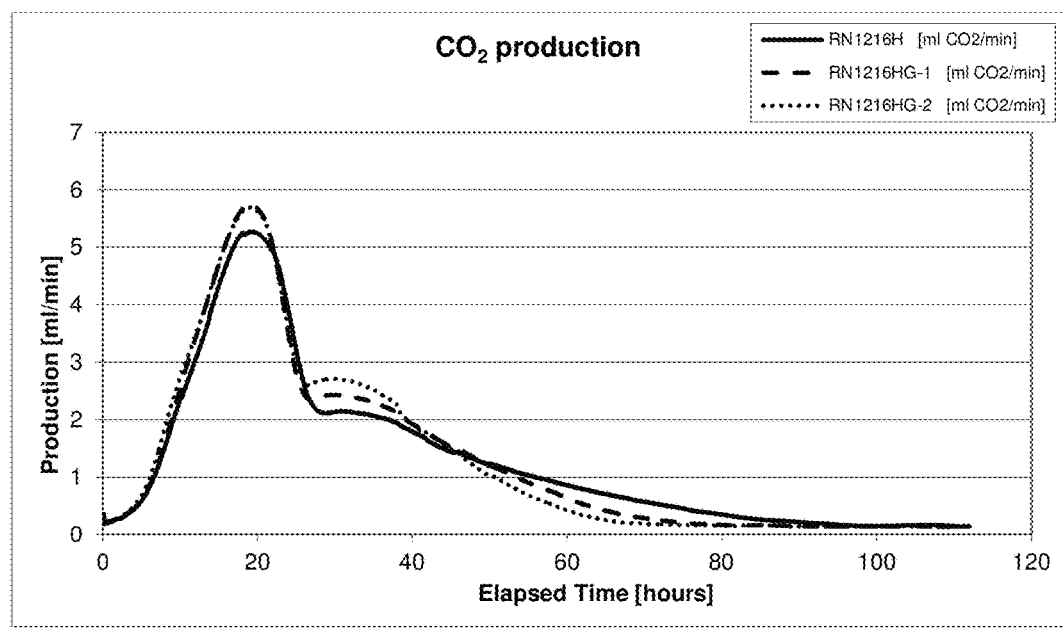
FIG. 19: $CO_2$ production curve for growth of strains RN1216H, RN1216HG-1 and RN1216HG-2.
Figure 20:
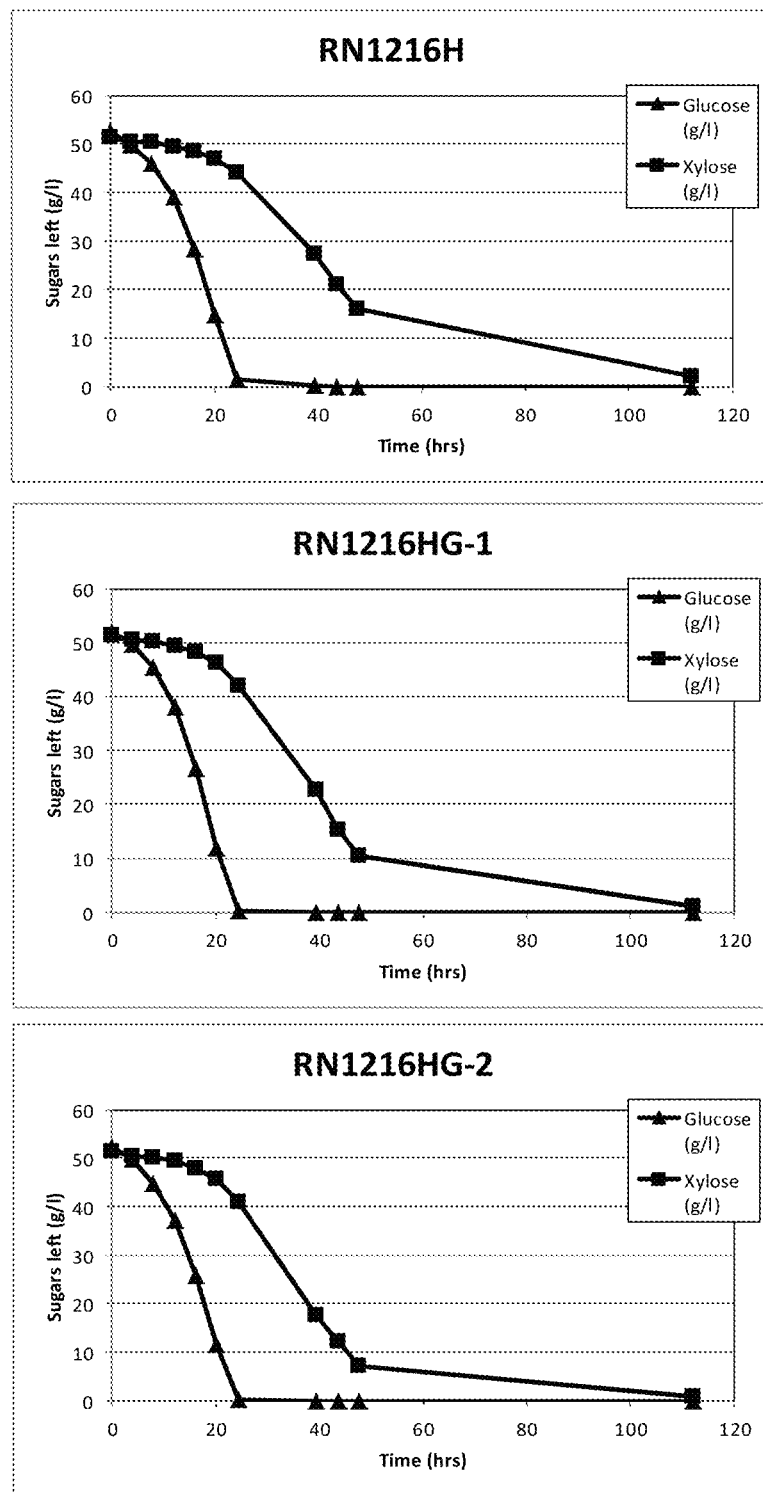
FIG. 20: Sugar consumption curve of strains RN1216H (top), RN1216HG-1 (mid) and RN1216HG-2 (bottom) showing sugar consumption.

The $CO_2$ production curves of RN1216 (FIG. 19) showed faster and higher $CO_2$ production rates in RN1216HG (clone 1 and 2) as compared to RN1216H, indicating a faster, more efficient glucose and xylose consumption in RN1216HG (clone 1 and 2) as compared to the control strain RN1216H. HPLC data (Tables 9, 10 and 11, and FIG. 20) confirmed a faster glucose and xylose consumption in the RN1216HG (clone 1 and 2) strains as compared to the RN1216H strain.

TABLE 9

HPLC data RN1216H

| Time (hrs) | Glucose (g/l) | Xylose (g/l) | Ethanol (g/l) |
|---|---|---|---|
| 0 | 52.5 | 51.4 | 0.0 |
| 4 | 49.8 | 50.5 | 0.7 |
| 8 | 45.9 | 50.3 | 2.2 |
| 12 | 39.1 | 49.6 | 5.1 |
| 16 | 28.5 | 48.6 | 10.0 |
| 20 | 14.7 | 47.0 | 16.8 |
| 24.5 | 1.4 | 44.2 | 28.5 |
| 39.5 | 0.2 | 27.5 | 35.1 |
| 43.5 | 0.0 | 21.0 | 36.5 |
| 47.5 | 0.0 | 16.1 | 38.5 |
| 112 | 0.0 | 2.1 | 45.4 |

TABLE 10

HPLC data RN1216HG-1

| Time (hrs) | Glucose (g/l) | Xylose (g/l) | Ethanol (g/l) |
|---|---|---|---|
| 0 | 52.1 | 51.3 | 0.0 |
| 4 | 49.6 | 50.4 | 0.7 |
| 8 | 45.5 | 50.1 | 2.3 |
| 12 | 38.1 | 49.4 | 5.5 |
| 16 | 26.8 | 48.3 | 10.8 |
| 20 | 12.0 | 46.2 | 18.1 |
| 24.5 | 0.2 | 42.1 | 28.9 |
| 39.5 | 0.0 | 22.7 | 36.5 |
| 43.5 | 0.0 | 15.2 | 38.8 |
| 47.5 | 0.0 | 10.4 | 40.7 |
| 112 | 0.0 | 1.1 | 45.5 |

TABLE 11

HPLC data RN1216HG-2

| Time (hrs) | Glucose (g/l) | Xylose (g/l) | Ethanol (g/l) |
|---|---|---|---|
| 0 | 52.2 | 51.2 | 0.0 |
| 4 | 49.6 | 50.4 | 0.8 |
| 8 | 44.9 | 50.0 | 2.6 |
| 12 | 37.2 | 49.3 | 6.0 |
| 16 | 25.9 | 47.9 | 11.3 |
| 20 | 11.5 | 45.8 | 18.6 |
| 24.5 | 0.2 | 41.0 | 29.1 |
| 39.5 | 0.0 | 17.5 | 38.5 |
| 43.5 | 0.0 | 12.4 | 40.2 |
| 47.5 | 0.0 | 7.3 | 42.4 |
| 112 | 0.0 | 0.8 | 45.7 |

These results reconfirmed the results above: overexpression of the GLO1-gene leads to a faster and more efficient fermentation of biomass sugars, in this case xylose and glucose, leading to a reduced overall fermentation time and more efficient conversion of the aforementioned sugars into ethanol.

Example 7

GLO1 Variants

GLO1 homologues, from other organisms than *S. cerevisiae*, are expressed in the same fashion as described in the previous examples. To this end, gene sequences were synthesized on basis of the protein sequences, listed as SED ID NO: 20 to SEQ ID NO: 24. The sequence of the open reading frame was generated by the method described in WO/2008/000632. The protein sequences are derived from *Saccharomyces cerevisiae, Candida glabrata, Zygosaccharomyces rouxii, Kluyveromyces lactis* and *Candida magnoliae*. As a reference, the wild-type GLO1 gene from *S. cerevisiae* (see previous examples) is used.

The constructs thus obtained are used to transform strain RN1216, as described in the previous examples.

All transformants show enhanced sugar consumption rates when tested in an AFM experiment (see also example 10), both on basis of carbon dioxide profiles and actual sugar concentrations during the experiment.

In an embodiment the following signatures that are present in some active GLO1 versions, especially in terms of enhancing co-fermentation of mixed sugar substrates, are as follows:

TABLE 12

GLO1 signature patterns

| Sequence | Position in *S. cerevisiae* (SEQ ID No 20) |
|---|---|
| (E,s,d)-L-X-(H,Y)-(N,s) | E242-L243-X-H245-N246 |
| G-(F,Y)-G-H | G266-Y267-G268-H269 |
| G-X(6)-(F,i)-X(2,3)-D-X(3)-Y | G301-X(6)-F308-X(2)-D311 -X(3)-Y315 |

In table 12, X designates an amino acid (i.e. any amino acid).

If two amino acid residues are mentioned between brackets, either one applies (e.g. (F,Y)).

Small letters designate minor variants, e.g. (F,i) means that in most cases, amino acid F is observed, but in a few cases amino acid I (isoleucine).

Example 8

Construction of the Integrative Fragments

Figure 21:
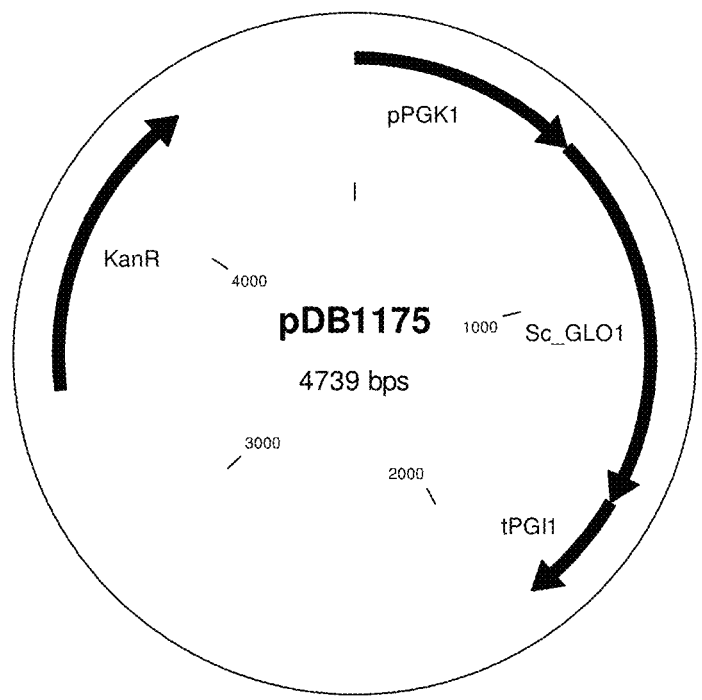
FIG. 21: Map of plasmid pDB1175 (see examples)
Figure 22:
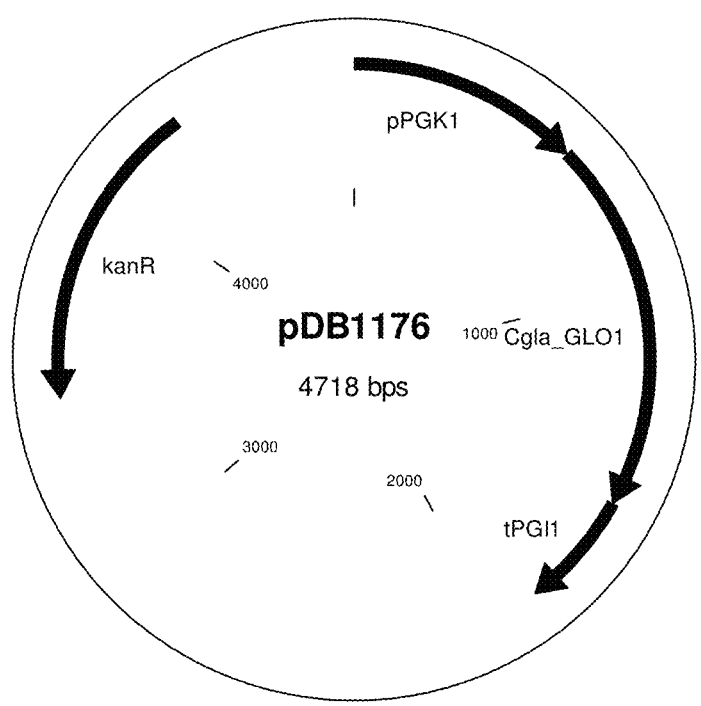
FIG. 22: Map of plasmid pDB1176 (see examples)
Figure 23:
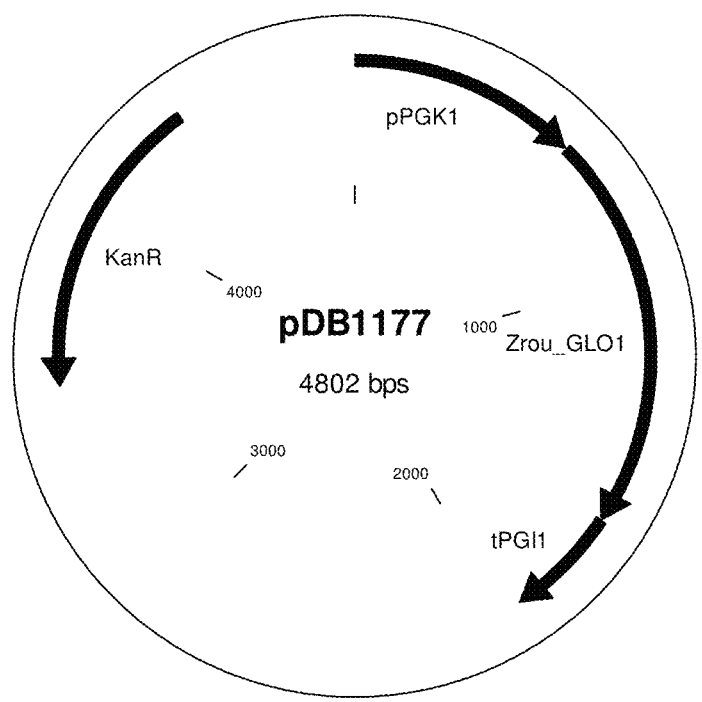
FIG. 23: Map of plasmid pDB1177 (see examples)
Figure 24:
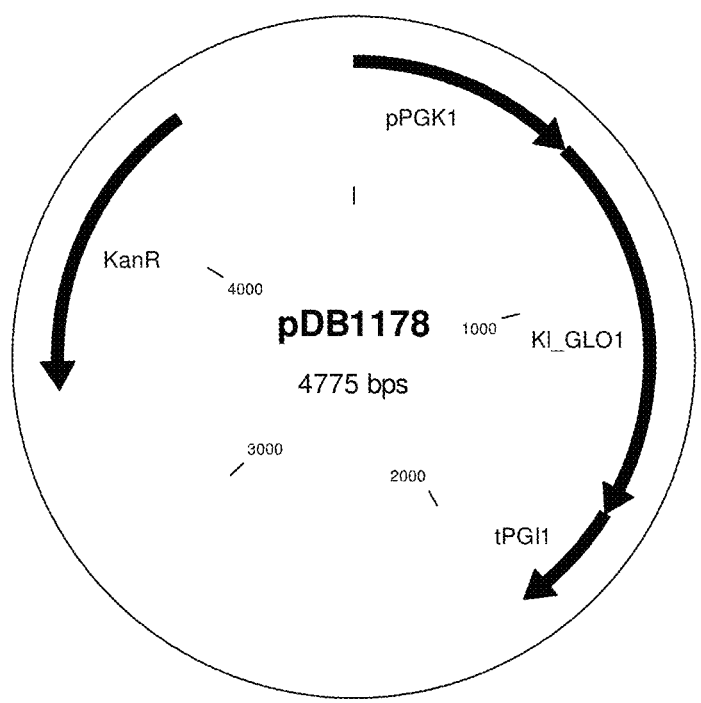
FIG. 24: Map of plasmid pDB1178 (see examples)
Figure 25:
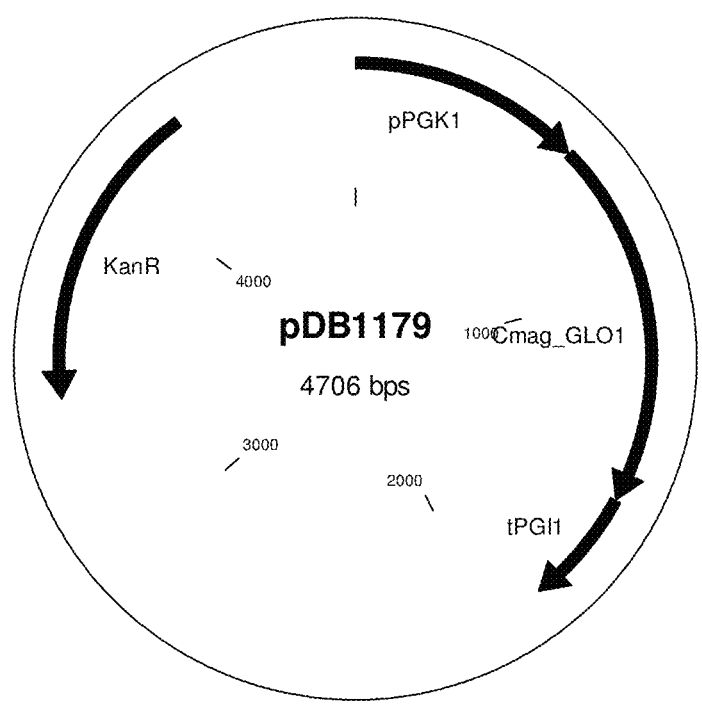
FIG. 25: Map of plasmid pRN1179 (see examples)

The GLO1 homologues were integrated into the genome of the yeast strain RN1216 together with H/S3 for selection of correct transformants. To this end, plasmids were constructed, each containing a different GLO1 homologue together with the PGK1 promoter and PGI1 terminator. The plasmids were constructed according to the method described in PCT/EP2013/056623. The plasmids were called pDB1175 (FIG. 21), pDB1176 (FIG. 22), pDB1177 (FIG. 23), pDB1178 (FIG. 24) and pDB1179 (FIG. 25).

Subsequently the different GLO1 expression cassettes were PCR amplified using primers SEQ ID NO 28 and SEQ ID NO 29 and pDB1175, pDB1176, pDB1177, pDB1178 and pDB1179 as template. The H/S3 expression cassette was PCR amplified using SEQ ID NO 30 and SEQ ID NO 31 and pRN324 (FIG. 12) as template. For integration in the genome, two 500 bp flanks needed to be obtained of integration site 1 (INT1) (described in example 4). A 5' and 3' 500 bp flank, for integration to INT1, were PCR amplified using primers SEQ ID NO 14 and SEQ ID NO 32 for the 5' flank and primers SEQ ID NO 33 and SEQ ID NO 17 for the 3' flank. As a template genomic DNA from RN1001 was used. All PCR reactions were purified over column by using the GeneJET™ Gel Extraction kit (Fermentas, 68789 St. Leon-Rot/Germany).

Plasmid pDB1175 contains the following relevant elements: the Sc_GLO1 expression cassette (consisting of the PGK1 promoter, the codon pair optimized GLO1 ORF from *Saccharomyces cerevisiae* and the PGI1 terminator), and a kanamycin resistance marker.

Plasmid pDB1176 contains the following relevant elements: the Cgla_GLO1 expression cassette (consisting of the PGK1 promoter, the codon pair optimized GLO1 ORF from *Candida glabrata* and the PGI1 terminator), and a kanamycin resistance marker.

Plasmid pDB1177 contains the following relevant elements: the Zrou_GLO1 expression cassette (consisting of the PGK1 promoter, the codon pair optimized GLO1 ORF from *Zygosaccharomyces rouxii* and the PGI1 terminator), and a kanamycin resistance marker.

Plasmid pDB1178 contains the following relevant elements: the Kl_GLO1 expression cassette (consisting of the PGK1 promoter, the codon pair optimized GLO1 ORF from *Kluyveromyces lactis* and the PGI1 terminator), and a kanamycin resistance marker.

Plasmid pDB1179 contains the following relevant elements: the Cmag_GLO1 expression cassette (consisting of the PGK1 promoter, the codon pair optimized GLO1 ORF from *Candida magnoliae* and the PGI1 terminator), and a kanamycin resistance marker.

Plasmid pRN324: described in example 4

Primer SEQ ID NO 28 is the forward primer of the homologous GLO1 expression cassettes (including promoter and terminator).

Primer SEQ ID NO 29 is the reverse primer of the homologous GLO1 expression cassettes (including promoter and terminator).

Primer SEQ ID NO 30 is the forward primer of the HIS3 cassette, consisting of 20 nucleotides and a tail of 50 nucleotides on the 5'-end, identical to the 50 nucleotides of the 3'-end of the homologous GLO1 expression cassettes.

Primer SEQ ID NO 31 is the reverse primer of the HIS3 cassette, consisting of 21 nucleotides and a tail of 50 nucleotides on the 5'-end, identical to the 50 nucleotides of the 5'-end of the 3' 500 bp INT1 flank.

Primer SEQ ID NO 32 is the reverse primer of the 5' 500 bp INT1 flank, consisting of 23 nucleotides and a tail of 50 nucleotides on the 5'-end, identical to the 50 nucleotides of the 5'-end of the homologous GLO1 expression cassettes.

Primer SEQ ID NO 33 is the forward primer of the 3' 500 bp INT1 flank, consisting of 24 nucleotides and a tail of 50 nucleotides on the 5'-end, identical to the 50 nucleotides of the 3'-end of the HIS3 expression cassette.

All primer sequences mentioned above are also indicated in FIG. 26.

Example 9

Transformation of Yeast Strain with Integrative Fragments

Figure 26:
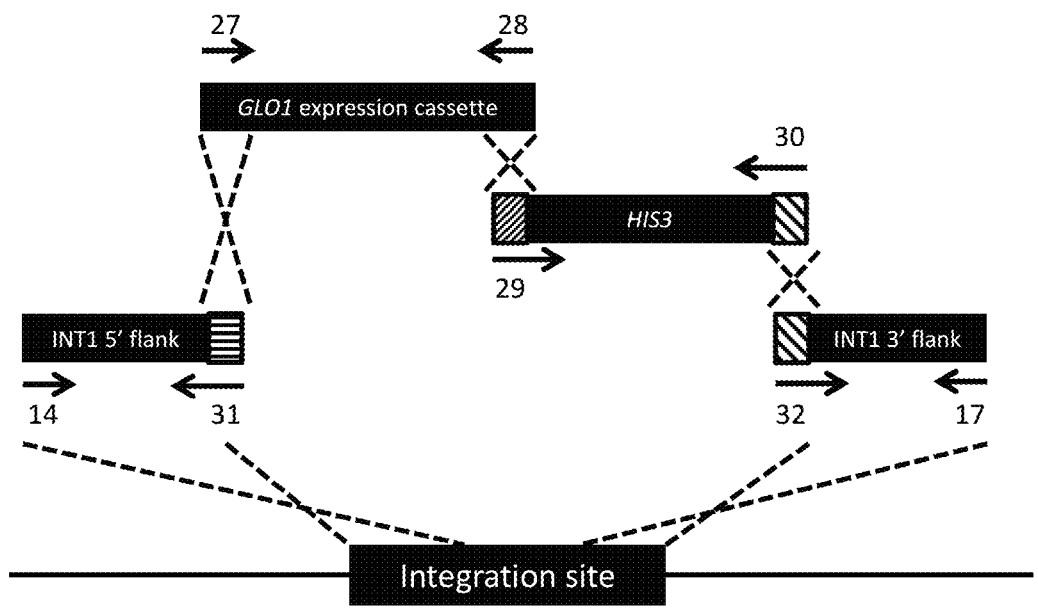
FIG. 26: Scheme that shows mechanism of integration of the PCR fragments into the *S. cervisiae* genome.

The mechanism of integration of the PCR fragments into the genome is schematically shown in FIG. 26. The obtained PCR fragments (Example 8) were used to transform strain RN1216, which contains an auxotrophy for histidine. Correct transformants were selected on YNB plates containing 2% glucose. Transformants were checked with colony PCR, using primers SEQ ID NO 14 and SEQ ID NO 17, for integration of the expression cassettes into the genome. Correct strains were named the following: RN1216 ScG_H, RN1216 CglaG_H, RN1216 ZrouG_H, RN1216 KIG_H and RN1216 CmagG_H.

Strain RN1216 ScG_H contains the Sc_GLO1 expression cassette and the HIS3 expression cassette.
Strain RN1216 CglaG_H contains the Cgla_GLO1 expression cassette and the HIS3 expression cassette.
Strain RN1216 ZrouG_H contains the Zrou_GLO1 expression cassette and the HIS3 expression cassette.
Strain RN1216 KIG_H contains the KI_GLO1 expression cassette and the HIS3 expression cassette.
Strain RN1216 CmagG_H contains the Cmag_GLO1 expression cassette and the HIS3 expression cassette.

Example 10

AFM Experiment

An AFM experiment was started to determine the conversion rate of the presented sugars into ethanol by measuring the $CO_2$ production during the experiment, since ethanol and $CO_2$ are being produced in equimolar amounts. During the experiment, HPLC samples of the cultures were taken at different time points, in order to determine the sugar consumption rate and the ethanol production rate. The strains tested in this AFM experiment are the 5 constructed strains described in example 9, and as control strain the RN1216H strain was used which is described in example 5.

Precultures were made of all 6 strains, by inoculating some cell material from plate in 100 ml YEP containing 2% glucose. The next day 400 ml Mineral Medium containing 5% glucose and 5% xylose was inoculated with cell material from the precultures.

Figure 27:
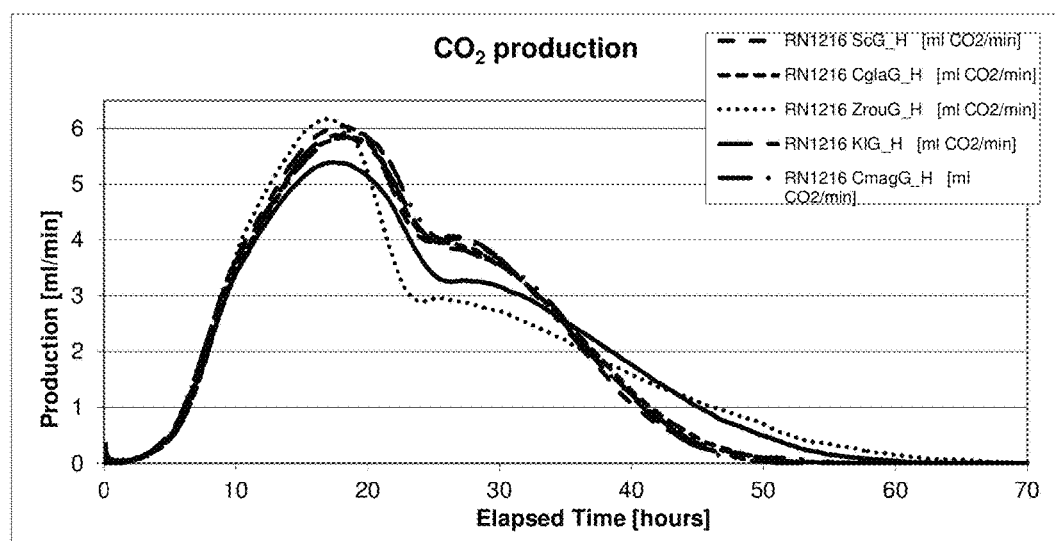
FIG. 27: $CO_2$ production curve for growth of strains RN1216 ScG_H, RN1216 CglaG_H, RN1216 ZrouG_H, RN1216 KIG_H, RN1216 CmagG_H and RN1216 H.
Figure 28:
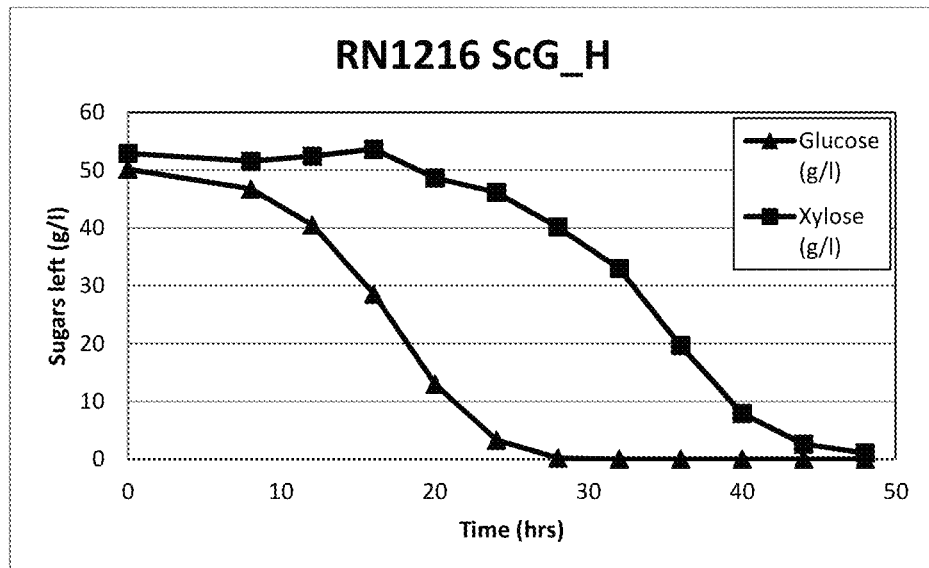
FIG. 28: Sugar consumption curve of strain RN1216 ScG_H
Figure 29:
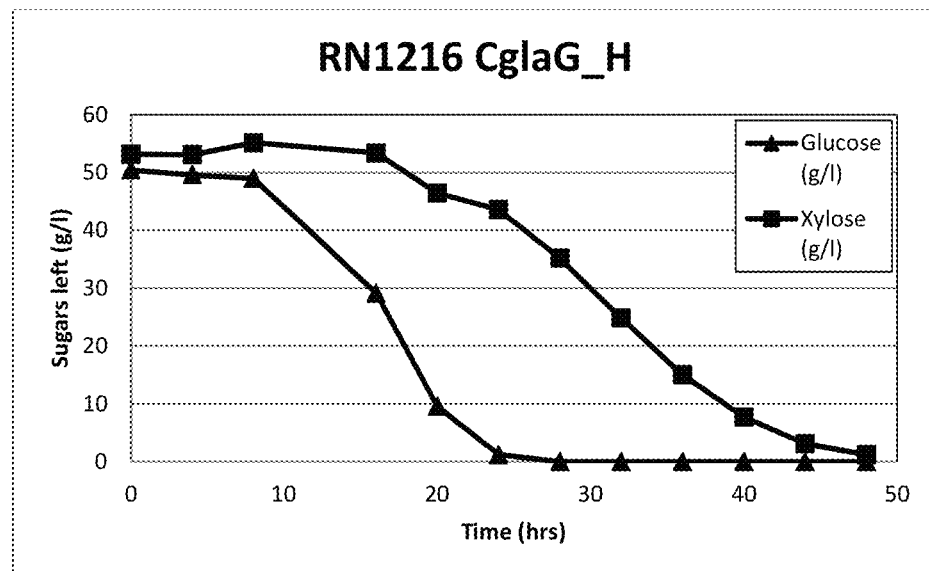
FIG. 29: Sugar consumption curve of strain RN1216 CglaG_H
Figure 30:
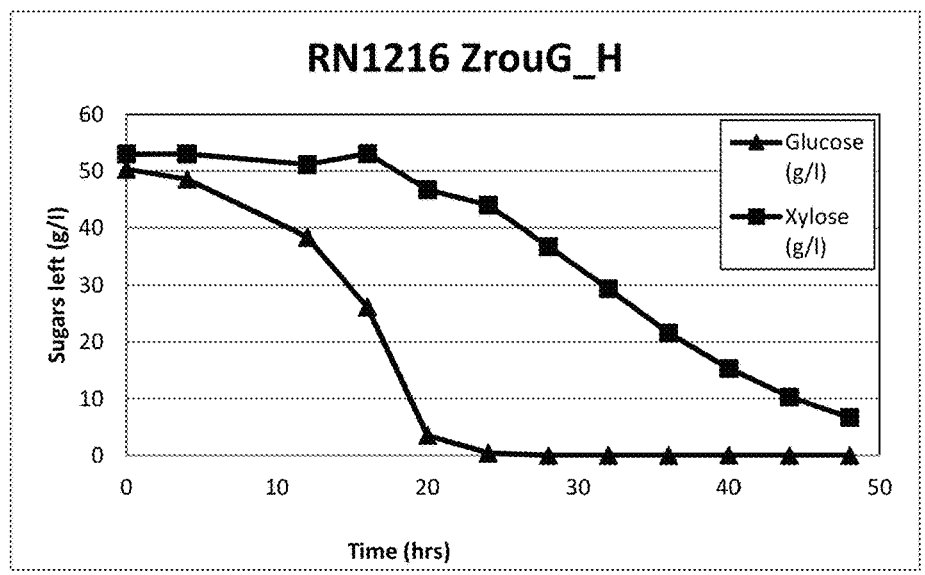
FIG. 30: Sugar consumption curve of strain RN1216 ZrouG_H
Figure 31:
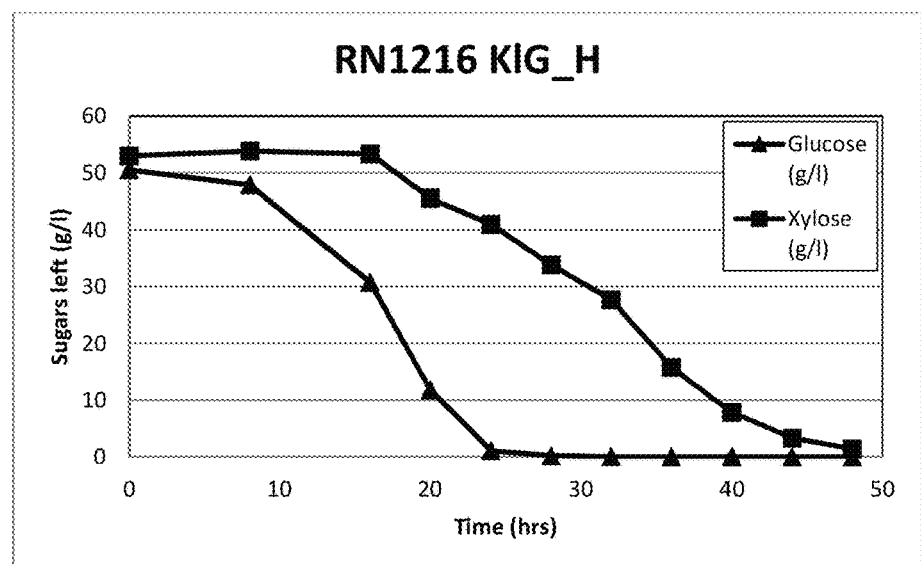
FIG. 31: Sugar consumption curve of strain RN1216 KlG_H
Figure 32:
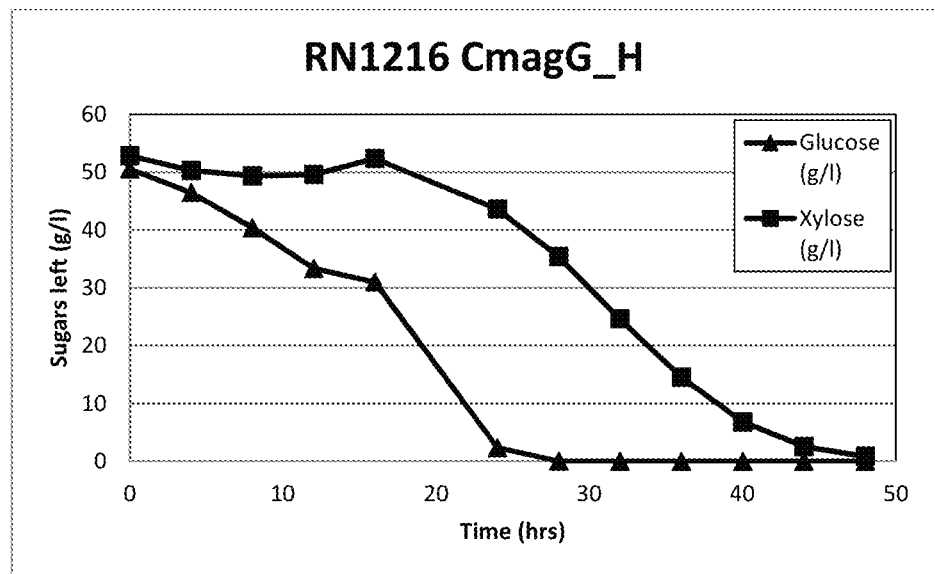
FIG. 32: Sugar consumption curve of strain RN1216 CmagG_H
Figure 33:
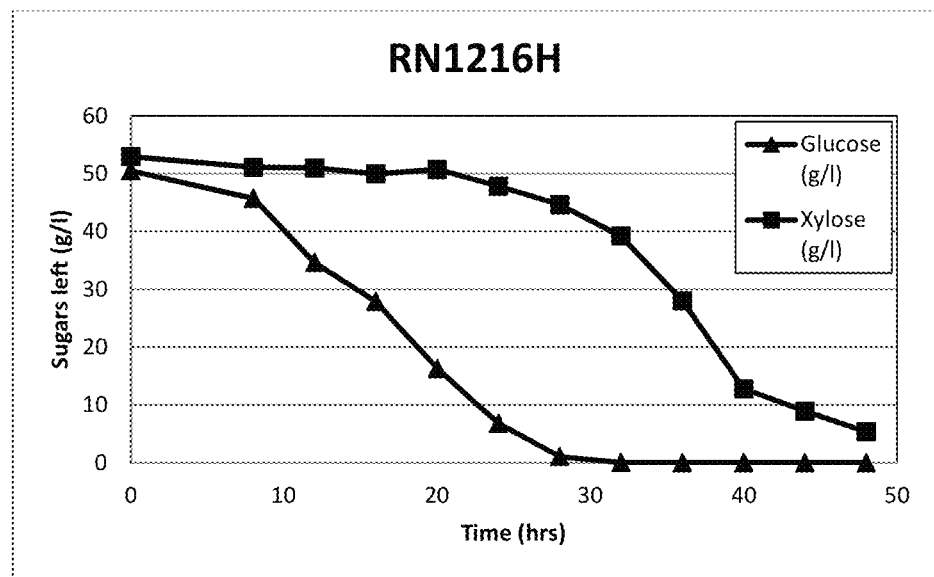
FIG. 33: Sugar consumption curve of strain RN1216 H

The $CO_2$ production curves of the RN1216 derived strains (FIG. 27) showed faster and higher $CO_2$ production rates in RN1216 ScG_H, RN1216 CglaG_H, RN1216 KIG_H and RN1216 CmagG_H as compared to RN1216H, indicating a faster glucose en xylose consumption in these 4 GLO1 variant strains as compared to the control strain RN1216H. Strain RN1216 ZrouG_H showed faster and higher $CO_2$ production rates in the first 20 hours of the experiment as compared to RN1216H, indicating a faster glucose and slower xylose consumption as compared to the 5 other strains tested in this AFM experiment. The HPLC data (Tables 13, 14, 15, 16, 17, 18 and FIGS. 28, 29, 30, 31, 32, 33) indeed confirm faster glucose and xylose consumption in the RN1216 ScG_H, RN1216 CglaG_H, RN1216 KIG_H and RN1216 CmagG_H strains as compared to the RN1216H strain. The HPLC data also confirm faster glucose consumption in the RN1216 ZrouG_H strains as compared to the 5 other strains tested in this AFM experiment.

TABLE 14

HPLC data RN1216 CglaG_H

| Time (hrs) | Glucose (g/l) | Xylose (g/l) | Ethanol (g/l) |
|---|---|---|---|
| 0 | 50.4 | 53.2 | 0.0 |
| 4 | 49.6 | 53.1 | 1.3 |
| 8 | 49.0 | 55.1 | 2.4 |
| 16 | 29.1 | 53.4 | 10.5 |
| 20 | 9.6 | 46.5 | 19.5 |
| 24 | 1.2 | 43.6 | 24.1 |

TABLE 14-continued

HPLC data RN1216 CglaG_H

| Time (hrs) | Glucose (g/l) | Xylose (g/l) | Ethanol (g/l) |
|---|---|---|---|
| 28 | 0.0 | 35.2 | 28.9 |
| 32 | 0.0 | 24.8 | 32.7 |
| 36 | 0.0 | 15.0 | 37.6 |
| 40 | 0.0 | 7.7 | 41.7 |
| 44 | 0.0 | 3.1 | 44.1 |
| 48 | 0.0 | 1.2 | 44.8 |

TABLE 13

HPLC data RN1216 ScG_H

| Time (hrs) | Glucose (g/l) | Xylose (g/l) | Ethanol (g/l) |
|---|---|---|---|
| 0 | 50.2 | 52.9 | 0.0 |
| 8 | 46.8 | 51.5 | 2.5 |
| 12 | 40.5 | 52.4 | 5.5 |
| 16 | 28.5 | 53.6 | 10.9 |
| 20 | 13.0 | 48.6 | 17.6 |
| 24 | 3.3 | 46.2 | 22.9 |
| 28 | 0.2 | 40.2 | 26.0 |
| 32 | 0.0 | 33.0 | 28.5 |
| 36 | 0.0 | 19.7 | 35.1 |
| 40 | 0.0 | 7.9 | 41.2 |
| 44 | 0.0 | 2.6 | 44.0 |
| 48 | 0.0 | 1.1 | 44.5 |

TABLE 16

HPLC data RN1216 KIG_H

| Time (hrs) | Glucose (g/l) | Xylose (g/l) | Ethanol (g/l) |
|---|---|---|---|
| 0 | 50.5 | 53.0 | 0.0 |
| 8 | 47.8 | 53.8 | 1.7 |
| 16 | 30.8 | 53.3 | 9.6 |
| 20 | 11.8 | 45.5 | 18.5 |
| 24 | 1.1 | 41.0 | 24.6 |
| 28 | 0.2 | 33.9 | 25.6 |
| 32 | 0.0 | 27.7 | 31.0 |
| 36 | 0.0 | 15.8 | 37.4 |
| 40 | 0.0 | 7.9 | 41.6 |
| 44 | 0.0 | 3.3 | 44.3 |
| 48 | 0.0 | 1.4 | 44.8 |

TABLE 15

HPLC data RN1216 ZrouG_H

| Time (hrs) | Glucose (g/l) | Xylose (g/l) | Ethanol (g/l) |
|---|---|---|---|
| 0 | 50.3 | 53.0 | 0.0 |
| 4 | 48.6 | 53.1 | 0.7 |
| 12 | 38.4 | 51.2 | 5.1 |
| 16 | 26.1 | 53.1 | 11.3 |
| 20 | 3.5 | 46.8 | 21.8 |
| 24 | 0.4 | 44.0 | 24.1 |
| 28 | 0.0 | 36.8 | 28.2 |
| 32 | 0.0 | 29.4 | 30.6 |
| 36 | 0.0 | 21.6 | 34.5 |
| 40 | 0.0 | 15.4 | 37.9 |
| 44 | 0.0 | 10.3 | 40.7 |
| 48 | 0.0 | 6.7 | 42.3 |

TABLE 18

HPLC data RN1216H

| Time (hrs) | Glucose (g/l) | Xylose (g/l) | Ethanol (g/l) |
|---|---|---|---|
| 0 | 50.5 | 52.9 | 0.0 |
| 8 | 45.7 | 51.1 | 4.2 |
| 12 | 34.6 | 51.0 | 7.1 |
| 16 | 27.8 | 50.0 | 9.9 |
| 20 | 16.3 | 50.7 | 15.8 |
| 24 | 6.8 | 47.8 | 20.7 |
| 28 | 1.1 | 44.6 | 24.1 |
| 32 | 0.0 | 39.2 | 25.8 |
| 36 | 0.0 | 28.0 | 31.6 |
| 40 | 0.0 | 12.8 | 30.8 |
| 44 | 0.0 | 8.9 | 41.5 |
| 48 | 0.0 | 5.3 | 42.7 |

TABLE 17

HPLC data RN1216 CmagG_H

| Time (hrs) | Glucose (g/l) | Xylose (g/l) | Ethanol (g/l) |
|---|---|---|---|
| 0 | 50.5 | 52.8 | 0.0 |
| 4 | 46.5 | 50.3 | 3.2 |
| 8 | 40.4 | 49.4 | 7.1 |
| 12 | 33.3 | 49.6 | 9.0 |
| 16 | 31.0 | 52.3 | 9.9 |
| 24 | 2.3 | 43.6 | 23.8 |
| 28 | 0.0 | 35.4 | 28.9 |
| 32 | 0.0 | 24.6 | 32.7 |
| 36 | 0.0 | 14.5 | 37.8 |
| 40 | 0.0 | 6.8 | 41.6 |
| 44 | 0.0 | 2.5 | 44.1 |
| 48 | 0.0 | 0.9 | 44.8 |

These results show that overexpression of the GLO1-gene derived from the strains *S. cerevisiae, C. glabrata, K. lactis* or *C. magnoliae* leads to a faster and more efficient fermentation of biomass sugars, in this case xylose and glucose, leading to a reduced overall fermentation time and more efficient conversion of the aforementioned sugars into ethanol. An exception is the overexpression of the GLO1-gene derived from the strain *Z. rouxii*, which shows a faster glucose consumption as compared to the other strains tested in this experiment, but the overall performance of this strain is worse.

The invention claimed is:

1. A *Saccharomyces* cell capable of converting one or more pentose sugar and one or more hexose sugar into fermentation product, comprising a nucleotide sequence encoding a xylose isomerase, said cell constitutively expressing one or more heterologous or homologous polypeptide-having the amino acid sequence set out in SEQ ID NO:20, or a variant polypeptide thereof having at least about 60% sequence identity to SEQ ID NO:20, wherein the coding region of the GRE3 aldose reductase gene is inactivated, and wherein the sugar conversion is faster as compared to a control *Saccharomyces* which does not constitutively express the polypeptide of SEQ ID NO: 20 or a variant thereof having at least about 60% sequence identity to SEQ ID NO: 20.

2. A *Saccharomyces* cell capable of converting one or more pentose sugar and or one or more hexose sugar into fermentation product, comprising a constitutively expressed heterologous or homologous polynucleotide which comprises:
    (a) the nucleotide sequence as set forth in SEQ ID NO:27; or
    (b) codon-pair optimized nucleotide sequence of SEQ ID NO:27, wherein the coding region of the GRE3 aldose reductase gene is inactivated, and wherein the sugar conversion is faster as compared to a control *Saccharomyces* which does not comprise SEQ ID NO: 27, or a codon-pair optimized sequence thereof, and which does not contain an inactivated GRE3 aldose reductase gene.

3. The *Saccharomyces* cell according claim 1, wherein the cell further comprises one or more genetic modifications resulting in:
    (a) an increase in transport of xylose in the cell;
    (b) an increase in xylulose kinase activity;
    (c) an increase in flux through the pentose phosphate pathway;
    (d) a decrease in sensitivity to catabolite repression;
    (e) an increase in tolerance to ethanol, osmolarity or organic acid; or
    (f) a reduced production of by-product.

4. The *Saccharomyces* cell according to claim 3, wherein the one or more genetic modifications result in overexpression of at least one gene encoding an enzyme of the non-oxidative part of the pentose phosphate pathway.

5. The *Saccharomyces* cell according to claim 4, wherein the gene is a gene encoding a ribulose-5-phosphate isomerase, a ribulose-5-phosphate epimerase, a transketolase or a transaldolase.

6. The *Saccharomyces* cell according to claim 3, wherein the one or more genetic modifications result in overexpression of a gene encoding a xylulose kinase.

7. The *Saccharomyces* cell according to claim 3 which has ability to use L-arabinose, wherein the genes TAL1, TKL1, RPE1 and RKI1 are overexpressed.

8. The *Saccharomyces* cell according to claim 1, wherein coding region of the GRE3-gene is inactivated by replacement of the coding region with a nucleotide sequence comprising the genes TAL1, TKL1, RPE1 and RKI1.

9. The *Saccharomyces* cell according to claim 1, wherein the genes araA, araB and araD are expressed.

10. The *Saccharomyces* cell according to claim claim 1, wherein one or more constitutively expressed or constitutively overexpressed genes are stably integrated into the genome of the cell.

11. The process for producing a fermentation product which process comprises fermenting a medium comprising a source of xylose and/or arabinose with a cell according to claim 1 such that the cell ferments xylose and/or arabinose to the fermentation product.

12. The process according to claim 11, wherein the fermentation product is selected from the group consisting of ethanol, butanol, lactic acid, 3-hydroxy-propionic acid, acrylic acid, acetic acid, succinic acid, citric acid, malic acid, fumaric acid, itaconic acid, an amino acid, 1,3-propane-diol, ethylene, glycerol, a β-lactam antibiotic and a cephalosporin.

13. The process according to claim 12 wherein the fermentation product is ethanol.

14. The process according to claim 11, wherein the process is anaerobic.

15. A *Saccharomyces* cell capable of converting one or more pentose sugar and one or more hexose sugar into fermentation product under micro-aerophilic or anaerobic conditions, comprising a nucleotide sequence encoding a xylose isomerase, said cell constitutively expressing one or more heterologous or homologous polypeptide-having the amino acid sequence set out in SEQ ID NO:20, or a variant polypeptide thereof having at least about 60% sequence identity to SEQ ID NO:20, wherein the coding region of the GRE3 aldose reductase gene is inactivated, and wherein the sugar conversion is faster as compared to a control *Saccharomyces* which does not constitutively express the polypeptide of SEQ ID NO: 20 or a variant thereof having at least about 60% sequence identity to SEQ ID NO: 20, cultured under the same micro-aerophilic or anaerobic conditions.

16. The *Saccharomyces* cell of claim 2, wherein the codon-pair optimized sequence has at least about 60% identity to SEQ ID NO: 27.

17. The *Saccharomyces* cell of claim 2, wherein the codon optimized sequence is is SEQ ID NO: 34.

18. The *Saccharomyces* cell according to claim 1, wherein the variant polypeptide is selected from the group consisting of SEQ ID NO: 21, SEQ ID NO: 22, and SEQ ID NO: 23.

19. The *Saccharomyces* cell according to claim 18, wherein the variant polypeptide of SEQ ID NO: 21 is encoded by the polynucleotide of SEQ ID NO: 35; the variant polypeptide of SEQ ID NO: 22 is encoded by the polynucleotide of SEQ ID NO: 38; and the variant polypeptide of SEQ ID NO: 23 is encoded by the polynucleotide of SEQ ID NO: 37.

* * * * *